US008609674B2

(12) United States Patent
Perez-Medrano et al.

(10) Patent No.: US 8,609,674 B2
(45) Date of Patent: Dec. 17, 2013

(54) POTASSIUM CHANNEL MODULATORS

(75) Inventors: Arturo Perez-Medrano, Grayslake, IL (US); Sridhar Peddi, Grayslake, IL (US); David DeGoey, Salem, WI (US)

(73) Assignee: AbbVie Inc., North Chicago, IL (US)

( * ) Notice: Subject to any disclaimer, the term of this patent is extended or adjusted under 35 U.S.C. 154(b) by 93 days.

(21) Appl. No.: 13/287,647

(22) Filed: Nov. 2, 2011

(65) Prior Publication Data

US 2012/0122890 A1    May 17, 2012

Related U.S. Application Data

(60) Provisional application No. 61/414,274, filed on Nov. 16, 2010.

(51) Int. Cl.
| | | |
|---|---|---|
| C07D 239/92 | (2006.01) | |
| C07D 495/04 | (2006.01) | |
| A61K 31/517 | (2006.01) | |
| A61K 31/519 | (2006.01) | |
| A61P 25/00 | (2006.01) | |

(52) U.S. Cl.
USPC ........................................ 514/266.3; 544/287

(58) Field of Classification Search
USPC ........................................ 544/287; 514/266.3
See application file for complete search history.

(56) References Cited

U.S. PATENT DOCUMENTS

| | | | |
|---|---|---|---|
| 4,252,951 | A | 2/1981 | Jackson et al. |
| 7,511,013 | B2 | 3/2009 | Molino et al. |
| 7,514,068 | B2 | 4/2009 | Tung |
| 7,521,421 | B2 | 4/2009 | Naicker et al. |
| 7,528,131 | B2 | 5/2009 | Persichetti et al. |
| 7,531,685 | B2 | 5/2009 | Czarnik |
| 7,534,814 | B2 | 5/2009 | Ascher et al. |
| 7,538,189 | B2 | 5/2009 | Naicker et al. |
| 2005/0059823 | A1 | 3/2005 | McNaughton-Smith et al. |
| 2009/0082471 | A1 | 3/2009 | Czarnik |
| 2009/0088416 | A1 | 4/2009 | Czarnik |
| 2009/0093422 | A1 | 4/2009 | Tung et al. |
| 2009/0105147 | A1 | 4/2009 | Masse |
| 2009/0105307 | A1 | 4/2009 | Galley et al. |
| 2009/0105338 | A1 | 4/2009 | Czarnik |
| 2009/0111840 | A1 | 4/2009 | Herold et al. |
| 2009/0118238 | A1 | 5/2009 | Czarnik |
| 2009/0131363 | A1 | 5/2009 | Harbeson |
| 2009/0131485 | A1 | 5/2009 | Liu et al. |
| 2009/0137457 | A1 | 5/2009 | Harbeson |

FOREIGN PATENT DOCUMENTS

| | | |
|---|---|---|
| WO | WO9507271 A1 | 3/1995 |
| WO | WO9710223 A1 | 3/1997 |
| WO | WO2004058704 A2 | 7/2004 |
| WO | WO2005099353 A2 | 10/2005 |
| WO | WO2006008754 A1 | 1/2006 |
| WO | 2007008541 A2 | 1/2007 |
| WO | WO2007057447 A1 | 5/2007 |

OTHER PUBLICATIONS

Berge, S. M. et al., "Pharmaceutical Salts," Journal of Pharmaceutical Sciences, 1977, vol. 66 (1), pp. 1-19.

Beylot, M. et al., "In Vivo Studies of Intrahepatic Metabolic Pathways," Diabetes Metabolism, 1997, vol. 23 (3), pp. 251-257.

Blackburn-Munro G., et al., "Retigabine: Chemical Synthesis to Clinical Application," CNS Drug Reviews, 2005, vol. 11 (1), pp. 1-20.

Blagojevic, N. et al., "Role of heavy water In Boron Neutron Capture Therapy," Topics in Dosimetry & Treatment Planning for Neutron Capture Therapy, 1994, pp. 125-134.

Blake, M. I. et al., "Studies With Deuterated Drugs," Journal of Pharmaceutical Sciences, 1975, vol. 64 (3), pp. 367-391.

Brickner, S.J. et al., "Synthesis and Antibacterial Activity of U-100592 and U-100766, Two Oxazolidinone Antibacterial Agents for the Potential Treatment of Multidrug-Resistant Gram-Positive Bacterial Infections," Journal of Medicinal Chemistry, 1996, vol. 39 (3), pp. 673-679.

Campos K.R., et al., "A General Method for the Highly Diastereoselective, Kinetically Controlled Alkylation of (+)-Nopinone," Tetrahedron Letters, 2002, vol. 43, pp. 6957-6959.

Chaplan S.R., et al., "Quantitative Assessment of Tactile Allodynia in the Rat Paw," Journal of Neuroscience Methods, 1994, vol. 53, pp. 55-63.

Cross, L.C. et al., "IUPAC Commission on Nomenclature of Organic Chemistry: Rules for the Nomenclature of Organic Chemistry, Section E: Stereochemistry," Pure and Applied Chemistry, 1976, vol. 45, pp. 13-30.

Czajka, D. M. et al., "Effect of Deuterium Oxide on the Reproductive Potential of Mice," Annals of the New York Academy of Sciences, 1960, vol. 84, pp. 770-779.

Czajka, D. M. et al., "Physiological Effects of Deuterium on Dogs," American Journal of Physiology, 1961, vol. 201 (2), pp. 357-362.

Dalby-Brown W., et al., "K(V)7 Channels: Function, Pharmacology and Channel Modulators," Current Topics in Medicinal Chemistry, 2006, vol. 6 (10), pp. 999-1023.

Eisen M., et al., "Synthesis, Structure Determination and Immobilization of some Dirhodium Complexes with Chiral Binding Thiolato Ligands. Investigation of their Catalytic Activity for Enantioselective Hydrogenation," Inorganica Chimica Acta, 1991, vol. 188, pp. 167-176.

Foster, A. B. et al., "Deuterium Isotope Effects in the Metabolism of Drugs and Xenobiotics: Implications for Drug Design," Advances in Drug Research, 1985, vol. 14, pp. 2-36.

(Continued)

Primary Examiner — Bruck Kifle

(57) ABSTRACT

Disclosed herein are KCNQ potassium channels modulators of formula (I)

wherein $G^1$, $R^2$, $R^{1a}$, $R^{1b}$, X, $X^1$, $X^2$, $X^3$, $R^x$, J, k, n, q, and t are as defined in the specification. Compositions comprising such compounds; and methods for treating conditions and disorders using such compounds and compositions are also described.

14 Claims, No Drawings

(56) References Cited

OTHER PUBLICATIONS

Greene T.W., et al., "Protection for the Amino group," Protective Groups in Organic Synthesis, 1999, Third Edition, pp. 494-653.
Hansen H.H., et al., "Kv7 Channels: Interaction with Dopaminergic and Serotonergic Neurotransmission in the CNS," The Journal of Physiology, 2008, vol. 586 (7), pp. 1823-1832.
Hansen H.H., et al., "The KCNQ Channel Opener Retigabine Inhibits the Activity of Mesencephalic Dopaminergic Systems of the Rat," The Journal of Pharmacology and Experimental Therapeutics, 2006, vol. 318 (3), pp. 1006-1019.
Jentsch T.J., "Neuronal KCNQ Potassium Channels: Physiology and Role in Disease," Nature Reviews Neuroscience, 2000, vol. 1 (1), pp. 21-30.
Joshi S. K., et al., "Comparison of Antinociceptive Actoins of Standard Analgesics in Attenuating Capsaicin and Nerve-Injury-Induced Mechanical Hypersensitivty ," Neuroscience, 2006, vol. 143, pp. 587-596.
Kato, S. et al., "Synthesis of Deuterated Mosapride Citrate," Journal of Labelled Compounds and Radiopharmaceuticals, 1995, vol. 36 (10), pp. 927-932.
Kushner, et al., "Pharmacological uses and perspectives of heavy water and deuterated compounds," Canadian Journal of Physiology and Pharmacology, 1999, vol. 77 (2), pp. 79-88.
Lizondo, J. et al., "Linezolid: Oxazolidinone antibacterial," Drugs of the Future, 1996, vol. 21 (11), pp. 1116-1123.
Mallesham, B. et al., "Highly Efficient CuI-Catalyzed Coupling of Aryl Bromides With Oxazolidinones Using Buchwald's Protocol: A Short Route to Linezolid and Toloxatone," Organic Letters, 2003, vol. 5 (7), pp. 963-965.
Miceli F., et al., "Molecular Pharmacology and Therapeutic Potential of Neuronal Kv7-Modulating Drugs," Current Opinion in Pharmacology , 2008, vol. 8 (1), pp. 65-74.
Munro G., et al. , "Kv7 (KCNQ) Channel Modulators and Neuropathic Pain," Journal of Medicinal Chemistry, 2007, vol. 50 (11), pp. 2576-2582.
Newman-Evans R.H., et al., "The Influence of Intramolecular Dynamics on Branching Ratios in Thermal Rearrangements," Journal of Organic Chemistry, 1990, vol. 55, pp. 695-711.
Nikitina L.E., et al., "Reaction of Beta-Pinene and Thiols in the Presence of Lewis Acids," Chemistry of Natural Compounds, 2006, vol. 42 (2), pp. 178-181.
Poste G. et al., "Lipid Vesicles as Carriers for Introducing Biologically Active Materials into Cells," Methods in Cell Biology, 1976, vol. 14, pp. 33-71.
Roeloffs R., et al., "In Vivo Profile of ICA-27243 [N-(6-Chloro-pyridin-3-yl)-3,4-difluoro-benzamide], a Potent and Selective KCNQ2/Q3(Kv7.2/Kv7.3) Activator in Rodent Anticonvulsant Models," The Journal of Pharmacology and Experimental Therapeutics, 2008, vol. 326 (3), pp. 818-828.
Roza C., et al., "Retigabine, the Specific KCNQ Channel Opener, Blocks Ectopic Discharges in Axotomized Sensory Fibres," Pain, 2008, vol. 138 (3), pp. 537-545.
Sotty F., et al., "Antipsychotic-Like Effect of Retigabine [N-(2-Amino-4-(Fluorobenzylamino)-Phenyl)Carbamic Acid Ester], A Kcnq Potassium Channel Opener, Via Modulation of Mesolimbic Dopaminergic Neurotransmission," The Journal of Pharmacology and Experimental Therapeutics, 2009, vol. 328 (3), pp. 951-962.
Streng T., et al., "Urodynamic Effects of the K+ Channel (KCNQ) Opener Retigabine in Freely Moving, Conscious Rats ," The Journal of Urology, 2004, vol. 172 (5 pt 1), pp. 2054-2058.
Thomson, J.F., "Physiological Effects of D20 in Mammals," Annals of the New York Academy of Sciences, 1960, vol. 84, pp. 736-744.
Wickenden A.D., et al., "Retigabine, A Novel Anti-Convulsant, Enhances Activation of KCNQ2/Q3 Potassium Channels," Molecular Pharmacology, 2000, vol. 58 (3), pp. 591-600.
Wu, Y.J., et al., "Fluorine Substitution Can Block Cyp3a4 Metabolism-Dependent Inhibition: Identification of (S)-N-[1-(4-Fluoro-3-Morpholin-4-Ylphenyl)Ethyl]-3- (4-Fluorophenyl)Acrylamide as an Orally Bioavailable KCNQ2 Opener Devoid of Cyp3a4 Metabolism-Dependent Inhibition," The Journal of Medicinal Chemistry, 2003, vol. 46 (18), pp. 3778-3781.
Wu Y.J., et al., "(S)-N-[1-(3-Morpholin-4-Ylphenyl)Ethyl]-3-Phenylacrylamide: An Orally Bioavailable KCNQ2 Opener with Significant Activity in a Cortical Spreading Depression Model of Migraine," The Journal of Medicinal Chemistry, 2003, vol. 46 (15), pp. 3197-3200.
Bennett et al., "A peripheral mononeuropathy in rat that produces disorders of pain sensation like those seen in man," Pain, 1988, vol. 33(1), pp. 87-107.
Braga et al., "Making crystals from crystals: a green route to crystal engineering and polymorphism".Chem. Commun., 2005, pp. 3635-3645.
Chemical Abstracts, STN Registry No. 422275-73-8, Supplier Ambinter (May 28, 2002).
Database Registry Chemical Abstracts Service, Columbus, Ohio, US; 2004, XP002612331 Database accession No. 786722-52-9.
Database Registry Chemical Abstracts Service, Columbus, Ohio, US; 2008, XP002612332 Database accession No. 1005243-81-1.
Dixon, W.J., "Efficient analysis of experimental observations," Annual Review of Pharmacology and Toxicology, 1980, vol. 20, pp. 441-462.
Ettmayer, Peter, Medicinal Chemistry, 2004, 47(10), pp. 2394-2404.
International Search Report and Written Opinion for PCT/US2011/058953 dated Dec. 23, 2011.
Kim et al., "An experimental model for peripheral neuropathy produced by segmental spinal nerve ligation in the rat," Pain, 1992, vol. 50(3), pp. 355-363.
Klosa, J. "Synthesis of Amides in the Quinazolone Series," Journal fuer Praktische Chemie (1966), 31(3-4), 140-148. See CAPLUS Accession No. 1966:412304 Attached.
Morissette et al., "High-throughput crystallization: polymorphs, salts, co-crystals and solvates of pharmaceutical solids," Advanced Drug Delivery Reviews (2004), 56, pp. 275-300.
Stella, V. J., "Prodrugs as therapeutics," Expert Opinion on Therapeutic Patents (2004) 14(3), pp. 277-280.
Testa, B., "Prodrug research: futile or fertile?" Biochemical Pharmacology, (2004) 68(11), pp. 2097-2106.
Vippagunta, S.R., "Crystalline Solids," Adv. Drug. Delivery Rev. (2001) 48(1), pp. 3-26.
Wolff et al., Burger's Medicinal Chemistry, 5th Ed., 1994, vol. 1, pp. 975-977.

POTASSIUM CHANNEL MODULATORS

CROSS-REFERENCE TO RELATED APPLICATIONS

This application claims the benefit of provisional application Ser. No. 61/414,274 filed Nov. 16, 2010, which is hereby incorporated by reference as if set forth in its entirety.

TECHNICAL FIELD AND BACKGROUND

Compounds that are potassium channel modulators, compositions comprising such compounds, and methods of treating conditions and disorders using such compounds and compositions are disclosed.

Potassium channels are membrane-bound proteins responsible for regulating the flow of potassium ions through a cell membrane. The KCNQ (or $K_v7$) family is an important class of potassium channel that plays a key role in the process of neuronal excitability. There are five recognized subtypes of KCNQ channel: KCNQ1, KCNQ2, KCNQ3, KCNQ4, and KCNQ5. The KCNQ2-KCNQ5 subtypes represent the neuronal KCNQ subtypes. Miceli, *Curr. Op. Pharmacol.*, 2008, 8, 65. Functional KCNQ channels are formed by the assemblage of four individual subunits into a homotetramer or heterotetramer. The KCNQ2/3 channel is composed of a heterotetrameric assemblage of the KCNQ2 and KCNQ3 proteins.

The neuronal KCNQ channels are voltage-gated potassium channels that control cellular excitability by hyperpolarizing membrane potential, reducing action potential firing, and decreasing neurotransmitter release. Jentsch, *Nature Reviews Neurosci.*, 2000, 1, 21; Dalby-Brown, *Curr. Top. Med. Chem.*, 2006, 6, 999; Munro, *J. Med. Chem.*, 2007, 50, 2576. Neuronal KCNQ channels become activated on cellular depolarization (i.e., a change in voltage). See, Roza et al., *Pain*, 2008, 138, 537; Wickenden et al., *Mol. Pharmacol.*, 2000, 58, 591.

Activation of KCNQ channels by KCNQ openers causes an outflow of potassium ions from the cell, reducing the membrane potential (i.e., hyperpolarization), and thereby decreasing cellular excitability and action potential generation. Miceli, *Curr. Op. Pharmacol.*, 2008, 8, 65. In view of the role that KCNQ channels play in controlling cellular excitability and their distribution throughout the nervous system, KCNQ channel openers have been reported to have therapeutic utility in the treatment of a number of disorders characterized by abnormal neuronal excitability including: epilepsy, pain, migraine, anxiety, and overactive bladder. Dalby-Brown, *Curr. Top. Med. Chem.*, 2006, 6, 999; Streng, *J. Urol.*, 2004, 172, 2054. The dampening effect on neuronal excitability of KCNQ opening has also been implicated as a mechanism to inhibit the release of neurotransmitters (e.g., dopamine and serotonin) involved in schizophrenia, anxiety, and substance abuse. Hansen, *J. Physiol.* 2008, 1823.

A number of KCNQ openers, including flupirtine and retigabine, have been reported to be efficacious in treating various pain states in humans or rodents. These pain states include neuropathic pain (including diabetic polyneuropathy), inflammatory pain, persistent pain, cancer pain, and postoperative pain. Munro, *J. Med. Chem.*, 2007, 50, 2576; Dalby-Brown, *Curr. Top. Med. Chem.*, 2006, 6, 999. Thus, KCNQ openers have utility in treating a variety of painful conditions including, but not limited to, the foregoing types of pain.

The utility of KCNQ openers in the treatment of epilepsy is shown by the anticonvulsant and antiseizure activity of flupirtine, retigabine, and ICA-27243. Roeloffs, *J. Pharmacol. Exp. Ther.*, 2008, 326, 818; Miceli, *Curr. Op. Pharmacol.*, 2008, 8, 65; Blackburn-Munro, *CNS Drug Rev.*, 2005, 11, 1.

The utility of KCNQ openers in the treatment of migraine is indicated by the activity of KCNQ openers in an animal model of migraine. Wu, *J. Med. Chem.*, 2003, 46, 3197; Wu, *J. Med. Chem.*, 2003, 46, 3778.

The utility of KCNQ openers as anxiolytics is indicated by the activity of retigabine in animal models of anxiety. Dalby-Brown, *Curr. Top. Med. Chem.*, 2006, 6, 999.

The utility of KCNQ openers in the treatment of schizophrenia is indicated by the ability of retigabine to inhibit the activity of dopaminergic systems (Hansen, *J. Pharmacol. Exp. Ther.*, 2006, 318, 1006; Hansen, *J. Physiol.* 2008, 1823; Sotty, *J. Pharmacol. Exp. Ther.*, 2009, 328, 951) and by retigabine's efficacy in animal models of schizophrenia. Sotty, *J. Pharmacol. Exp. Ther.*, 2009, 328, 951.

Flupirtine and retigabine both possess liabilities in terms of adverse effects, including: asthenia, ataxia, insomnia, headache, drowsiness, dizziness, somnolence, dry mouth, nausea, vomiting, gastric and abdominal discomfort, sedation or loss of motor coordination. Miceli, *Curr. Op. Pharmacol.*, 2008, 8, 65; Munro, *J. Med. Chem.*, 2007, 50, 2576; Blackburn-Munro, *CNS Drug Rev.*, 2005, 11, 1. These adverse effects may be related to activation of one or more KCNQ subtypes not primarily responsible for the desirable therapeutic response. Thus, there is a need for KCNQ openers with efficacy in one or more of the foregoing disorders, states, or conditions, but without the side-effects of flupirtine or retigabine. KCNQ openers that selectively activate a particular subtype or subtypes may possess such efficacy with reduced side-effects.

SUMMARY

Provided herein are compounds of formula (I)

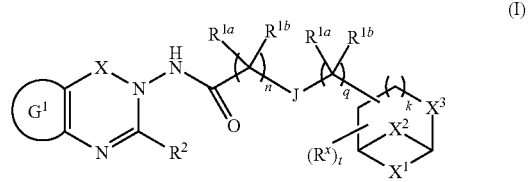

(I)

or pharmaceutically acceptable salts or solvates thereof, wherein

J is absent, O, N(H), N(alkyl), S, S(O), or $S(O)_2$;

n is 1 or 2;

q is 0, 1, or 2;

ring $G^1$ is benzo, heteroaryl, cycloalkyl, or heterocycle, each of which is independently unsubstituted or substituted with 1, 2, 3, 4, or 5 substituents as represented by T, wherein each T is independently alkyl, alkenyl, alkynyl, halogen, haloalkyl, oxo, —CN, —$NO_2$, —$OR^a$, —$NR^aR^b$, —$SR^a$, —$S(O)R^a$, —$S(O)_2R^a$, —$OC(O)R^a$, —$OC(O)NR^aR^b$, —$C(O)R^a$, —$C(O)OR^a$, —$C(O)NR^aR^b$, —$S(O)_2NR^aR^b$, —$N(R^a)C(O)NR^aR^b$, —$N(R^a)S(O)_2NR^aR^b$, —$(CR^{za}R^{zb})_m$—CN, —$(CR^{za}R^{zb})_m$—$NO_2$, —$(CR^{za}R^{zb})_m$—$OR^a$, —$(CR^{za}R^{zb})_m$—$NR^aR^b$, —$(CR^{za}R^{zb})_m$—$S(O)R^a$, —$(CR^{za}R^{zb})_m$—$S(O)_2R^a$, —$(CR^{za}R^{zb})_m$—$OC(O)R^a$, —$(CR^{za}R^{zb})_m$—$OC(O)NR^aR^b$, —$(CR^{za}R^{zb})_m$—$C(O)R^a$, —$(CR^{za}R^{zb})_m$—$C(O)OR^a$, —$(CR^{za}R^{zb})_m$—$C(O)NR^aR^b$, —$(CR^{za}R^{zb})_m$—$S(O)_2NR^aR^b$, —$(CR^{za}R^{zb})_m$—$N(R^a)C(O)NR^aR^b$, or —$(CR^{za}R^{zb})_m$—$N(R^a)S(O)_2NR^aR^b$;

X is C(O) or $S(O)_2$;

$R^{1a}$ and $R^{1b}$, at each occurrence, are each independently hydrogen, alkyl, halogen, or haloalkyl; $R^{1a}$ and $R^{1b}$, together with the carbon atom to which they are attached, optionally form a 3-, 4-, 5-, or 6-membered monocyclic cycloalkyl when $R^{1a}$ and $R^{1b}$ are alkyl or haloalkyl;

k is 0 or 1;

$X^1$, $X^2$, and $X^3$ are each independently $CH_2$, O, S, S(O), or $S(O)_2$; with the proviso that at least two of $X^1$, $X^2$, and $X^3$ are $CH_2$;

t is 0, 1, 2, 3, or 4;

$R^x$ is an optional substituent on any substitutable atom of the ring containing $X^1$, $X^2$, and $X^3$, and each $R^x$ is independently alkyl, halogen, haloalkyl, $OR^a$, $SR^a$, or CN;

$R^2$ is hydrogen, alkyl, haloalkyl, —$OR^{2c}$, —OC(O)N($R^{2c}$)($R^{2f}$), —S(O)$R^{2c}$, —S(O)$_2R^{2c}$, —S(O)$_2$N($R^{2c}$)($R^{2f}$), —C(O)$R^{2c}$, —C(O)O$R^{2c}$, —C(O)N($R^{2c}$)($R^{2f}$), —N($R^{2d}$)($R^{2e}$), $G^{2a}$, —(C$R^{2a}R^{2b}$)$_p$-$G^{2a}$, —(C$R^{2a}R^{2b}$)$_p$—$OR^{2c}$, —(C$R^{2a}R^{2b}$)$_p$—OC(O)N($R^{2c}$)($R^{2f}$), —(C$R^{2a}R^{2b}$)$_p$—$SR^{2c}$, —(C$R^{2a}R^{2b}$)$_p$—S(O)$R^{2c}$, —(C$R^{2a}R^{2b}$)$_p$—S(O)$_2R^{2c}$, —(C$R^{2a}R^{2b}$)$_p$—S(O)$_2$N($R^{2c}$)($R^{2f}$), —(C$R^{2a}R^{2b}$)$_p$—C(O)$R^{2c}$, —(C$R^{2a}R^{2b}$)$_p$—C(O)O$R^{2c}$, —(C$R^{2a}R^{2b}$)$_p$—C(O)N($R^{2c}$)($R^{2f}$), or —(C$R^{2a}R^{2b}$)$_p$—N($R^{2d}$)($R^{2e}$), $R^{2c}$, at each occurrence, is independently hydrogen, alkyl, haloalkyl, -alkylenyl-$OR^a$, -alkylenyl-N($R^{2f}$)($R^{2g}$), -alkylenyl-CN, $G^{2a}$, or —(C$R^{2a}R^{2b}$)$_p$-$G^{2a}$;

$R^{2d}$ and $R^{2e}$, at each occurrence, are each independently hydrogen, alkyl, haloalkyl, $G^{2a}$, —(C$R^{2a}R^{2b}$)$_p$-$G^{2a}$, C(O)$R^{2c}$, C(O)O$R^{2c}$, S(O)$_2R^{2c}$, -alkylenyl-$OR^a$, -alkylenyl-N($R^{2f}$)($R^{2g}$), or -alkylenyl-CN;

$R^{2f}$, at each occurrence, is independently hydrogen, alkyl, or haloalkyl;

$R^{2g}$, at each occurrence, is independently hydrogen, alkyl, haloalkyl, C(O)$R^c$, C(O)O$R^c$, or S(O)$_2R^c$;

$G^{2a}$, at each occurrence, is independently aryl, heteroaryl, heterocycle, cycloalkyl, or cycloalkenyl; each of which is independently unsubstituted or substituted with 1, 2, 3, or 4 substituents independently selected from the group consisting of $G^a$, alkyl, alkenyl, alkynyl, halogen, haloalkyl, oxo, —CN, —$NO_2$, —$OR^a$, —OC(O)$R^a$, —OC(O)N$R^aR^b$, —N$R^aR^b$, —$SR^a$, —S(O)$R^a$, —S(O)$_2R^a$, —OC(O)$R^a$, —C(O)$R^a$, —C(O)O$R^a$, —C(O)N$R^aR^b$, —S(O)$_2$N$R^aR^b$, —N($R^a$)C(O)N$R^aR^b$, —N($R^a$)S(O)$_2$N$R^aR^b$, —(C$R^{za}R^{zb}$)$_m$-$G^a$, —(C$R^{za}R^{zb}$)$_m$—CN, —(C$R^{za}R^{zb}$)$_m$—$NO_2$, —(C$R^{za}R^{zb}$)$_m$—$OR^a$, —(C$R^{za}R^{zb}$)$_m$—OC(O)$R^a$, —(C$R^{za}R^{zb}$)$_m$—OC(O)N$R^aR^b$, —(C$R^{za}R^{zb}$)$_m$—N$R^aR^b$, —(C$R^{za}R^{zb}$)$_m$—$SR^a$, —(C$R^{za}R^{zb}$)$_m$—S(O)$_2R^a$, —(C$R^{za}R^{zb}$)$_m$—OC(O)$R^a$, —(C$R^{za}R^{zb}$)$_m$—C(O)$R^a$, —(C$R^{za}R^{zb}$)$_m$—C(O)O$R^a$, —(C$R^{za}R^{zb}$)$_m$—C(O)N$R^aR^b$, —(C$R^{za}R^{zb}$)$_m$—S(O)$_2$N$R^aR^b$, —(C$R^{za}R^{zb}$)$_m$—N($R^a$)C(O)N$R^aR^b$, and —(C$R^{za}R^{zb}$)$_m$—N($R^a$)S(O)$_2$N$R^aR^b$, $G^a$, at each occurrence, is independently aryl, heteroaryl, heterocycle, cycloalkyl, or cycloalkenyl; each of which is independently unsubstituted or substituted with 1, 2, or 3 substituents selected from the group consisting of alkyl, alkenyl, alkynyl, halogen, haloalkyl, oxo, —CN, —$NO_2$, —$OR^a$, —N$R^aR^b$, —$SR^a$, —S(O)$R^a$, —S(O)$_2R^a$, —OC(O)$R^a$, —C(O)$R^a$, —C(O)O$R^a$, —C(O)N$R^aR^b$, —S(O)$_2$N$R^aR^b$, —N($R^a$)C(O)N$R^aR^b$, —N($R^a$)S(O)$_2$N$R^aR^b$, —(C$R^{za}R^{zb}$)$_m$—CN, —(C$R^{za}R^{zb}$)$_m$—$NO_2$, —(C$R^{za}R^{zb}$)$_m$—$OR^a$, —(C$R^{za}R^{zb}$)$_m$—N$R^aR^b$, —(C$R^{za}R^{zb}$)$_m$—$SR^a$, —(C$R^{za}R^{zb}$)$_m$—S(O)$R^a$, —(C$R^{za}R^{zb}$)$_m$—S(O)$_2R^a$, —(C$R^{za}R^{zb}$)$_m$—OC(O)$R^a$, —(C$R^{za}R^{zb}$)$_m$—C(O)$R^a$, (C$R^{za}R^{zb}$)$_m$—C(O)O$R^a$, —(C$R^{za}R^{zb}$)$_m$—C(O)N$R^aR^b$, —(C$R^{za}R^{zb}$)$_m$—S(O)$_2$N$R^aR^b$, —(C$R^{za}R^{zb}$)$_m$—N($R^a$)C(O)N$R^aR^b$, and —(C$R^{za}R^{zb}$)$_m$—N($R^a$)S(O)$_2$N$R^aR^b$, $R^a$ and $R^b$, at each occurrence, are each independently hydrogen, alkyl, or haloalkyl;

$R^c$, at each occurrence, is independently alkyl or haloalkyl;

$R^{za}$, $R^{zb}$, $R^{2a}$, and $R^{2b}$, at each occurrence, are each independently hydrogen, alkyl, halogen, or haloalkyl; and m and p, at each occurrence, are each independently 1, 2, 3, or 4.

Compounds described herein or pharmaceutically acceptable salts or solvates thereof are modulators of KCNQ potassium channels and are thus useful in the treatment of diseases, disorders, or conditions of a subject that are responsive to the modulation of the potassium channels.

Present compounds or pharmaceutically acceptable salts or solvates thereof are openers of KCNQ potassium channels and are useful in the treatment of conditions or disorders that are responsive to the opening of the KCNQ potassium channels, including pain.

Another aspect is related to pharmaceutical compositions comprising therapeutically effective amounts of one or more compound(s) described herein or pharmaceutically acceptable salts or solvates thereof, in combination with one or more pharmaceutically acceptable carrier(s). Such compositions can be administered in accordance with a method of the invention, typically as part of a therapeutic regimen for treatment or prevention of conditions and disorders related to the modulation of KCNQ channels. More particularly, the methods are useful for treating disorders or conditions related to pain such as neuropathic pain (including diabetic polyneuropathy), nociceptive pain, persistent pain, osteoarthritic pain, cancer pain, inflammatory pain, postoperative pain, fibromyalgia, chronic widespread pain, musculoskeletal pain, myofascial pain, and temporomandibular joint (TMJ) pain, as well as epilepsy, migraine, overactive bladder, schizophrenia, anxiety, and substance abuse.

Further provided herein are the use of the present compounds or pharmaceutically acceptable salts or solvates thereof, in the manufacture of a medicament for the treatment of the disease conditions described above, alone or in combination with one or more pharmaceutically acceptable carrier(s), particularly for the treatment or alleviation of disorders or conditions related to neuropathic pain (including diabetic polyneuropathy), nociceptive pain, persistent pain, osteoarthritic pain, cancer pain, inflammatory pain, migraine pain, postoperative pain, fibromyalgia, chronic widespread pain, musculoskeletal pain, myofascial pain, and temporomandibular joint (TMJ) pain, epilepsy, migraine, overactive bladder, schizophrenia, anxiety, and substance abuse.

The compounds, compositions comprising the compounds or pharmaceutically acceptable salts or solvates thereof, and methods for treating or preventing conditions and disorders by administering the compounds or compositions thereof are further described herein.

These and other objectives are described in the following paragraphs. These objectives should not be deemed to narrow the scope of the invention.

DETAILED DESCRIPTION

Provided herein are compounds of formula (I)

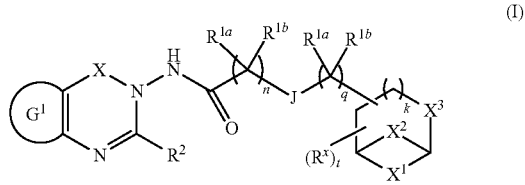

wherein $G^1$, $R^x$, $R^2$, $R^{1a}$, $R^{1b}$, X, $X^1$, $X^2$, $X_3$, J, k, n, q, and t are as defined above in the Summary and below in the Detailed Description. Compositions comprising such compounds and methods for treating conditions and disorders using such compounds and compositions are also disclosed.

In various embodiments, there may be variables that occur more than one time in any substituent or in the compound or any other formulae herein. Definition of a variable on each occurrence is independent of its definition at another occurrence. Further, combinations of variables or substituents are permissible only if such combinations result in stable compounds. Stable compounds are compounds that can be isolated from a reaction mixture.

a. DEFINITIONS

As used in the specification and the appended claims, unless specified to the contrary, the following terms have the meaning indicated:

The term "alkenyl" as used herein, means a straight or branched hydrocarbon chain containing from 2 to 10 carbons and containing at least one carbon-carbon double bond. The term "$C_2$-$C_4$ alkenyl" means an alkenyl group containing 2-4 carbon atoms. Non-limiting examples of alkenyl include buta-2,3-dienyl, ethenyl (vinyl), 3,3-dimethylbutenyl, 2-propenyl, propen-1-yl, 2-methyl-2-propenyl, 3-butenyl, 4-pentenyl, 5-hexenyl, 2-heptenyl, 2-methyl-1-heptenyl, and 3-decenyl.

The term "alkenylene" or "alkenylenyl" means a divalent group derived from a straight or branched chain hydrocarbon of 2 to 4 carbon atoms and contains at least one carbon-carbon double bond. Representative examples of alkenylene and alkenylenyl include, but are not limited to, —CH=CH— and —CH$_2$CH=CH—.

The term "alkyl" as used herein, means a straight or branched, saturated hydrocarbon chain containing from 1 to 10 carbon atoms. Examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 2,2-dimethylethyl, 2,2-dimethylpropyl, 1-methylpropyl, 2-methylpropyl, 1-ethylpropyl, 2,2-dimethylbutyl, 3-methylhexyl, 2,2-dimethylpentyl, 2,3-dimethylpentyl, n-heptyl, n-octyl, n-nonyl, and n-decyl.

The term "alkylene" or "alkylenyl" means a divalent group derived from a straight or branched, saturated hydrocarbon chain, for example, of 1 to 10 carbon atoms or of 1 to 4 carbon atoms. Examples of alkylene and alkylenyl include, but are not limited to, —CH$_2$—, —CH$_2$CH$_2$—, —CH$_2$CH$_2$CH$_2$—, —CH$_2$CH$_2$CH$_2$CH$_2$—, and —CH$_2$CH(CH$_3$)CH$_2$—.

The term "alkynyl" as used herein, means a straight or branched chain hydrocarbon group containing from 2 to 10 carbon atoms and containing at least one carbon-carbon triple bond. The term "$C_2$-$C_4$ alkynyl" means a straight or branched chain hydrocarbon group containing from 2 to 4 carbon atoms. Representative examples of alkynyl include, but are not limited, to acetylenyl, 1-propynyl, 2-propynyl, 3-butynyl, 2-pentynyl, and 1-butynyl.

The term "aryl" as used herein, means phenyl or a bicyclic aryl. The bicyclic aryl is naphthyl, or a phenyl fused to a monocyclic cycloalkyl, or a phenyl fused to a monocyclic cycloalkenyl. Non-limiting examples of the aryl groups include dihydroindenyl (e.g. 2,3-dihydroindenyl), indenyl, naphthyl, dihydronaphthalenyl, and tetrahydronaphthalenyl. The bicyclic aryl is attached to the parent molecular moiety through any carbon atom contained within the bicyclic ring system and can be unsubstituted or substituted.

The term "cycloalkyl" or "cycloalkane" as used herein, means a monocyclic, a bicyclic, or a tricyclic cycloalkyl. The monocyclic cycloalkyl is a carbocyclic ring system containing three to eight carbon atoms, zero heteroatoms and zero double bonds. Examples of monocyclic ring systems include cyclopropyl, cyclobutyl, cyclopentyl, cyclohexyl, cycloheptyl, and cyclooctyl. The bicyclic cycloalkyl is a monocyclic cycloalkyl fused to a monocyclic cycloalkyl ring such as, for example, bicyclo[3.1.0]hexyl. Tricyclic cycloalkyls are exemplified by a bicyclic cycloalkyl fused to a monocyclic cycloalkyl. The monocyclic, bicyclic, and tricyclic cycloalkyls may have one or two alkylene bridges of 1, 2, 3, or 4 carbon atoms, each linking two non-adjacent carbon atoms of the ring system. Non-limiting examples of cycloalkyls having one or two alkylene bridges include, but not limited to, bicyclo[3.1.1]heptane, bicyclo[2.2.1]heptane, bicyclo[2.2.2]octane, bicyclo[3.2.2]nonane, bicyclo[3.3.1]nonane, and bicyclo[4.2.1]nonane, tricyclo[3.3.1.0$^{3,7}$]nonane (octahydro-2,5-methanopentalene or noradamantane), and tricyclo[3.3.1.1$^{3,7}$]decane (adamantane). The cycloalkyls of the present application can be unsubstituted or substituted, and are attached to the parent molecular moiety through any substitutable atom contained within the ring system.

The term "cycloalkenyl" or "cycloalkene" as used herein, means a monocyclic or a bicyclic hydrocarbon ring system. The monocyclic cycloalkenyl has four-, five-, six-, seven-, or eight carbon atoms and zero heteroatoms. The four-membered ring systems have one double bond, the five- or six-membered ring systems have one or two double bonds, and the seven- or eight-membered ring systems have one, two, or three double bonds. Representative examples of monocyclic cycloalkenyl groups include, but are not limited to, cyclobutenyl, cyclopentenyl, cyclohexenyl, cycloheptenyl, and cyclooctenyl. The bicyclic cycloalkenyl is a monocyclic cycloalkenyl fused to a monocyclic cycloalkyl group, or a monocyclic cycloalkenyl fused to a monocyclic cycloalkenyl group. The monocyclic and the bicyclic cycloalkenyl rings may contain one or two alkylene bridges, each consisting of one, two, or three carbon atoms and each linking two non-adjacent carbon atoms of the ring system. Representative examples of the bicyclic cycloalkenyl groups include, but are not limited to, 4,5,6,7-tetrahydro-3aH-indene, octahydronaphthalenyl, and 1,6-dihydro-pentalene. The monocyclic and bicyclic cycloalkenyls can be attached to the parent molecular moiety through any substitutable atom contained within the ring systems, and can be unsubstituted or substituted.

The term "halo" or "halogen" as used herein, means Cl, Br, I, or F.

The term "haloalkyl" as used herein, means an alkyl group, as defined herein, in which one, two, three, four, five, or six hydrogen atoms are replaced by halogen. The term "$C_1$-$C_4$ haloalkyl" means a $C_1$-$C_4$ alkyl group, as defined herein, in which one, two, three, four, five, or six hydrogen atoms are replaced by halogen. Representative examples of haloalkyl include, but are not limited to, chloromethyl, 2-fluoroethyl, 2,2,2-trifluoroethyl, trifluoromethyl, difluoromethyl, pentafluoroethyl, 2-chloro-3-fluoropentyl, trifluorobutyl (such as, but not limited to, 4,4,4-trifluorobutyl), and trifluoropropyl (such as, but not limited thereto, 3,3,3-trifluoropropyl).

The term "heterocycle" or "heterocyclic" as used herein, means a monocyclic heterocycle, a bicyclic heterocycle, or a tricyclic heterocycle. The monocyclic heterocycle is a three-, four-, five-, six-, seven-, or eight-membered ring containing at least one heteroatom independently selected from the group consisting of O, N, and S. The three- or four-membered ring contains zero or one double bond, and one heteroatom selected from the group consisting of O, N, and S. The five-membered ring contains zero or one double bond and one, two, or three heteroatoms selected from the group consisting of O, N, and S. The six-membered ring contains zero, one, or two double bonds and one, two, or three heteroatoms selected from the group consisting of O, N, and S. The seven- and eight-membered rings contains zero, one, two, or three double bonds and one, two, or three heteroatoms selected from the group consisting of O, N, and S. Representative examples of monocyclic heterocycles include, but are not limited to, azetidinyl, azepanyl, aziridinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, oxetanyl, piperazinyl, piperidinyl, pyranyl, pyrazolinyl, pyrazolidinyl, pyrrolinyl, pyrrolidinyl, tetrahydrofuranyl, tetrahydropyranyl, tetrahydrothienyl, thiadiazolinyl, thiadiazolidinyl, thiazolinyl, thiazolidinyl, thiomorpholinyl, thiopyranyl, and trithianyl. The bicyclic heterocycle is a monocyclic heterocycle fused to a phenyl group, or a monocyclic heterocycle fused to a monocyclic cycloalkyl, or a monocyclic heterocycle fused to a monocyclic cycloalkenyl, or a monocyclic heterocycle fused to a monocyclic heterocycle. Non-limiting examples of bicyclic heterocycles include benzopyranyl, benzothiopyranyl, 2,3-dihydrobenzofuranyl, 2,3-dihydro-1H-indolyl, and 2,3-dihydrobenzothienyl. Tricyclic heterocycles are exemplified by a bicyclic heterocycle fused to a phenyl group, or a bicyclic heterocycle fused to a monocyclic cycloalkyl, or a bicyclic heterocycle fused to a monocyclic cycloalkenyl, or a bicyclic heterocycle fused to a monocyclic heterocycle. The monocyclic, bicyclic, and tricyclic heterocycle groups of the present application may have one or two alkylene bridges of 1, 2, 3, or 4 carbon atoms, or one or two alkenylene bridges of two, three, or four carbon atoms, or combinations thereof. Examples of the heterocycles having such alkylene or alkenylene bridge(s) include, but are not limited to, azabicyclo[3.2.1]octane, azabicyclo[2.2.1]heptyl (including 2-azabicyclo[2.2.1]hept-2-yl), octahydro-2,5-epoxypentalene, hexahydro-2H-2,5-methanocyclopenta[b]furan, hexahydro-1H-1,4-methanocyclopenta[c]furan, aza-admantane (1-azatricyclo[3.3.1.1$^{3,7}$]decane), and oxa-adamantane (2-oxatriclo[3.3.1.1$^{3,7}$]decane). The heterocycles of the present application can be unsubstituted or substituted, and are connected to the parent molecular moiety through any carbon atom or any nitrogen atom contained within the rings. The nitrogen and sulfur heteroatoms in the heterocycle rings may optionally be oxidized and the nitrogen atoms may optionally be quarternized.

The term "heteroaryl" as used herein, means a monocyclic heteroaryl or a bicyclic heteroaryl. The monocyclic heteroaryl is a five- or six-membered ring. The five-membered ring contains two double bonds. The five membered ring may contain one heteroatom selected from O or S; or one, two, three, or four nitrogen atoms and optionally one oxygen or one sulfur atom. The six-membered ring contains three double bonds and one, two, three or four nitrogen atoms. Representative examples of monocyclic heteroaryl include, but are not limited to, furanyl, imidazolyl, isoxazolyl, isothiazolyl, oxadiazolyl, 1,3-oxazolyl, pyridinyl, pyridazinyl, pyrimidinyl, pyrazinyl, pyrazolyl, pyrrolyl, tetrazolyl, thiadiazolyl, 1,3-thiazolyl, thienyl, triazolyl, and triazinyl. The bicyclic heteroaryl consists of a monocyclic heteroaryl fused to a phenyl, or a monocyclic heteroaryl fused to a monocyclic cycloalkyl, or a monocyclic heteroaryl fused to a monocyclic cycloalkenyl, or a monocyclic heteroaryl fused to a monocyclic heteroaryl, or a monocyclic heteroaryl fused to a monocyclic heterocycle. Representative examples of bicyclic heteroaryl groups include, but are not limited to, benzofuranyl, benzothienyl, benzoxazolyl, benzimidazolyl, benzoxadiazolyl, 6,7-dihydro-1,3-benzothiazolyl, imidazo[1,2-c]pyridinyl, indazolyl, indolyl, isoindolyl, isoquinolinyl, naphthyridinyl, pyridoimidazolyl, quinolinyl, thiazolo[5,4-b]pyridin-2-yl, thiazolo[5,4-d]pyrimidin-2-yl, and 5,6,7,8-tetrahydroquinolin-5-yl. The monocyclic and bicyclic heteroaryl groups can be substituted or unsubstituted and are connected to the parent molecular moiety through any substitutable carbon atom or any substitutable nitrogen atom contained within the ring systems. The nitrogen and sulfur heteroatoms in the heteraryl rings may optionally be oxidized.

In some instances, the number of carbon atoms in a substituent (e.g., alkyl, alkenyl, alkynyl, alkoxy, haloalkoxy, or cycloalkyl) is indicated by the prefix "$C_x$-$C_y$", wherein x is the minimum and y is the maximum number of carbon atoms in the substituent. Thus, for example, "$C_1$-$C_6$ alkyl" refers to an alkyl substituent containing from 1 to 6 carbon atoms. Illustrating further, $C_3$-$C_6$ cycloalkyl means a saturated carbocyclic ring containing from 3 to 6 carbon ring atoms.

If a substituent is described as being optionally substituted with up to a particular number of non-hydrogen radicals, that substituent may be either (1) not substituted; or (2) substituted by up to that particular number of non-hydrogen radicals or by up to the maximum number of substitutable positions on the substituent, whichever is less. Thus, for example, if a substituent is described as a heteroaryl optionally substituted with up to 5 non-hydrogen radicals, then any heteroaryl with less than 5 substitutable positions would be optionally substituted by up to only as many non-hydrogen radicals as the heteroaryl has substitutable positions. To illustrate, thienyl (which has only four substitutable positions) would be optionally substituted with up to four non-hydrogen radicals.

The term "heteroatom" as used herein, means a nitrogen, oxygen, or sulfur atom.

The term "oxo" as used herein, means a =O group.

The terms "treat", "treating" and "treatment" refer to a method of alleviating or abrogating a disease/condition and/or its attendant symptoms.

The terms "prevent", "preventing" and "prevention" refer to a method of preventing the onset of a disease and/or its attendant symptoms or barring a subject from acquiring a disease. As used herein, "prevent", "preventing" and "prevention" also include delaying the onset of a disease and/or its attendant symptoms and reducing a subject's risk of acquiring a disease.

The term "modulate" refers to the ability of a compound to increase or decrease the function, or activity, of KCNQ channels. "Modulation", as used herein in its various forms, is intended to encompass antagonism, agonism, partial antagonism and/or partial agonism of the activity associated with KCNQ channels. KCNQ channel activators are compounds that, e.g., bind to, stimulate, increase, open, activate, or facilitate KCNQ channels such as, KCNQ2, and/or KCNQ3, and/or KCNQ2/3 potassium channels. Activation of KCNQ channels encompasses either or both of: (1) increasing current through a KCNQ channel; or (2) shifting the half-activation potential of KCNQ channels to lower voltages (i.e. a hyperpolarizing shift of the $V_{1/2}$ for activation).

The "subject" is defined herein to include animals such as mammals, including, but not limited to, primates (e.g., humans), cows, sheep, goats, horses, dogs, cats, rabbits, rats, mice and the like. In preferred embodiments, the subject is a human.

b. Compounds

KCNQ channel modulators have formula (I) as described above.

Particular values of variable groups in compounds of formula (I) are as follows. Such values may be used where appropriate with any of the other values, definitions, claims, or embodiments defined hereinbefore or hereinafter.

In compounds of formula (I), ring $G^1$ has values as disclosed in the Summary.

In certain embodiments, ring $G^1$ is benzo or hetroaryl (e.g. monocyclic heteroaryl such as, but not limited to, thienyl), each of which is optionally substituted as described in the Summary and embodiments herein.

In certain embodiments, ring $G^1$ is optionally substituted benzo, thus, included herein are compounds of formula (I-a)

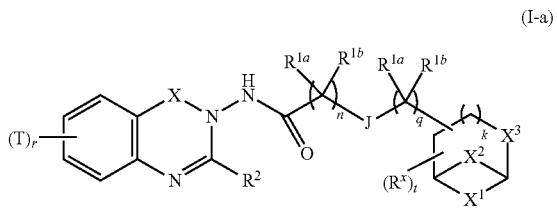

(I-a)

In certain embodiments, ring $G^1$ is optionally substituted heteroaryl. In certain embodiments, ring $G^1$ is optionally substituted monocyclic heteroaryl. Example of such heteroaryl includes, but is not limited to, thienyl. Examples of compounds of formula (I) containing such ring include but are not limited to those represented by formula (I-b) and (I-c):

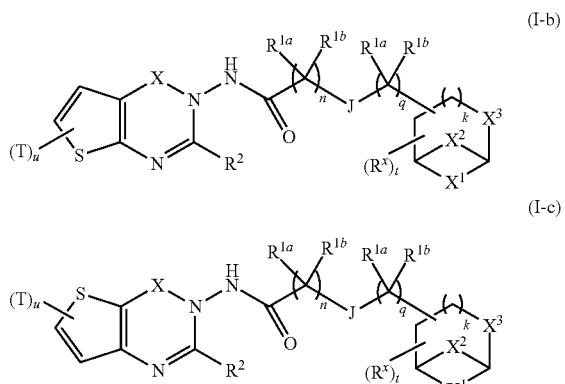

(I-b)

(I-c)

In compounds of formula (I-a)-(I-c), r is 0, 1, 2, 3, or 4; u is 0, 1, or 2; and T, $R^x$, $R^2$, $R^{1a}$, $R^{1b}$, X, $X^1$, $X^2$, $X^3$, J, k, n, q, and t are as described in the Summary and in the embodiments herein.

The variable, J, for compounds of formula (I), (I-a)-(I-c) has values as described in the Summary. Certain embodiments are directed to compounds of formula (I), (I-a)-(I-c) wherein J is absent, or J is O or S. In certain embodiments, J is absent. In embodiments wherein J is absent, it is understood that the $(CR^{1a}R^{1b})_n$ group is directly linked to $(CR^{1a}R^{1b})_q$ moiety, for example, compounds of formula (I) wherein J is absent can be represented by formula (I-d):

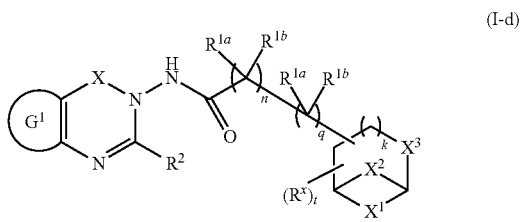

(I-d)

wherein $G^1$, $R^x$, $R^2$, $R^{1a}$, $R^{1b}$, X, $X^1$, $X_2$, $X_3$, k, n, q, and t are as described in the Summary and in the embodiments herein above and below.

In certain embodiments, J is O or S. In certain embodiments, J is O. In other embodiments, J is S.

T, when present, is attached to any substitutable atom of the ring $G^1$ and has values as described in the Summary and embodiments herein below.

For example, certain compounds include those wherein T is absent.

Yet certain compounds of formula include those wherein T, at each occurrence, is independently alkyl (e.g. $C_1$-$C_6$ alkyl such as, but not limited to, ethyl, methyl), halogen (e.g. F, Cl, Br), or haloalkyl (including but not limited thereto, trifluoromethyl).

In conjunction with any above or below embodiments, X is as described in the Summary and herein below. For example, certain groups of compounds of formula (I), (I-a)-(I-d) include those wherein X is C(O). Other group of compounds of formula (I), (I-a)-(I-d) include those wherein X is $S(O)_2$.

$R^{1a}$ and $R^{1b}$ have values as described in the Summary and embodiments herein.

In conjunction with any above or below embodiments, $R^{1a}$ and $R^{1b}$ for certain groups of compounds of formula (I), (I-a)-(I-d) are, for example, each independently hydrogen, alkyl such as, but not limited to, $C_1$-$C_4$ alkyl (e.g. methyl, ethyl, isopropyl), or haloalkyl (e.g. trifluoromethyl).

In conjunction with any above or below embodiments, $R^{1a}$ and $R^{1b}$ are, for example, each independently hydrogen or alkyl such as, but not limited to, $C_1$-$C_4$ alkyl (e.g. methyl, ethyl, isopropyl). In certain embodiments, $R^{1a}$ and $R^{1b}$ are, for example, each independently hydrogen or methyl.

In conjunction with any above or below embodiments, $R^{1a}$ and $R^{1b}$ are, for example, hydrogen.

n and q have values as described in the Summary and embodiments herein. It is appreciated that when q is 0 in formula (I), (I-a)-(I-c), then J is linked directly to the ring containing $X^1$, $X^2$, and $X^3$; and when q is 0 in formula (I-d), then $(CR^{1a}R^{1b})_n$ is linked directly to the ring containing $X^1$, $X^2$, and $X^3$.

In conjunction with any above or below embodiments, n is 1, and q is 0 or 1.

In conjunction with any above or below embodiments, n is 1 or 2, and q is 1 or 2.

In conjunction with any above or below embodiments, n is 1, q is 0 or 1, and J is absent.

In conjunction with any above or below embodiments, n is 1, q is 0, and J is absent.

In conjunction with any above or below embodiments, n is 1, q is 1, and J is absent.

In conjunction with any above or below embodiments, n is for 2, q is 1 or 2, and J is O or S.

In conjunction with any above or below embodiments, n is 1, q is 1, and J is O or S.

In conjunction with any above or below embodiments, n is 1, q is 1, and J is O.

In conjunction with any above or below embodiments, n is 1, q is 1, and J is S.

In conjunction with any above or below embodiments, n is 1, q is 2, and J is O or S.

In conjunction with any above or below embodiments, n is 1, q is 2, and J is O.

In conjunction with any above or below embodiments, n is 2, q is 1, and J is S.

k for compounds of formula (I), (I-a)-(I-d) is 0 or 1. In certain embodiments, k is 1. In other embodiments, k is 0. In embodiments wherein k is 0, $X^3$ is directly linked to the carbon atoms of the bicyclic ring.

In conjunction with any above or below embodiments, k is 1. Examples of the ring containing $X^1$, $X^2$, and $X^3$ when k is 1 include, but are not limited to:

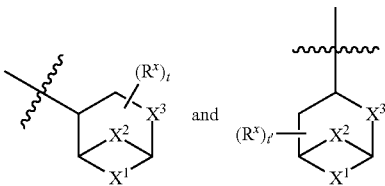

In conjunction with any above or below embodiments, k is 0. An example of a ring containing $X^1$, $X^2$, and $X^3$ when k is 0 includes, but is not limited to:

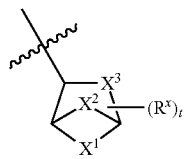

$X^1$, $X^2$, and $X^3$ for compounds of formula (I), (I-a)-(I-d) have values as described in the Summary and embodiments herein. In conjunction with any above or below embodiments, certain groups of compounds of formula (I), (I-a)-(I-d) include those wherein $X^1$, $X^2$, and $X^3$ are $CH_2$. In other embodiments, one of $X^1$, $X^2$, and $X^3$ is O, and the others are $CH_2$. In other embodiments, one of $X^1$, $X^2$, and $X^3$ is S, and the others are $CH_2$.

$R^x$ for compounds of formula (I), (I-a)-(I-d) are optional substituents of any substitutable atom of the ring containing $X^1$, $X^2$, and $X^3$, and have values as described in the Summary and embodiments herein. In conjunction with any above or below embodiments, each $R^x$, for example, is independently alkyl such as, but not limited to $C_1$-$C_4$ alkyl (e.g. methyl) or halogen (e.g. F, Cl).

$R^2$ for compounds of formula (I), (I-a)-(I-d) have values as described in the Summary and embodiments herein.

Certain embodiments are directed to a group of compounds of formula (I), (I-a)-(I-d) wherein $R^2$ is $G^{2a}$, hydrogen, alkyl (e.g. $C_1$-$C_4$ alkyl such as, but not limited to, methyl, ethyl, isopropyl), haloalkyl (e.g. 2,2,2-trifluoroethyl, trifluoromethyl), or $NR^{2d}R^{2e}$; wherein $G^{2a}$, $R^{2d}$, and $R^{2e}$ have values as described in the Summary and embodiments herein.

Certain embodiments are directed to a group of compounds of formula (I), (I-a)-(I-d) wherein $R^2$ is $G^{2a}$. $G^{2a}$ has values as described in the Summary and embodiments herein. In certain embodiments, $G^{2a}$ is cycloalkyl or heterocycle. In certain embodiments, $G^{2a}$ is cycloalkyl. In certain embodiments, $G^{2a}$ is heterocycle. In conjunction with any above or below embodiments, an example of said cycloalkyl includes, but is not limited to, monocyclic cycloalkyl (for example, cyclopropyl). In conjunction with any above or below embodiments, a non-limiting example of said heterocycle includes, but is not limited to, monocyclic heterocycle (e.g. morpholinyl, thiomorpholinyl). Each $G^{2a}$ (including the exemplary rings of $G^{2a}$) is optionally substituted as described in the Summary and herein. For example, each $G^{2a}$ (including the exemplary rings of $G^{2a}$) is optionally substituted with 1, 2, 3, or 4 substituents selected from the group consisting of alkyl such as, but not limited to, $C_1$-$C_4$ alkyl, halogen, and haloalkyl (e.g. trifluoromethyl).

Other embodiments are directed to a group of compounds of formula (I), (I-a)-(I-d) wherein $R^2$ is hydrogen, alkyl (e.g. $C_1$-$C_4$ alkyl such as, but not limited to, methyl, ethyl, isopropyl), or haloalkyl (e.g. 2,2,2-trifluoroethyl, trifluoromethyl).

Other embodiments are directed to a group of compounds of formula (I), (I-a)-(I-d) wherein $R^2$ is $NR^{2d}R^{2e}$; and $R^{2d}$ and $R^{2e}$ have values as described in the Summary and embodiments herein. For example, $R^{2d}$ is hydrogen or alkyl such as, but not limited to, $C_1$-$C_4$ alkyl (e.g. methyl, ethyl). $R^{2e}$, for example, is hydrogen, alkyl such as, but not limited to, $C_1$-$C_4$ alkyl (e.g. methyl, ethyl), -alkylenyl-$OR^a$, or -alkylenyl-N($R^{2f}$)($R^{2g}$) wherein $R^a$, $R^{2f}$, and $R^{2g}$ are as disclosed in the Summary and embodiments herein. In certain embodiments, $R^{2d}$ and $R^{2e}$ can be the same or different, and are each independently hydrogen or alkyl such as, but not limited to, $C_1$-$C_4$ alkyl (e.g. methyl, ethyl). In yet other embodiments, $R^{2d}$ is hydrogen or alkyl such as, but not limited to, $C_1$-$C_4$ alkyl (e.g. methyl, ethyl), and $R^{2e}$, for example, is -alkylenyl-$OR^a$ or -alkylenyl-N($R^{2f}$)($R^{2g}$) wherein $R^a$, $R^{2f}$, and $R^{2g}$ are as disclosed in the Summary and embodiments herein. In the embodiments wherein $R^{2e}$ is -alkylenyl-$OR^a$, $R^a$, for example, is alkyl such as, but not limited to, $C_1$-$C_4$ alkyl (e.g. methyl, ethyl). In the embodiments wherein $R^{2e}$ is -alkylenyl-N($R^{2f}$)($R^{2g}$), $R^{2f}$, for example, is hydrogen or alkyl such as, but not limited to, $C_1$-$C_4$ alkyl (e.g. methyl, ethyl), and $R^{2g}$ is, for example, $C(O)OR^c$ wherein $R^c$ is as disclosed in the Summary and embodiments herein. For example, in embodiments wherein $R^{2g}$ is $C(O)OR^c$, $R^c$, for example, is alkyl such as, but not limited to, $C_1$-$C_4$ alkyl (e.g. methyl, ethyl, tert-butyl).

It is appreciated that compounds of formula (I), (I-a)-(I-d) with combinations of the above embodiments, including particular, more particular and preferred embodiments are contemplated.

Accordingly, one aspect relates to a group of compounds of formula (I) or (I-d) wherein X is C(O) and $G^1$ is benzo or heteroaryl (e.g. monocyclic heteroaryl such as, but not limited to, thienyl); each of which is optionally substituted as described in the Summary and embodiments herein above.

Another aspect relates to a group of compounds of formula (I) or (I-d) wherein X is C(O), $G^1$ is benzo or heteroaryl (e.g. monocyclic heteroaryl such as, but not limited to, thienyl); each of which is optionally substituted as described in the Summary and embodiments herein above; $X^1$, $X^2$, and $X^3$ are $CH_2$.

Another aspect is directed to a group of compounds of formula (I) or (I-d) wherein X is C(O), $G^1$ is benzo or heteroaryl (e.g. monocyclic heteroaryl such as, but not limited to, thienyl); each of which is optionally substituted as described in the Summary and embodiments herein above; one of $X^1$, $X^2$, and $X^3$ is O or S, and the others are $CH_2$.

Another aspect is directed to a group of compounds of formula (I) or (I-d) wherein X is C(O), $G^1$ is benzo or heteroaryl (e.g. monocyclic heteroaryl such as, but not limited to, thienyl); each of which is optionally substituted as described in the Summary and embodiments herein above; one of $X^1$, $X^2$, and $X^3$ is O, and the others are $CH_2$.

Another aspect is directed to a group of compounds of formula (I) or (I-d) wherein X is C(O), $G^1$ is benzo or heteroaryl (e.g. monocyclic heteroaryl such as, but not limited to, thienyl); each of which is optionally substituted as described in the Summary and embodiments herein above; one of $X^1$, $X^2$, and $X^3$ is S, and the others are $CH_2$.

Another aspect relates to a group of compounds of formula (I) or (I-d) wherein X is C(O), $G^1$ is benzo, optionally substituted as described in the Summary and embodiments herein above; $X^1$, $X^2$, and $X^3$ are $CH_2$.

Another aspect is directed to a group of compounds of formula (I) or (I-d) wherein X is C(O), $G^1$ is benzo, optionally substituted as described in the Summary and embodiments herein above; one of $X^1$, $X^2$, and $X^3$ is O or S, and the others are $CH_2$.

Another aspect is directed to a group of compounds of formula (I) or (I-d) wherein X is C(O), $G^1$ is benzo, optionally substituted as described in the Summary and embodiments herein above; one of $X^1$, $X^2$, and $X^3$ is O, and the others are $CH_2$.

Another aspect is directed to a group of compounds of formula (I) or (I-d) wherein X is C(O), $G^1$ is benzo, optionally substituted as described in the Summary and embodiments herein above; one of $X^1$, $X^2$, and $X^3$ is S, and the others are $CH_2$.

Another aspect relates to a group of compounds of formula (I) or (I-d) wherein X is C(O), $G^1$ is heteroaryl (e.g. monocyclic heteroaryl such as, but not limited to, thienyl); optionally substituted as described in the Summary and embodiments herein above; $X^1$, $X^2$, and $X^3$ are $CH_2$.

Another aspect is directed to a group of compounds of formula (I) or (I-d) wherein X is C(O), $G^1$ is heteroaryl (e.g. monocyclic heteroaryl such as, but not limited to, thienyl); optionally substituted as described in the Summary and embodiments herein above; one of $X^1$, $X^2$, and $X^3$ is O or S, and the others are $CH_2$.

Another aspect is directed to a group of compounds of formula (I) or (I-d) wherein X is C(O), $G^1$ is heteroaryl (e.g. monocyclic heteroaryl such as, but not limited to, thienyl); optionally substituted as described in the Summary and embodiments herein above; one of $X^1$, $X^2$, and $X^3$ is O, and the others are $CH_2$.

Another aspect is directed to a group of compounds of formula (I) or (I-d) wherein X is C(O), $G^1$ is heteroaryl (e.g. monocyclic heteroaryl such as, but not limited to, thienyl); optionally substituted as described in the Summary and embodiments herein above; one of $X^1$, $X^2$, and $X^3$ is S, and the others are $CH_2$.

Another aspect relates to a group of compounds of formula (I-a)-(I-c) wherein X is C(O) and $X^1$, $X^2$, and $X^3$ are $CH_2$.

Another aspect is directed to a group of compounds of formula (I-a)-(I-c) wherein X is C(O); and one of $X^1$, $X^2$, and $X^3$ is O or S, and the others are $CH_2$.

Another aspect is directed to a group of compounds of formula (I-a)-(I-c) wherein X is C(O); and one of $X^1$, $X^2$, and $X^3$ is O, and the others are $CH_2$.

Another aspect is directed to a group of compounds of formula (I-a)-(I-c) wherein X is C(O); and one of $X^1$, $X^2$, and $X^3$ is S, and the others are $CH_2$.

Within each group of compounds described herein above, T, $R^2$, $R^{1a}$, $R^{1b}$, n, q, $R^x$, r, and t are as described in the Summary and embodiments herein above.

Thus, of each group of compounds of formula (I), (I-a)-(I-c) as described in each of the preceding paragraphs, examples of a subgroup include those wherein J is absent, O, or S.

Examples of yet another subgroup of compounds of formula (I), (I-a)-(I-c) include those wherein J is absent.

Examples of yet another subgroup of compounds of formula (I), (I-a)-(I-c) include those wherein J is O or S.

Examples of yet another subgroup of compounds of formula (I), (I-a)-(I-c) include those wherein J is O.

Examples of yet another subgroup of compounds of formula (I), (I-a)-(I-c) include those wherein J is S.

Examples of yet another subgroup of compounds of formula (I), (I-a)-(I-d) include those wherein $R^2$ is $G^{2a}$, hydrogen, alkyl (e.g. $C_1$-$C_4$ alkyl such as, but not limited to, methyl, ethyl, isopropyl), haloalkyl (e.g. 2,2,2-trifluoroethyl, trifluoromethyl), or $NR^{2d}R^{2e}$; wherein $G^{2a}$, $R^{2d}$, and $R^{2e}$ have values as described in the Summary and embodiments herein above.

Examples of yet another subgroup of compounds of formula (I), (I-a)-(I-d) include those wherein $R^2$ is $G^{2a}$, wherein $G^{2a}$ has values as described in the Summary and embodiments herein above.

Examples of yet another subgroup of compounds of formula (I), (I-a)-(I-d) include those wherein $R^2$ is hydrogen, alkyl (e.g. $C_1$-$C_4$ alkyl such as, but not limited to, methyl, ethyl, isopropyl), or haloalkyl (e.g. 2,2,2-trifluoroethyl, trifluoromethyl).

Examples of yet another subgroup of compounds of formula (I), (I-a)-(I-d) include those wherein $R^2$ is $NR^{2d}R^{2e}$; wherein $R^{2d}$ and $R^{2e}$ have values as described in the Summary and embodiments herein above.

Examples of yet another subgroup of compounds of formula (I), (I-a)-(I-c) include those wherein J is absent, O, or S, and $R^2$ is $G^{2a}$, hydrogen, alkyl (e.g. $C_1$-$C_4$ alkyl such as, but not limited to, methyl, ethyl, isopropyl), haloalkyl (e.g. 2,2,2-trifluoroethyl, trifluoromethyl), or $NR^{2d}R^{2e}$; wherein $G^{2a}$, $R^{2d}$, and $R^{2e}$ have values as described in the Summary and embodiments herein above.

Examples of yet another subgroup of compounds of formula (I), (I-a)-(I-c) include those wherein J is absent, and $R^2$ is $G^{2a}$, hydrogen, alkyl (e.g. $C_1$-$C_4$ alkyl such as, but not limited to, methyl, ethyl, isopropyl), haloalkyl (e.g. 2,2,2-trifluoroethyl, trifluoromethyl), or $NR^{2d}R^{2e}$; wherein $G^{2a}$, $R^{2d}$, and $R^{2e}$ have values as described in the Summary and embodiments herein above.

Examples of yet another subgroup of compounds of formula (I), (I-a)-(I-c) include those wherein J is O or S, and $R^2$ is $G^{2a}$, hydrogen, alkyl (e.g. $C_1$-$C_4$ alkyl such as, but not limited to, methyl, ethyl, isopropyl), haloalkyl (e.g. 2,2,2-trifluoroethyl, trifluoromethyl), or $NR^{2d}R^{2e}$; wherein $G^{2a}$, $R^{2d}$, and $R^{2e}$ have values as described in the Summary and embodiments herein above.

Examples of yet another subgroup of compounds of formula (I), (I-a)-(I-c) include those wherein J is O, and $R^2$ is $G^{2a}$, hydrogen, alkyl (e.g. $C_1$-$C_4$ alkyl such as, but not limited to, methyl, ethyl, isopropyl), haloalkyl (e.g. 2,2,2-trifluoroethyl, trifluoromethyl), or $NR^{2d}R^{2e}$; wherein $G^{2a}$, $R^{2d}$, and $R^{2e}$ have values as described in the Summary and embodiments herein above.

Examples of yet another subgroup of compounds of formula (I), (I-a)-(I-c) include those wherein J is S, and $R^2$ is $G^{2a}$, hydrogen, alkyl (e.g. $C_1$-$C_4$ alkyl such as, but not limited to, methyl, ethyl, isopropyl), haloalkyl (e.g. 2,2,2-trifluoroethyl, trifluoromethyl), or $NR^{2d}R^{2e}$; wherein $G^{2a}$, $R^{2d}$, and $R^{2e}$ have values as described in the Summary and embodiments herein above.

Examples of yet another subgroup of compounds of formula (I), (I-a)-(I-c) include those wherein J is absent, O, or S, and $R^2$ is $G^{2a}$, wherein $G^{2a}$ has values as described in the Summary and embodiments herein above.

Examples of yet another subgroup of compounds of formula (I), (I-a)-(I-c) include those wherein J is absent, and $R^2$ is $G^{2a}$, wherein $G^{2a}$ has values as described in the Summary and embodiments herein above.

Examples of yet another subgroup of compounds of formula (I), (I-a)-(I-c) include those wherein J is O or S, and $R^2$ is $G^{2a}$, wherein $G^{2a}$ has values as described in the Summary and embodiments herein above.

Examples of yet another subgroup of compounds of formula (I), (I-a)-(I-c) include those wherein J is O, and $R^2$ is $G^{2a}$, wherein $G^{2a}$ has values as described in the Summary and embodiments herein above.

Examples of yet another subgroup of compounds of formula (I), (I-a)-(I-c) include those wherein J is S, and $R^2$ is $G^{2a}$, wherein $G^{2a}$ has values as described in the Summary and embodiments herein above.

Examples of yet another subgroup of compounds of formula (I), (I-a)-(I-c) include those wherein J is absent, O, or S, and $R^2$ is hydrogen, alkyl (e.g. $C_1$-$C_4$ alkyl such as, but not limited to, methyl, ethyl, isopropyl), or haloalkyl (e.g. 2,2,2-trifluoroethyl, trifluoromethyl).

Examples of yet another subgroup of compounds of formula (I), (I-a)-(I-c) include those wherein J is absent, and $R^2$ is hydrogen, alkyl (e.g. $C_1$-$C_4$ alkyl such as, but not limited to, methyl, ethyl, isopropyl), or haloalkyl (e.g. 2,2,2-trifluoroethyl, trifluoromethyl).

Examples of yet another subgroup of compounds of formula (I), (I-a)-(I-c) include those wherein J is O or S, and $R^2$ is hydrogen, alkyl (e.g. $C_1$-$C_4$ alkyl such as, but not limited to, methyl, ethyl, isopropyl), or haloalkyl (e.g. 2,2,2-trifluoroethyl, trifluoromethyl).

Examples of yet another subgroup of compounds of formula (I), (I-a)-(I-c) include those wherein J is O, and $R^2$ is hydrogen, alkyl (e.g. $C_1$-$C_4$ alkyl such as, but not limited to, methyl, ethyl, isopropyl), or haloalkyl (e.g. 2,2,2-trifluoroethyl, trifluoromethyl).

Examples of yet another subgroup of compounds of formula (I), (I-a)-(I-c) include those wherein J is S, and $R^2$ is hydrogen, alkyl (e.g. $C_1$-$C_4$ alkyl such as, but not limited to, methyl, ethyl, isopropyl), or haloalkyl (e.g. 2,2,2-trifluoroethyl, trifluoromethyl).

Examples of yet another subgroup of compounds of formula (I), (I-a)-(I-c) include those wherein J is absent, O, or S, and $R^2$ is $NR^{2d}R^{2e}$; wherein $R^{2d}$ and $R^{2e}$ have values as described in the Summary and embodiments herein above.

Examples of yet another subgroup of compounds of formula (I), (I-a)-(I-c) include those wherein J is absent, and $R^2$ is $NR^{2d}R^{2e}$; wherein $R^{2d}$ and $R^{2e}$ have values as described in the Summary and embodiments herein above.

Examples of yet another subgroup of compounds of formula (I), (I-a)-(I-c) include those wherein J is O or S, and $R^2$ is $NR^{2d}R^{2e}$; wherein $R^{2d}$ and $R^{2e}$ have values as described in the Summary and embodiments herein above.

Examples of yet another subgroup of compounds of formula (I), (I-a)-(I-c) include those wherein J is O, and $R^2$ is $NR^{2d}R^{2e}$; wherein $R^{2d}$ and $R^{2e}$ have values as described in the Summary and embodiments herein above.

Examples of yet another subgroup of compounds of formula (I), (I-a)-(I-c) include those wherein J is S, and $R^2$ is $NR^{2d}R^{2e}$; wherein $R^{2d}$ and $R^{2e}$ have values as described in the Summary and embodiments herein above.

Exemplary compounds contemplated include, but are not limited to:

2-[(1S,2S,5S)-6,6-dimethylbicyclo[3.1.1]hept-2-yl]-N-[4-oxo-2-(propan-2-yl)quinazolin-3(4H)-yl]acetamide;

2-[(1S,2S,5S)-6,6-dimethylbicyclo[3.1.1]hept-2-yl]-N-(2-ethyl-4-oxoquinazolin-3(4H)-yl)acetamide;

N-(2-cyclopropyl-7-fluoro-4-oxoquinazolin-3(4H)-yl)-2-[(1S,2S,5S)-6,6-dimethylbicyclo[3.1.1]hept-2-yl]acetamide;

N-[2-cyclopropyl-4-oxo-7-(trifluoromethyl)quinazolin-3(4H)-yl]-2-[(1S,2S,5S)-6,6-dimethylbicyclo[3.1.1]hept-2-yl]acetamide;

N-(2-cyclopropyl-4-oxoquinazolin-3(4H)-yl)-2-[(1S,2S,5S)-6,6-dimethylbicyclo[3.1.1]hept-2-yl]acetamide;

2-[(1S,2S,5S)-6,6-dimethylbicyclo[3.1.1]hept-2-yl]-N-(2-ethyl-4-oxothieno[2,3-d]pyrimidin-3(4H)-yl)acetamide;

2-[(1S,2S,5S)-6,6-dimethylbicyclo[3.1.1]hept-2-yl]-N-[4-oxo-2-(trifluoromethyl)quinazolin-3(4H)-yl]acetamide;

2-[(1S,2R,5S)-(6,6-dimethylbicyclo[3.1.1]hept-2-yl)methoxy]-N-[4-oxo-2-(propan-2-yl)quinazolin-3(4H)-yl]acetamide;

2-({[(1S,2R,5S)-6,6-dimethylbicyclo[3.1.1]hept-2-yl]methyl}sulfanyl)-N-[4-oxo-2-(propan-2-yl)quinazolin-3(4H)-yl]propanamide;

2-{2-[(1S,2S,5S)-6,6-dimethylbicyclo[3.1.1]hept-2-yl]ethoxy}-N-[4-oxo-2-(propan-2-yl)quinazolin-3(4H)-yl]acetamide;

3-({[(1S,2R,5S)-6,6-dimethylbicyclo[3.1.1]hept-2-yl]methyl}sulfanyl)-N-[4-oxo-2-(propan-2-yl)quinazolin-3(4H)-yl]propanamide;

2-({[(1S,2R,5S)-6,6-dimethylbicyclo[3.1.1]hept-2-yl]methyl}sulfanyl)-N-[4-oxo-2-(propan-2-yl)quinazolin-3(4H)-yl]acetamide;

2-[(1S,2S,5S)-6,6-dimethylbicyclo[3.1.1]hept-2-yl]-N-[6-fluoro-4-oxo-2-(propan-2-yl)quinazolin-3(4H)-yl]acetamide;

2-[(1S,2S,5S)-6,6-dimethylbicyclo[3.1.1]hept-2-yl]-N-[4-oxo-2-(2,2,2-trifluoroethyl)quinazolin-3(4H)-yl]acetamide;

N-(2-cyclopropyl-4-oxothieno[2,3-d]pyrimidin-3(4H)-yl)-2-[(1S,2S,5S)-6,6-dimethylbicyclo[3.1.1]hept-2-yl]acetamide;

2-[(1S,2S,5S)-6,6-dimethylbicyclo[3.1.1]hept-2-yl]-N-(4-oxoquinazolin-3(4H)-yl)acetamide;

2-[(1S,2S,5S)-6,6-dimethylbicyclo[3.1.1]hept-2-yl]-N-(2-methyl-4-oxoquinazolin-3(4H)-yl)acetamide;

N-[6-chloro-4-oxo-2-(propan-2-yl)quinazolin-3(4H)-yl]-2-[(1S,2S,5S)-6,6-dimethylbicyclo[3.1.1]hept-2-yl]acetamide;

N-[2-(diethylamino)-4-oxoquinazolin-3(4H)-yl]-2-[(1S,2S,5S)-6,6-dimethylbicyclo[3.1.1]hept-2-yl]acetamide;

2-[(1S,2S,5S)-6,6-dimethylbicyclo[3.1.1]hept-2-yl]-N-[4-oxo-2-(propan-2-yl)thieno[2,3-d]pyrimidin-3(4H)-yl]acetamide;

2-[(1S,2R,5S)-6,6-dimethylbicyclo[3.1.1]hept-2-yl]-N-[4-oxo-2-(propan-2-yl)quinazolin-3(4H)-yl]acetamide;

(±)-2-(bicyclo[2.1.1]hex-2-yl)-N-[4-oxo-2-(propan-2-yl)quinazolin-3(4H)-yl]acetamide;

2-[(1R,3R,5S)-2-fluoro-6,6-dimethylbicyclo[3.1.1]hept-3-yl]-N-[4-oxo-2-(propan-2-yl)quinazolin-3(4H)-yl]acetamide;

2-[(1S,2S,3R,5R)-3-fluoro-6,6-dimethylbicyclo[3.1.1]hept-2-yl]-N-[4-oxo-2-(propan-2-yl)quinazolin-3(4H)-yl]acetamide; and 2-[(1R,3s,5S)-6,6-dimethylbicyclo[3.1.1]hept-3-yl]-N-[4-oxo-2-(propan-2-yl)quinazolin-3(4H)-yl]acetamide;

or pharmaceutically acceptable salts, solvates, or salts of solvates thereof.

Other compounds contemplated include, but not limited to, those shown below:

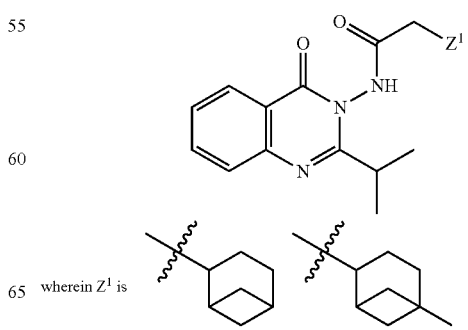

wherein $Z^1$ is

-continued

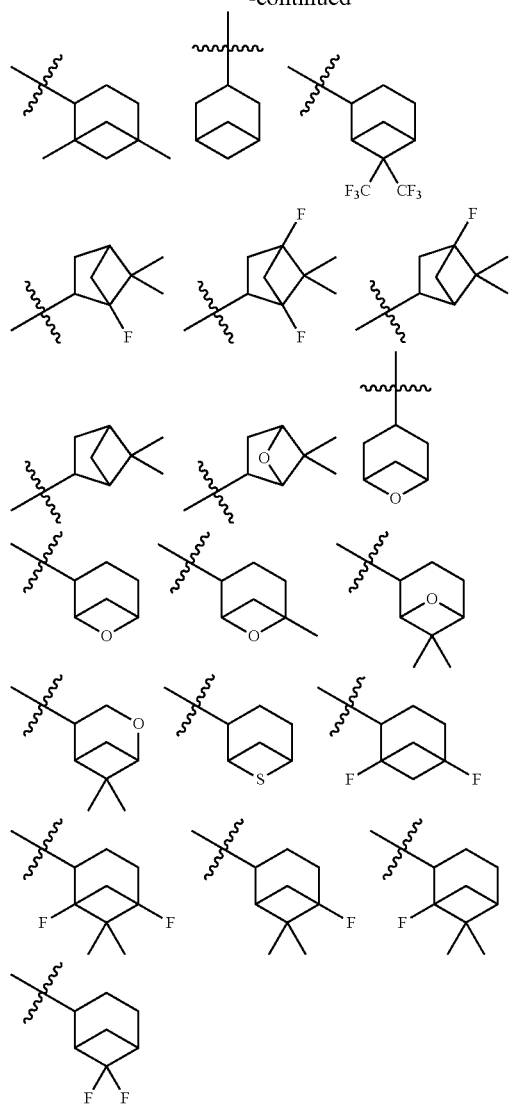

Compounds of the present application may exist as stereoisomers wherein, asymmetric or chiral centers are present. These stereoisomers are "R" or "S" depending on the configuration of substituents around the chiral carbon atom. The terms "R" and "S" used herein are configurations as defined in IUPAC 1974 Recommendations for Section E, Fundamental Stereochemistry, Pure Appl. Chem., 1976, 45: 13-30.

It will be appreciated that two or more asymmetric centers may be present in the present compounds, hence several diastereomers and enantiomers of the exemplified structures will often be possible, and that pure diastereomers and enantiomers represent preferred embodiments. It is intended that pure diastereomers, pure enantiomers, and mixtures thereof, are within the scope of the invention.

Various stereoisomers (including enantiomers and diastereomers) and mixtures thereof (including racemates) are contemplated. Individual stereoisomers of present compounds may be prepared synthetically from commercially available starting materials that contain asymmetric or chiral centers or by preparation of racemic mixtures followed by resolution of the individual stereoisomer using methods that are known to those of ordinary skill in the art. Examples of resolution are, for example, (i) attachment of a mixture of enantiomers to a chiral auxiliary, separation of the resulting mixture of diastereomers by recrystallization or chromatography, followed by liberation of the optically pure product; or (ii) separation of the mixture of enantiomers or diastereomers on chiral chromatographic columns.

Geometric isomers may exist in the present compounds. Thus various geometric isomers and mixtures thereof resulting from the disposition of substituents around a carbon-carbon double bond, a carbon-nitrogen double bond, a cycloalkyl group, or a heterocycle group are part of the invention. Substituents around a carbon-carbon double bond or a carbon-nitrogen bond are designated as Z or E configuration and substituents around a cycloalkyl or a heterocycle are designated as cis or trans configuration.

Within the present application it is to be understood that compounds disclosed herein may exhibit the phenomenon of tautomerism and all tautomeric isomers and mixtures thereof are included in the scope of the invention.

Though structural representations within this specification may show only one of the possible tautomeric or stereoisomeric forms, it is to be understood that the invention encompasses any tautomeric or stereoisomeric form, and mixtures thereof, and is not to be limited merely to any one tautomeric or stereoisomeric form utilized within drawings or the naming of the compounds.

Compounds described herein can exist in isotope-labeled or isotope-enriched form containing one or more atoms having an atomic mass or mass number different from the atomic mass or mass number most abundantly found in nature. Isotopes can be radioactive or non-radioactive isotopes. Isotopes of atoms such as hydrogen, carbon, phosphorous, sulfur, fluorine, chlorine, and iodine include, but are not limited to, $^{2}H$, $^{3}H$, $^{13}C$, $^{14}C$, $^{15}N$, $^{18}O$, $^{32}P$, $^{35}S$, $^{18}F$, $^{36}Cl$, and $^{125}I$. Compounds that contain other isotopes of these and/or other atoms are within the scope of this invention.

In another embodiment, the isotope-labeled compounds contain deuterium ($^{2}H$), tritium ($^{3}H$), or $^{14}C$ isotopes. Isotope-labeled compounds of this invention can be prepared by the general methods well known to persons having ordinary skill in the art. Such isotope-labeled compounds can be conveniently prepared by carrying out the procedures disclosed in the Examples and Schemes sections by substituting a readily available isotope-labeled reagent for a non-labeled reagent. In some instances, compounds may be treated with isotope-labeled reagents to exchange a normal atom with its isotope, for example, hydrogen for deuterium can be exchanged by the action of a deuteric acid such as $D_2SO_4$/$D_2O$. In addition to the above, relevant procedures and intermediates are disclosed, for instance, in Lizondo, J. et al., *Drugs Fut,* 21(11), 1116 (1996); Brickner, S. J., et al., *J Med Chem,* 39(3), 673 (1996); Mallesham, B. et al., *Org Lett,* 5(7), 963 (2003); PCT publications WO1997010223, WO2005099353, WO1995007271, WO2006008754; U.S. Pat. Nos. 7,538,189; 7,534,814; 7531685; 7528131; 7521421; 7514068; 7511013; and US Patent Application Publication Nos. 20090137457; 20090131485; 20090131363; 20090118238; 20090111840; 20090105338; 20090105307; 20090105147; 20090093422; 20090088416; and 20090082471, the methods are hereby incorporated by reference.

The isotope-labeled compounds of the invention may be used as standards to determine the effectiveness of KCNQ modulators in binding assays. Isotope containing compounds have been used in pharmaceutical research to investigate the in vivo metabolic fate of the compounds by evaluation of the mechanism of action and metabolic pathway of the nonisotope-labeled parent compound (Blake et al., *J. Pharm. Sci.,*

64, 3, 367-391 (1975)). Such metabolic studies are important in the design of safe, effective therapeutic drugs, either because the in vivo active compound administered to the patient or because the metabolites produced from the parent compound prove to be toxic or carcinogenic (Foster et al., Advances in Drug Research, Vol. 14, pp. 2-36, Academic press, London, 1985; Kato et al., J. *Labelled Comp. Radiopharmaceut.,* 36(10):927-932 (1995); Kushner et al., *Can. J. Physiol. Pharmacol.,* 77, 79-88 (1999)).

In addition, non-radioactive isotope-containing drugs, such as deuterated drugs called "heavy drugs," can be used for the treatment of diseases and conditions related to the activation of KCNQ channels. Increasing the amount of an isotope present in a compound above its natural abundance is called enrichment. Examples of the amount of enrichment include from about 0.5, 1, 2, 3, 4, 5, 6, 7, 8, 9, 10, 12, 16, 21, 25, 29, 33, 37, 42, 46, 50, 54, 58, 63, 67, 71, 75, 79, 84, 88, 92, 96, to about 100 mol %. Replacement of up to about 15% of normal atom with a heavy isotope has been effected and maintained for a period of days to weeks in mammals, including rodents and dogs, with minimal observed adverse effects (Czajka D. M. and Finkel A. J., Ann. N.Y. Acad. Sci., 1960, 84: 770; Thomson J. F., Ann. New York Acad. Sci., 1960, 84: 736; Czakja D. M. et al., Am. J. Physiol., 1961, 201: 357). Acute replacement of as high as 15%-23% in human fluids with deuterium was found not to cause toxicity (Blagojevic N. et al. in "Dosimetry & Treatment Planning for Neutron Capture Therapy"; Zamenhof R., Solares G., and Harling O. Eds. 1994. Advanced Medical Publishing, Madison Wis. pp. 125-134; Diabetes Metab. 23: 251 (1997)).

Stable isotope labeling of a drug may alter its physicochemical properties such as pKa and lipid solubility. These effects and alterations may affect the pharmacodynamic response of the drug molecule if the isotopic substitution affects a region involved in a ligand-receptor interaction. While some of the physical properties of a stable isotope-labeled molecule are different from those of the unlabeled one, the chemical and biological properties are the same, with one exception: because of the increased mass of the heavy isotope, any bond involving the heavy isotope and another atom will be stronger than the same bond between the light isotope and that atom. Accordingly, the incorporation of an isotope at a site of metabolism or enzymatic transformation will slow said reactions, potentially altering the pharmacokinetic profile or efficacy relative to the non-isotopic compound.

Examples of deuterated compounds of formula (I), (I-a)-(I-d) include, but not limited to, those wherein one or more hydrogen atoms of the ring containing $X^1$, $X^2$, and $X^3$ are replaced by deuterium.

c. Biological Data (i) In Vitro Assay:

The following example describes the assay that may be used to identify compounds that activate KCNQ2/3 channels.

HEK293 cells stably expressing human KCNQ2 and KCNQ3 subunits were seeded in 96-well, black-walled, clear-bottomed, poly-D-lysine coated plates (BD Biosciences, Bedford, Mass.) at a density of $1 \times 10^5$ cells per well 24 hours before the assay. On the assay day, BTC-AM dye (Invitrogen, Carlsbad, Calif.) was loaded into the cells by replacing the cell culture medium with 55 µL/well of 3 µg/ml dye in Dulbecco's Phosphate Buffered Saline (DPBS) (Invitrogen). Dye loading was allowed to proceed for 2 hours at room temperature and then cells were washed twice with 50 µL/well of assay buffer (in mM: 10 HEPES pH 7.3, 5 glucose, 140 Na-gluconate, 2.5 K-gluconate, 3.6 Ca-gluconate, 2 MgSO4, 0.1 Ouabain) to remove unloaded dye. Cells were incubated in 50 µL of assay buffer before loading onto a FLIPR system (Molecular Devices, Sunnyvale, Calif.). Various concentrations of compounds to be assayed were added to the cells in 50 µL of assay buffer and incubated for 4 minutes. The fluorescence signal was initiated by adding 100 µL of assay buffer containing 6 mM $TlNO_3$ and 10 mM $K_2SO_4$. Fluors were excited using the 488-nm line of an argon laser and emission was filtered using a 540±30 nm bandpass filter. Fluorescent signals were recorded for 3 minutes. Sums of the responses over basal responses were plotted versus concentrations of test compounds to obtain an $EC_{50}$ value and the points fit with a nonlinear regression curve using GraphPad Prism software (GraphPad Software Inc., San Diego, Calif.). $EC_{50}$ values were calculated from the resulting sigmoidal dose-response curves. The maximum response for each test compound was determined relative to the response produced by 10 µM retigabine. The maximum response of retigabine at 10 µM was set at 100%.

The following example describes the assay that may be used to identify compounds that activate KCNQ4 or KCNQ5 channels.

The assays were performed using a FLIPR$^{TETRA}$ (Molecular Devices, Sunnyvale, Calif.) in 384-well format. HEK293 cells stably expressing human KCNQ4 or KCNQ5 were seeded in 384-well, black-walled, clear-bottomed, poly-D-lysine coated plates (Greiner Bio-One, Germany) at a density of $1.5 \times 10^4$ cells per well, 24 hours before the assay. On the assay day, BTC-AM dye was loaded into the cells by replacing the cell culture medium with 30 µL/well of 2.8 µM dye in DPBS. Dye loading was allowed to proceed for 2 hours at room temperature and then cells were washed once in 30 µL/well of assay buffer (in mM: 10 HEPES pH 7.3, 5 glucose, 140 Na-gluconate, 2.5 K-gluconate, 3.6 Ca-gluconate, 2 $MgSO_4$, 0.1 Ouabain) to remove unloaded dye. Cells were incubated in 30 µL of assay buffer before loading onto a FLIPR$^{TETRA}$ system. Compounds to be assayed were added to the cells as 4× of final concentration in 15 µL of assay buffer and incubated for 4 minutes at room temperature. The influx signal was initiated by adding 15 µL of assay buffer containing 4.2 mM $TlNO_3$ and 7 mM $K_2SO_4$. $Tl^+$ influx signals were recorded for 3 minutes. $Tl^+$ influx signal was quantified as light unit changes after $Tl^+$ addition using the "SUM" statistic from the FLIPR$^{TETRA}$ software. Sums of the responses over basal responses were plotted versus concentrations of test compounds to obtain an $EC_{50}$ value and the points fit with a nonlinear regression curve using GraphPad Prism software (GraphPad Software Inc., San Diego, Calif.). $EC_{50}$ values were calculated from the resulting sigmoidal dose-response curves. The maximum response for each test compound was determined relative to the response produced by 10 µM retigabine. The maximum response of retigabine at 10 µM was set at 100%.

$EC_{50}$ values and the maximum response of compounds described herein assessed by the above-described assays are shown in Table 1 wherein A represents $EC_{50}$ of less than about 100 nM;

B represents $EC_{50}$ between about 100 nM to less than about 500 nM;

C represents $EC_{50}$ between about 500 nM to less than about 1000 nM;

D represents $EC_{50}$ between about 1000 nM to less than about 10,000 nM;

E represents $EC_{50}$ between about 10,000 nM to less than about 30,000 nM;

F represents $EC_{50}$ of about and greater than about 30,000 nM.

TABLE 1

| Example # | KCNQ2/3 EC$_{50}$ | Max. % | KCNQ4 EC$_{50}$ | Max. % | KCNQ5 EC$_{50}$ | Max. % |
|---|---|---|---|---|---|---|
| 1 | A | 103 | F | 22 | F | 164 |
| 2 | B | 109 | F | 22 | F | 294 |
| 3 | A | 99 | F | −2 | F | 36 |
| 4 | F | 3 | F | 1 | F | 12 |
| 5 | A | 93 | F | 6 | F | 50 |
| 6 | D | 99 | F | 5 | F | 9 |
| 7 | B | 58 | F | 6 | F | 52 |
| 8 | C | 132 | F | 57 | F | 52 |
| 9 | B | 49 | F | 23 | F | 49 |
| 10 | D | 121 | F | 122 | F | 335 |
| 11 | B | 123 | D | 293 | F | 714 |
| 12 | B | 149 | F | 41 | F | 136 |
| 13 | A | 73 | F | 8 | F | 21 |
| 14 | A | 105 | F | 27 | F | −10 |
| 15 | B | 149 | F | 21 | F | 210 |
| 16 | D | 144 | F | 6 | F | 13 |
| 17 | D | 97 | F | 3 | F | 14 |
| 18 | F | 8 | F | 4 | F | 19 |
| 19 | B | 28 | F | 8 | F | 5 |
| 20 | B | 111 | D | 46 | F | 10 |
| 21 | C | 121 | C | 25 | F | 14 |
| 22 | A | 179 | D | 255 | D | 857 |
| 23 | B | 155 | B | 229 | B | 633 |
| 24 | A | 25 | F | −43 | F | 88 |
| 25 | B | 93 | F | −23 | F | 15 |

(ii) In Vivo Data:

Animals

Adult male Sprague-Dawley rats (250-300 g body weight, Charles River Laboratories, Portage, Mich.) were used. Animal handling and experimental protocols were approved by the Institutional Animal Care and Use Committee (IACUC) at Abbott Laboratories. For all surgical procedures, animals were maintained under isoflurane anesthesia (4-5% to induce, 1-3% to maintain), and the incision sites were sterilized using a 10% povidone-iodine solution prior to and after surgeries.

Capsaicin-Induced Secondary Mechanical Hypersensitivity:

Rats were allowed to acclimate to the study room for 1 hour. They were then briefly restrained, and capsaicin was administered at 10 µg in 10 µl of vehicle (10% ethanol and 2-hydroxypropyl cyclodextrin) by intraplantar injection into the center of the right hind paw. Secondary mechanical hyperalgesia was measured at the heel away from the site of injection at 180 min following capsaicin (Joshi et al 2006, Neuroscience 143, 587-596). Compounds were injected (i.p.) 30 min before testing (150 min post-capsaicin).

Tactile (mechanical) allodynia was measured using calibrated von Frey filaments (Stoelting, Wood Dale, Ill.) as described in Chaplan, S. R., F. W. Bach, J. M. Pogrel, J. M. Chung and T. L. Yaksh, 1994, Quantitative assessment of tactile allodynia in the rat paw, J. Neurosci. Methods, 53, 55. Rats were placed into inverted individual plastic containers (20×12.5×20 cm) on top of a suspended wire mesh grid, and acclimated to the test chambers for 20 minutes. The von Frey filaments were presented perpendicularly to the plantar surface of the selected hind paw, and then held in this position for approximately 8 seconds with enough force to cause a slight bend in the filament. Positive responses include an abrupt withdrawal of the hind paw from the stimulus, or flinching behavior immediately following removal of the stimulus. A 50% withdrawal threshold was determined using an up-down procedure (Dixon, W. J., 1980, Efficient analysis of experimental observations, Ann. Rev. Pharmacol. Toxicol., 20, 441). Only rats with a baseline threshold score of less that 4.25 g were used in this study, and animals demonstrating motor deficit were excluded. Tactile allodynia thresholds were also assessed in several control groups, including naive, sham-operated, and saline infused animals as well as in the contralateral paws of nerve-injured rats. To evaluate the antinociceptive effects, animals were administered vehicle or test compound and tactile allodynia was assessed 30 minutes after i.p. administration.

Tactile allodynia was measured as described above. The compounds of Example 1, Example 2, and Example 5 showed a statistically significant change in paw withdrawal latency versus vehicle at about 30 mg/kg.

Chronic Constriction Injury (CCI) Model of Neuropathic Pain (Bennett Model)

A model of chronic constriction injury-induced (CCl) neuropathic pain was produced by following the method of Bennett and Xie (1988, Pain, 33, 87-107). The right common sciatic nerve was isolated at mid-thigh level, and loosely ligated by 4 chromic gut (5-0) ties separated by an interval of 1 mm. Sham rats underwent the same procedure, but without sciatic nerve constriction. All animals were left to recover for at least 2 weeks and no more than 5 weeks prior to testing of mechanical allodynia. Compounds were injected (i.p.) 30 minutes or more before testing. The compound of Example 1 showed a statistically significant change in paw withdrawal latency versus vehicle at about 30 mg/kg.

Spinal Nerve Ligation Model of Neuropathic Pain

A model of spinal nerve ligation-induced (SNL model) neuropathic pain as originally described by Kim and Chung (Kim, S. H. and J. M. Chung, 1992, Pain, 50, 355) was used to test compounds of the present application. The left L5 and L6 spinal nerves of the rat were isolated adjacent to the vertebral column and tightly ligated with a 5-0 silk suture distal to the DRG, and care taken to avoid injury of the L4 spinal nerve. Sham rats underwent the same procedure, but without nerve ligation. All animals were allowed to recover for at least one week and not more than three weeks prior to assessment of tactile allodynia. Compounds were injected (i.p.) 30 minutes or more before testing. The compounds of Example 1 and Example 15 showed a statistically significant change in paw withdrawal latency versus vehicle at about 30 mg/kg.

d. Methods of using the Compounds

In one aspect, the present invention provides methods of using one or more compounds or composition described herein to treat or prevent a disorder, disease, or condition of a subject (including human), which disorder, disease, or condition is responsive to modulation of KCNQ potassium channels. In particular, compounds described herein have utility in the treatment of a disorder, disease, or condition which is responsive to the modulation of KCNQ potassium channels.

In one group of embodiments, diseases and conditions of humans or other animals that can be treated with activation of KCNQ channels, include, but are not limited to, diseases and conditions involving abnormal neuronal excitability such as but not limited to epilepsy, pain, migraine, anxiety, overactive bladder, schizophrenia, anxiety, and substance abuse.

One embodiment provides methods for treating pain (for example, inflammatory pain, osteoarthritic pain, persistent pain, migraine pain, figromyalgia, chronic widespread pain, musculoskeletal pain, myofascial pain, temporomandibular joint (TMJ) pain, postoperative pain, cancer pain, neuropathic pain, or nociceptive pain) in mammals (including human) in need of such treatment. The methods comprise administering to the mammals therapeutically effective amounts of one or more compounds described herein, or pharmaceutically acceptable salts or solvates thereof. The methods further comprise administration of compounds described herein as a single dose. The methods also comprise repeated or chronic administration of present compounds over a period of days, weeks, months, or longer. In certain embodiments, the method comprises administering to the mammal therapeutically effective amounts of one or more of the compounds described herein, or pharmaceutically acceptable salts or solvates thereof, in combination with one or more analgesics (for example, acetaminophen or opioids such as, but not limited to, morphine), or with one or more nonsteroidal anti-inflammatory drug (NSAID); or administered with a combination of one or more analgesics and one or more NSAID. Examples of NSAIDs include, but are not limited to, aspirin, diclofenac, diflusinal, etodolac, fenbufen, fenoprofen, flufenisal, flurbiprofen, ibuprofen, indomethacin, ketoprofen, ketorolac, meclofenamic acid, mefenamic acid, meloxicam, nabumetone, naproxen, nimesulide, nitroflurbiprofen, olsalazine, oxaprozin, phenylbutazone, piroxicam, sulfasalazine, sulindac, tolmetin and zomepirac. In certain embodiments, the nonsteroidal anti-inflammatory drug (NSAID) is ibuprofen. In certain embodiments, the composition may optionally include one or more pharmaceutically acceptable carriers.

Actual dosage levels of active ingredients in the pharmaceutical compositions can be varied so as to obtain an amount of the active compound(s) that is effective to achieve the desired therapeutic response for a particular patient, compositions and mode of administration. The selected dosage level will depend upon the activity of the particular compound, the route of administration, the duration of treatment, the severity of the condition being treated and the condition and prior medical history of the patient being treated. However, it is within the skill of the art to start doses of the compound at levels lower than required to achieve the desired therapeutic effect and to gradually increase the dosage until the desired effect is achieved. In the treatment of certain medical conditions, repeated or chronic administration of the active ingredients may be required to achieve the desired therapeutic response. "Repeated or chronic administration" refers to the administration of the compositions described herein daily (i.e., every day) or intermittently (i.e., not every day) over a period of days, weeks, months, or longer. In particular, the treatment of chronic painful conditions is anticipated to require such repeated or chronic administration of the compositions described herein. Compounds of the invention may become more effective upon repeated or chronic administration such that the therapeutically effective doses on repeated or chronic administration may be lower than the therapeutically effective dose from a single administration.

Compounds can also be administered as a pharmaceutical composition comprising the compounds of interest in combination with one or more pharmaceutically acceptable carriers. The phrase "therapeutically effective amount" of the compound of the invention means a sufficient amount of the compound to treat disorders or, or to prevent development of or alleviate to some extent one or more of the symptoms of the condition or disorder being treated, at a reasonable benefit/risk ratio applicable to any medical treatment. It will be understood, however, that the total daily usage of the compounds and compositions of the invention will be decided by the attending physician within the scope of sound medical judgment. The specific therapeutically effective dose level for any particular patient will depend upon a variety of factors including the disorder being treated and the severity of the disorder; activity of the specific compound employed; the specific composition employed; the age, body weight, general health, sex, and diet of the patient; the time of administration, route of administration, and rate of excretion of the specific compound employed; the duration of the treatment; drugs used in combination or coincidental with the specific compound employed; and like factors well-known in the medical arts. For example, it is well within the skill of the art to start doses of the compound at levels lower than required to achieve the desired therapeutic effect and to gradually increase the dosage until the desired effect is achieved.

Compounds may be administered alone, or in combination (i.e. co-administered) with one or more additional pharmaceutical agents. For example, one or more present compounds or pharmaceutically acceptable salts or solvates thereof, may be administered in combination with one or more analgesics (e.g acetaminophen or opioids), or with one or more nonsteroidal anti-inflammatory drug (NSAID), or mixtures thereof. Non limiting examples of suitable NSAIDs include aspirin, diclofenac, diflusinal, etodolac, fenbufen, fenoprofen, flufenisal, flurbiprofen, ibuprofen, indomethacin, ketoprofen, ketorolac, meclofenamic acid, mefenamic acid, meloxicam, nabumetone, naproxen, nimesulide, nitroflurbiprofen, olsalazine, oxaprozin, phenylbutazone, piroxicam, sulfasalazine, sulindac, tolmetin and zomepirac. In certain embodiments, the nonsteroidal anti-inflammatory drug (NSAID) is ibuprofen. Combination therapy includes administration of a single pharmaceutical dosage formulation containing one or more of the compounds and one or more additional pharmaceutical agents, as well as administration of the compounds and each additional pharmaceutical agent in its own separate pharmaceutical dosage formulation. For example, one or more active ingredients (including present compounds and additional pharmaceutical agents) may be administered to the patient together, in a single oral dosage composition having a fixed ratio of each active ingredient, such as a tablet or capsule; or each active ingredient may be administered in separate oral dosage formulations.

Separate dosage formulations may be administered at essentially the same time (e.g., concurrently) or at separately staggered times (e.g., sequentially).

Therapeutically effective amounts can be determined by those skilled in the art, and will be adjusted to the requirements of each particular case. Generally, a therapeutically effective amount of a KCNQ modulator will range from a total daily dose, for example in human or other animals, of about 0.01 mg/kg body weight to about 100 mg/kg body weight, preferably of about 0.03 mg/kg body weight to about 30 mg/kg body weight. If desired, the effective daily dose can be divided into multiple doses for purposes of administration. Consequently, single dose compositions may contain such amounts or submultiples thereof to make up the daily dose. It is understood that the effective daily dose may vary with the duration of the treatment.

e. Pharmaceutical Compositions

Pharmaceutical compositions comprising compounds described herein or pharmaceutically acceptable salts or solvates thereof are also provided. The pharmaceutical compositions comprise compounds of interest formulated together with one or more non-toxic pharmaceutically acceptable carriers.

Another aspect relates to pharmaceutical compositions comprising compounds described herein, or pharmaceutically acceptable salts or solvates thereof, and one or more pharmaceutically acceptable carriers, alone or in combination with one or more analgesics (e.g. acetaminophen or opioids), or in combination with one or more nonsteroidal anti-inflammatory drug (NSAID), or a combination of one or more analgesics and one or more NSAID.

The pharmaceutical compositions can be administered to humans and other mammals orally, rectally, parenterally, intracisternally, intravaginally, intraperitoneally, topically (as by powders, ointments or drops), bucally or as an oral or nasal spray. The term "parenterally" as used herein, refers to modes of administration which include intravenous, intramuscular, intraperitoneal, intrasternal, subcutaneous, and intraarticular injection and infusion.

The term "pharmaceutically acceptable carrier" as used herein, means a non-toxic, inert solid, semi-solid or liquid filler, diluent, encapsulating material, or formulation auxiliary of any type. Some examples of materials which can serve as pharmaceutically acceptable carriers are sugars such as, but not limited to, lactose, glucose, and sucrose; starches such as, but not limited to, corn starch and potato starch; cellulose and its derivatives such as, but not limited to, sodium carboxymethyl cellulose, ethyl cellulose, and cellulose acetate; powdered tragacanth; malt; gelatin; talc; excipients such as, but not limited to, cocoa butter and suppository waxes; oils such as, but not limited to, peanut oil, cottonseed oil, safflower oil, sesame oil, olive oil, corn oil, and soybean oil; glycols; such as propylene glycol; esters such as, but not limited to, ethyl oleate and ethyl laurate; agar; buffering agents such as, but not limited to, magnesium hydroxide and aluminum hydroxide; alginic acid; pyrogen-free water; isotonic saline; Ringer's solution; ethyl alcohol, and phosphate buffer solutions, as well as other non-toxic compatible lubricants such as, but not limited to, sodium lauryl sulfate and magnesium stearate, as well as coloring agents, releasing agents, coating agents, sweetening, flavoring, and perfuming agents, preservatives and antioxidants can also be present in the composition, according to the judgment of the formulator.

Pharmaceutical compositions for parenteral injection comprise pharmaceutically acceptable sterile aqueous or non-aqueous solutions, dispersions, suspensions, or emulsions as well as sterile powders for reconstitution into sterile injectable solutions or dispersions just prior to use. Examples of suitable aqueous and nonaqueous carriers, diluents, solvents, or vehicles include water, ethanol, polyols (such as glycerol, propylene glycol, polyethylene glycol and the like), vegetable oils (such as olive oil), injectable organic esters (such as ethyl oleate) and suitable mixtures thereof. Proper fluidity can be maintained, for example, by the use of coating materials such as lecithin, by the maintenance of the required particle size in the case of dispersions and by the use of surfactants.

These compositions may also contain adjuvants such as preservatives, wetting agents, emulsifying agents, and dispersing agents. Prevention of the action of microorganisms can be ensured by the inclusion of various antibacterial and antifungal agents, for example, paraben, chlorobutanol, phenol sorbic acid and the like. It may also be desirable to include isotonic agents such as sugars, sodium chloride and the like. Prolonged absorption of the injectable pharmaceutical form can be brought about by the inclusion of agents which delay absorption such as aluminum monostearate and gelatin.

In some cases, in order to prolong the effect of the drug, it is desirable to slow the absorption of the drug from subcutaneous or intramuscular injection. This can be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions which are compatible with body tissues.

The injectable formulations can be sterilized, for example, by filtration through a bacterial-retaining filter or by incorporating sterilizing agents in the form of sterile solid compositions which can be dissolved or dispersed in sterile water or other sterile injectable medium just prior to use.

Solid dosage forms for oral administration include capsules, tablets, pills, powders and granules. In such solid dosage forms, the active compound may be mixed with at least one inert, pharmaceutically acceptable excipient or carrier, such as sodium citrate or dicalcium phosphate and/or a) fillers or extenders such as starches, lactose, sucrose, glucose, mannitol and silicic acid; b) binders such as carboxymethylcellulose, alginates, gelatin, polyvinylpyrrolidone, sucrose and acacia; c) humectants such as glycerol; d) disintegrating agents such as agar-agar, calcium carbonate, potato or tapioca starch, alginic acid, certain silicates and sodium carbonate; e) solution retarding agents such as paraffin; f) absorption accelerators such as quaternary ammonium compounds; g) wetting agents such as cetyl alcohol and glycerol monostearate; h) absorbents such as kaolin and bentonite clay and i) lubricants such as talc, calcium stearate, magnesium stearate, solid polyethylene glycols, sodium lauryl sulfate and mixtures thereof. In the case of capsules, tablets and pills, the dosage form may also comprise buffering agents.

Solid compositions of a similar type may also be employed as fillers in soft and hard-filled gelatin capsules using such carriers as lactose or milk sugar as well as high molecular weight polyethylene glycols and the like.

The solid dosage forms of tablets, dragees, capsules, pills and granules can be prepared with coatings and shells such as enteric coatings and other coatings well-known in the pharmaceutical formulating art. They may optionally contain opacifying agents and may also be of a composition such that they release the active ingredient(s) only, or preferentially, in a certain part of the intestinal tract, optionally, in a delayed manner. Examples of embedding compositions which can be used include polymeric substances and waxes.

The active compounds can also be in micro-encapsulated form, if appropriate, with one or more of the above-mentioned carriers.

Liquid dosage forms for oral administration include pharmaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor and sesame oils), glycerol, tetrahydrofurfuryl alcohol, polyethylene glycols and fatty acid esters of sorbitan and mixtures thereof.

Besides inert diluents, the oral compositions may also include adjuvants such as wetting agents, emulsifying, and suspending agents, sweetening, flavoring and perfuming agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar, tragacanth and mixtures thereof Compositions for rectal or vaginal administration are preferably suppositories which can be prepared by mixing the compounds of this invention with suitable non-irritating carriers or carriers such as cocoa butter, polyethylene glycol or a suppository wax which are solid at room temperature but liquid at body temperature and therefore melt in the rectum or vaginal cavity and release the active compound.

Present compounds can also be administered in the form of liposomes. As is known in the art, liposomes are generally derived from phospholipids or other lipid substances. Liposomes are formed by mono- or multi-lamellar hydrated liquid crystals which are dispersed in an aqueous medium. Any non-toxic, physiologically acceptable and metabolizable lipid capable of forming liposomes can be used. The present compositions in liposome form can contain, in addition to a compound of the present invention, stabilizers, preservatives, excipients and the like. The preferred lipids are natural and synthetic phospholipids and phosphatidyl cholines (lecithins) used separately or together.

Methods to form liposomes are known in the art. See, for example, Prescott, Ed., Methods in Cell Biology, Volume XIV, Academic Press, New York, N.Y. (1976), p. 33 et seq.

Dosage forms for topical administration include powders, sprays, ointments and inhalants. The active compound may be mixed under sterile conditions with a pharmaceutically acceptable carrier and any needed preservatives, buffers or propellants which may be required. Opthalmic formulations, eye ointments, powders and solutions are also contemplated as being within the scope of this invention.

Compounds described herein can be used in the form of pharmaceutically acceptable salts derived from inorganic or organic acids. The phrase "pharmaceutically acceptable salt" means those salts which are, within the scope of sound medical judgment, suitable for use in contact with the tissues of humans and lower animals without undue toxicity, irritation, allergic response and the like and are commensurate with a reasonable benefit/risk ratio.

Pharmaceutically acceptable salts are well known in the art. For example, S. M. Berge et al. describe pharmaceutically acceptable salts in detail in (J. Pharmaceutical Sciences, 1977, 66: 1 et seq). The salts can be prepared in situ during the final isolation and purification of the compounds of the invention or separately by reacting a free base function with a suitable organic acid. Representative acid addition salts include, but are not limited to acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, fumarate, hydrochloride, hydrobromide, hydroiodide, 2-hydroxyethansulfonate (isothionate), lactate, malate, maleate, methanesulfonate, nicotinate, 2-naphthalenesulfonate, oxalate, palmitoate, pectinate, persulfate, 3-phenylpropionate, picrate, pivalate, propionate, succinate, tartrate, thiocyanate, phosphate, glutamate, bicarbonate, p-toluenesulfonate and undecanoate. Also, the basic nitrogen-containing groups can be quaternized with such agents as lower alkyl halides such as, but not limited to, methyl, ethyl, propyl, and butyl chlorides, bromides and iodides; dialkyl sulfates like dimethyl, diethyl, dibutyl and diamyl sulfates; long chain halides such as, but not limited to, decyl, lauryl, myristyl and stearyl chlorides, bromides and iodides; arylalkyl halides like benzyl and phenethyl bromides and others. Water or oil-soluble or dispersible products are thereby obtained. Examples of acids which can be employed to form pharmaceutically acceptable acid addition salts include such inorganic acids as hydrochloric acid, hydrobromic acid, sulfuric acid, and phosphoric acid and such organic acids as acetic acid, fumaric acid, maleic acid, 4-methylbenzenesulfonic acid, succinic acid and citric acid.

Basic addition salts can be prepared in situ during the final isolation and purification of compounds of this invention by reacting a carboxylic acid-containing moiety with a suitable base such as, but not limited to, the hydroxide, carbonate or bicarbonate of a pharmaceutically acceptable metal cation or with ammonia or an organic primary, secondary or tertiary amine. Pharmaceutically acceptable salts include, but are not limited to, cations based on alkali metals or alkaline earth metals such as, but not limited to, lithium, sodium, potassium, calcium, magnesium and aluminum salts and the like and nontoxic quaternary ammonia and amine cations including ammonium, tetramethylammonium, tetraethylammonium, methylamine, dimethylamine, trimethylamine, triethylamine, diethylamine, ethylamine and the like. Other representative organic amines useful for the formation of base addition salts include ethylenediamine, ethanolamine, diethanolamine, piperidine, piperazine and the like.

The term "pharmaceutically acceptable prodrug" or "prodrug" as used herein, represents those prodrugs of the compounds of the present invention which are, within the scope of sound medical judgment, suitable for use in contact with the tissues of humans and lower animals without undue toxicity, irritation, allergic response, and the like, commensurate with a reasonable benefit/risk ratio, and effective for their intended use.

Contemplated also are compounds formed by synthetic means or formed by in vivo biotransformation of a prodrug.

Compounds described herein can exist in unsolvated as well as solvated forms, including hydrated forms, such as hemi-hydrates. In general, the solvated forms, with pharmaceutically acceptable solvents such as water and ethanol among others are equivalent to the unsolvated forms.

f. General Synthesis

Compounds described herein when prepared by synthetic processes or by metabolic processes are encompassed in this application. Preparation of the compounds by metabolic processes includes those occurring in the human or animal body (in vivo) or processes occurring in vitro.

Compounds described herein can be prepared using readily available starting materials or known intermediates. The compounds and the intermediates can be prepared by a variety of processes well known for the preparation of compounds of this class. For example, the compounds of formula (I) wherein the groups X, $X^1$, $X^2$, $X^3$, $R^x$, $R^{1a}$, $R^{1b}$, $R^2$, $R^{2d}$, $R^{2e}$, $G^1$, J, n, q, k, and t have the meanings as set forth in the summary section unless otherwise noted, can be synthesized as provided in Schemes 1-5.

Abbreviations which have been used in the descriptions of the Schemes and the Examples that follow are: DMSO-$d_6$ for deuterated dimethyl sulfoxide, EtOAc for ethyl acetate, EtOH for ethanol, THF for tetrahydrofuran, MeOH for methanol, and DMF for N,N-dimethylformamide.

Compounds of general formula (I) can be prepared, for example, using the general method outlined in Scheme 1.

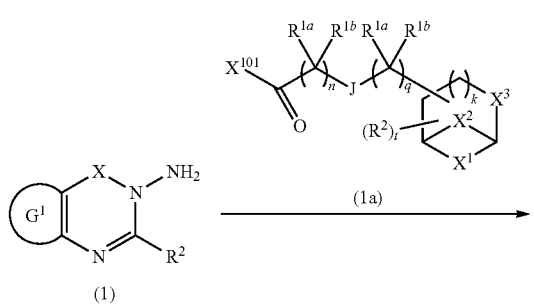

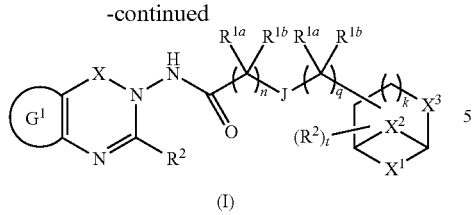

(I)

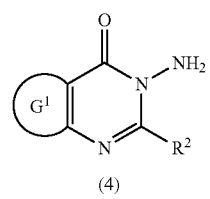

(4)

Compounds of formula (1) containing an amine group when treated with compounds of formula (1a) wherein $X^{101}$ is chloro, bromo, or OH under coupling conditions known to one skilled in the art, can provide compounds of general formula (I). Typical conditions for the reaction of (1) with compounds of formula (1a), wherein $X^{101}$ is chloro or bromo include, but are not limited to, stirring about an equimolar mixture of the compounds in a solvent such as, but not limited to, chloroform, dichloromethane, THF, or mixture thereof, optionally in the presence of a base such as, but not limited to, diisopropylethylamine or pyridine, at about 0° C. to about 30° C. for about 1-30 hours. Acid coupling conditions for compounds of formula (1a) wherein $X^{101}$ is —OH and compounds of formula (1), include stirring about an equimolar mixture of the compounds in a solvent such as, but not limited to, THF, N,N-dimethylacetamide, N,N-dimethylformamide, ethyl acetate, pyridine, chloroform, or mixtures thereof, with a coupling reagent, optionally along with a coupling auxiliary, and in the presence or absence of a base. Typical reactions can be carried out at temperatures ranging from about 0° C. to about 80° C., or may be carried out in a microwave reactor to facilitate the coupling. Examples of coupling reagents include, but are not limited to, bis(2-oxo-3-oxazolidinyl)phosphinic chloride (BOPCl), 1,3-dicyclohexylcarbodiimide (DCC), polymer supported 1,3-dicyclohexylcarbodiimide (PS-DCC), O-(7-azabenzotriazol-1-yl)-N,N,N',N'-tetramethyluronium hexafluorophosphate (HATU), O-benzotriazol-1-yl-N,N,N',N'-tetramethyluronium tetrafluoroborate (TBTU), and 1-propanephosphonic acid cyclic anhydride. Non limiting examples of a coupling auxiliary include 1-hydroxy-7-azabenzotriazole (HOAT) and 1-hydroxybenzotriazole hydrate (HOBT). Suitable examples of bases include, but are not limited to, N-methyl morpholine, triethylamine, and diisopropylethylamine.

Certain intermediate compounds of formula (1) wherein X is CO are represented by formula (4). Compounds of general formula (4) can be prepared using the two-step method outlined in Scheme 2.

Compounds of formula (2) or the esters thereof can be converted to compounds of formula (3) by treatment with compounds of formula $R^2COX^{102}$, wherein $X^{102}$ is chloro or bromo, and a base in a suitable solvent at about 0° C. to about 30° C., for about 0.5 to about 24 hours, followed by treatment with acetic anhydride and heating at reflux for 12 to 24 hours in order to effect cyclization. Typical examples of bases include but are not limited to, triethylamine, diisopropylethylamine, and pyridine. Examples of suitable solvents include, but are not limited to, chloroform, dichloromethane, THF, and mixtures thereof. Compounds of formula (3) can be converted to compounds of formula (4) by reaction with hydrazine at about room temperature for about 0.5 hour to about 24 hours, followed by heating in a solvent such as, but not limited to, toluene at reflux with removal of water (Dean-Stark apparatus).

Alternatively, compounds of formula (2) or the esters thereof can be converted to compounds of formula (3a) by treatment with compounds of formula $R^2COX^{102}$, wherein $X^{102}$ is chloro or bromo, and a base in a suitable solvent at about 0° C. to about 70° C., for about 0.5 to about 24 hours. Examples of suitable base include, but are not limited to, pyridine, triethylamine, and diisopropylethylamine. Examples of suitable solvents include, but are not limited to, chloroform, dichloromethane, THF, and mixtures thereof. Compounds of formula (3a) can be converted to compounds of formula (4) by treating with hydrazine hydrate in a suitable solvent such as, but not limited to, n-butanol and tetrahydrofuran at temperature ranging from about 50° C. to about 100° C.

Certain compounds of formula (I) wherein X is CO are represented by formula (7). Compounds of general formula (7) can be prepared using the two-step method outlined in Scheme 3.

Scheme 2

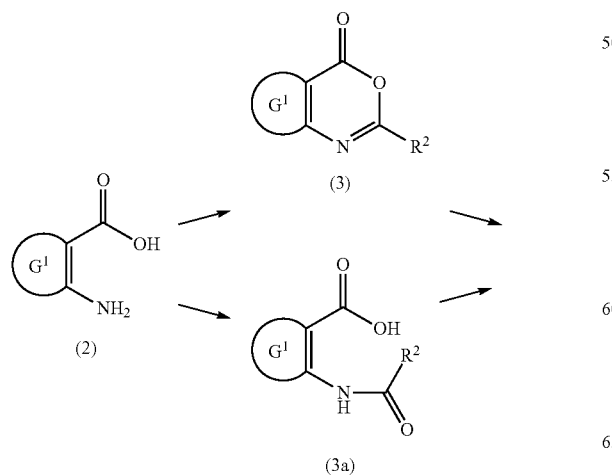

Scheme 3

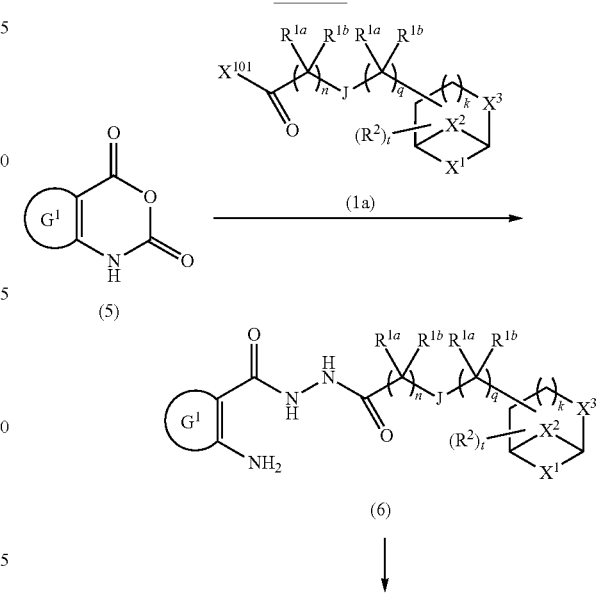

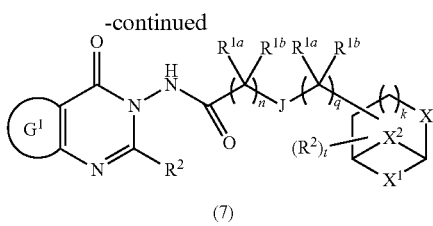

(7)

Compounds of formula (5) can be converted to compounds of formula (6) by reaction with an acylhydrazide of formula (1a) wherein $X^{101}$ is $NHNH_2$, in a solvent such as benzene, toluene, xylene, ethanol, or the like, at temperatures from about room temperature to about reflux of the chosen solvent and optionally with either added base (e.g., triethylamine) or acid (e.g., acetic acid). Alternatively, the reaction may be conducted in acetic acid as the reaction solvent at temperatures around 25-50° C. Compounds of formula (6) can be converted to compounds of formula (7) by reaction with an acid $R^2CO_2H$ such as formic acid ($R^2$=H), acetic acid ($R^2$=methyl), and the like, with or without heating; by reaction with an orthoester $R^2C(OEt)_3$ or $R^2C(OMe)_3$ in the presence of an acid such as hydrochloric acid or para-toluenesulfonic acid and heating in a suitable solvent such as dioxane or toluene; by reaction with an acid chloride $R^2COCl$ in the presence of a base such as, but not limited to, pyridine, in a solvent such as, but not limited to, dioxane, and at temperatures from about room temperature to about 100° C.; or by reaction with phosgene or a phosgene equivalent where $R^2$=OH in compounds of formula (7).

Certain compounds of formula (I) wherein X is $SO_2$ are represented by formula (10). Compounds of general formula (10) can be prepared using the general method outlined in Scheme 4.

Scheme 4

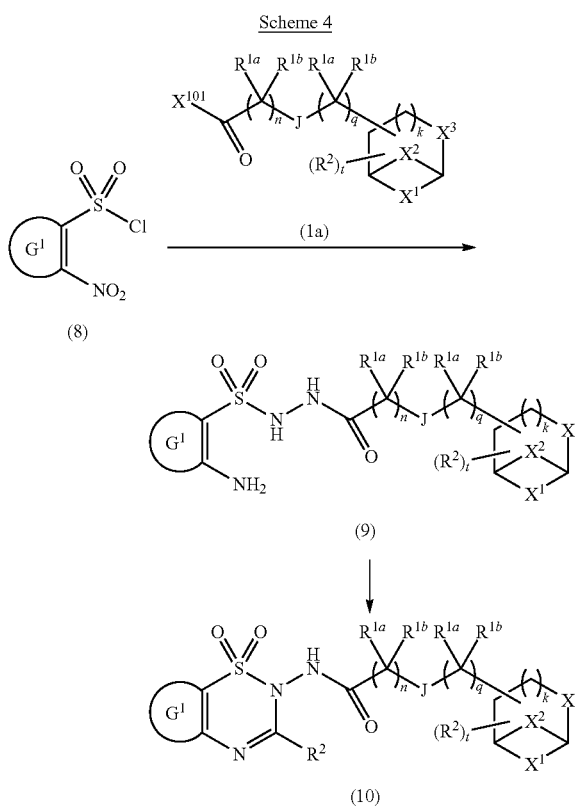

Compounds of formula (8) can be converted to compounds of formula (9) in two steps as follows: (1) reaction with an acylhydrazide of formula (1a) wherein $X^{101}$ is $NHNH_2$, in a solvent such as benzene, toluene, tetrahydrofuran, dimethylformamide or the like, at temperatures from about room temperature to reflux of the chosen solvent and optionally with added base (e.g., triethylamine, pyridine); and (2) reduction of the nitro group to the amino group using reaction conditions known to those skilled in the art, for example, catalytic hydrogenation of the intermediate from step (1) over a palladium-based or platinum-based catalyst in a solvent such as, but not limited to, methanol or ethyl acetate. Compounds of formula (9) can be converted to compounds of formula (10) using conditions from among those illustrated above for the conversion of (6) to (7).

Certain intermediate compounds of formula (1) wherein $R^2$ is $NR^{2d}R^{2e}$ are represented by formula (13). Compounds of general formula (13) can be prepared using the general method outlined in Scheme 5.

Scheme 5

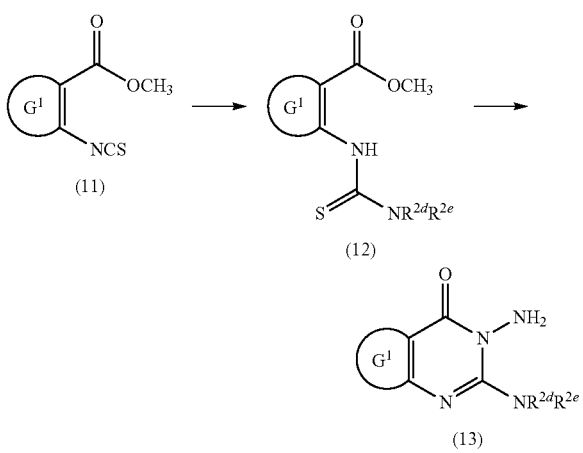

Compounds of formula (11) can be converted to compounds of formula (12) by reaction with a suitable amine of formula $HNR^{2d}R^{2e}$ in a solvent such as dichloromethane, tetrahydrofuran, or chloroform at about room temperature to about 50° C. Compounds of formula (12) can be converted to compounds of formula (13) by reaction first with iodomethane in a solvent such as, but not limited to, methanol, tetrahydrofuran, or dimethylformamide, at about room temperature to about 100° C., followed by reaction with hydrazine to form the cyclic product (13).

It will be appreciated that the synthetic schemes and specific examples as illustrated in the Examples section are illustrative and are not to be read as limiting the scope of the invention as it is defined in the appended claims. All alternatives, modifications, and equivalents of the synthetic methods and specific examples are included within the scope of the claims.

Optimum reaction conditions and reaction times for each individual step may vary depending on the particular reactants employed and substituents present in the reactants used. Unless otherwise specified, solvents, temperatures and other reaction conditions may be readily selected by one of ordinary skill in the art. Specific procedures are provided in the Examples section. Reactions may be worked up in the conventional manner, e.g. by eliminating the solvent from the residue and further purified according to methodologies generally known in the art such as, but not limited to, crystallization, distillation, extraction, trituration and chromatography. Unless otherwise described, the starting materials and reagents are either commercially available or may be prepared by one skilled in the art from commercially available materials using methods described in the chemical literature.

Routine experimentations, including appropriate manipulation of the reaction conditions, reagents and sequence of the synthetic route, protection of any chemical functionality that may not be compatible with the reaction conditions, and deprotection at a suitable point in the reaction sequence of the method are included in the scope of the invention. Suitable protecting groups and the methods for protecting and deprotecting different substituents using such suitable protecting groups are well known to those skilled in the art; examples of which may be found in T. Greene and P. Wuts, Protecting Groups in Chemical Synthesis ($3^{rd}$ ed.), John Wiley & Sons, NY (1999), which is incorporated herein by reference in its entirety. Synthesis of the compounds of the invention may be accomplished by methods analogous to those described in the synthetic schemes described hereinabove and in specific examples.

Starting materials, if not commercially available, may be prepared by procedures selected from standard organic chemical techniques, techniques that are analogous to the synthesis of known, structurally similar compounds, or techniques that are analogous to the above described schemes or the procedures described in the synthetic examples section.

When an optically active form of a compound of the invention is required, it may be obtained by carrying out one of the procedures described herein using an optically active starting material (prepared, for example, by asymmetric induction of a suitable reaction step), or by resolution of a mixture of the stereoisomers of the compound or intermediates using a standard procedure (such as chromatographic separation, recrystallization or enzymatic resolution).

Similarly, when a pure geometric isomer of a compound of the invention is required, it may be obtained by carrying out one of the above procedures using a pure geometric isomer as a starting material, or by resolution of a mixture of the geometric isomers of the compound or intermediates using a standard procedure such as chromatographic separation.

Following Examples may be used for illustrative purposes and should not be deemed to narrow the scope of the invention.

All experiments were conducted at room temperature unless otherwise stated.

g. EXAMPLES

Example 1

2-[(1S,2S,5S)-6,6-dimethylbicyclo[3.1.1]hept-2-yl]-N-[4-oxo-2-(propan-2-yl)quinazolin-3(4H)-yl]acetamide

Example 1A 2-((1S,2S,5S)-6,6-dimethylbicyclo[3.1.1]heptan-2-yl)ethanol (−)-Nopol (Aldrich) (66.4 g 0.40 mmol) was dissolved in ethyl acetate (500 mL). $PtO_2$ (2.0 g) was added under $N_2$ atmosphere. The mixture was hydrogenated at 41 psi. Uptake was completed within 2.5 hours. The mixture was filtered, washed with ethyl acetate and concentrated. The residue was distilled at 125-130° C./9.5 mm of Hg. to afford 61.5 g of the title compound.

Example 1B 2-((1S,2S,5S)-6,6-dimethylbicyclo[3.1.1]heptan-2-yl)acetic acid

A solution of chromium trioxide (42.6 g $CrO_3$, 426 mmol) in water (40 mL) was diluted with acetic acid (350 mL). The solution was cooled to 15° C. and Example 1A (27 g, 160 mmol) was added drop wise. The solution was left standing at room temperature overnight. Ethanol (20 mL) was added to destroy the excess $CrO_3$. The mixture was heated at 50° C. for 15 minutes and then concentrated under reduced pressure. The residue was suspended in water, acidified to pH 2 and extracted 3 times with ether. The ethereal solution was concentrated and the residue was dissolved in hexanes or petroleum ether. The organic solution is decanted from the green tar and concentrated under reduced pressure. The residue was dissolved in 10% aqueous NaOH and neutral impurities were extracted with ether (discarded). The aqueous phase was acidified to pH 2 and extracted with hexanes or petroleum ether, dried with $Na_2SO_4$, filtered, concentrated, cooled, and filtered to give 10.9 g of the title compound (crystals; melting point 50-53° C.).

Example 1C 2-((1S,2S,5S)-6,6-dimethylbicyclo[3.1.1]heptan-2-yl)acetyl chloride To a mixture of Example 1B (300 mg, 1.65 mmol) and thionyl chloride (901 μL, 12.4 mmol) was added a drop of dimethylformamide. The reaction was stirred at about 22° C. for 2 hours. The excess thionyl chloride was evaporated and the residue was dried under vacuum to afford the title compound.

Example 1D

2-[(1S,2S,5S)-6,6-dimethylbicyclo[3.1.1]hept-2-yl]-N-(2-isopropyl-4-oxoquinazolin-3(4H)-yl)acetamide To a mixture of 3-amino-2-isopropylquinazolin-4(3H)-one (Aldrich) (500 mg, 2.46 mmol) and Example 1C (494 mg, 2.46 mmol) in chloroform (12 mL) was added pyridine (0.30 mL, 3.69 mmol). The reaction was stirred at about room temperature for 12 hours. The reaction was diluted with $CH_2Cl_2$, washed with aqueous $NaHCO_3$, brine, dried over sodium sulfate, filtered, and concentrated. The residue was purified by flash chromatography on $SiO_2$ (eluted with hexanes-ethyl acetate, 0 to 50%) to give the title compound. $^1$H NMR (300 MHz, CDCl$_3$) δ ppm 1.00 (dd, J=9.8, 2.03 Hz, 1H) 1.09 (s, 3H) 1.24 (d, J=4.4 Hz, 3H) 1.30 (d, J=5.4 Hz, 3H) 1.35 (d, J=6.8 Hz, 3H) 1.86-2.05 (m, 4H) 2.07-2.25 (m, 1H) 2.32-2.44 (m, 1H) 2.53-2.63 (m, 2H) 2.64-2.79 (m, 1H) 3.10-3.26 (m, 1H) 7.43 (t, J=7.3 Hz, 1H) 8.21 (d, J=8.8 Hz, 1H). MS (ESI$^+$) m/z 368 (M+H)$^+$.

Example 2

2-[(1S,2S,5S)-6,6-dimethylbicyclo[3.1.1]hept-2-yl]-N-(2-ethyl-4-oxoquinazolin-3(4H)-yl)acetamide The product from Example 1C and 3-amino-2-ethylquinazolin-4(3H)-one (Aldrich) were processed using method analogous to that described in Example 1D to afford the title compound. $^1$H NMR (300 MHz, CDCl$_3$) δ ppm 1.00 (d, J=9.5 Hz, 1H) 1.09 (s, 3H) 1.24 (d, 3H) 1.34 (t, J=7.3 Hz, 3H) 1.55-1.68 (m, 2H) 1.85-2.03 (m, 4H) 2.08-2.26 (m, 1H) 2.32-2.45 (m, 1H) 2.51-2.70 (m, 2H) 2.70-2.86 (m, 2H) 7.44 (t, J=7.3 Hz, 1H) 7.66-7.72 (m, 1H) 7.76 (t, J=7.1 Hz, 1H) 8.21 (d, J=7.9 Hz, 1H); MS (ESI$^+$) m/z 354 (M+H)$^+$.

Example 3

N-(2-cyclopropyl-7-fluoro-4-oxoquinazolin-3(4H)-yl)-2-[(1S,2S,5S)-6,6-dimethylbicyclo[3.1.1]hept-2-yl]acetamide Example 3A 3-Amino-2-cyclopropyl-7-fluoroquinazolin-4(3H)-one Cyclopropanecarbonyl chloride (3.59 mL, 39.2 mmol) was added to a solution of 2-amino-4-fluorobenzoic acid (Aldrich) (2.0 g, 12.9 mmol) and pyridine (5.38 mL, 66.5 mmol) in tetrahydrofuran (15 mL). The mixture was stirred at 70° C. overnight. The mixture was cooled at 0° C., hydrazine (4.86 mL, 155 mmol) was added and the reaction was stirred at about room temperature for 30 minutes, then at about 75° C. for 24 hours. The reaction mixture was cooled to about 22° C., diluted with ethyl acetate, washed with aq. NaHCO$_3$, dried with magnesium sulfate, filtered, and concentrated. The residue was suspended in toluene and concentrated. The process was repeated to obtain the crude title compound.

Example 3B

N-(2-cyclopropyl-7-fluoro-4-oxoquinazolin-3(4H)-yl)-2-[(1S,2S,5S)-6,6-dimethylbicyclo[3.1.1]hept-2-yl]acetamide The product from Example 1C and Example 3A were processed using method analogous to that described in Example 1D to afford the title compound. $^1$HNMR (300 MHz, DMSO-d$_6$) δ ppm 0.88-0.97 (m, 1H) 0.97-1.13 (m, 8H) 1.19 (d, 3H) 1.48-1.70 (m, 1H) 1.76-2.05 (m, 6H) 2.11-2.27 (m, 1H) 2.28-2.40 (m, 1H) 2.42-2.48 (m, 1H) 7.25-7.40 (m, 2H) 8.14 (dd, J=9.5, 6.3 Hz, 1H) 11.07 (s, 1H); MS (ESI$^+$) m/z 384 (M+H)$^+$.

Example 4

N-[2-cyclopropyl-4-oxo-7-(trifluoromethyl)quinazolin-3(4H)-yl]-2-[(1S,2S,5S)-6,6-dimethylbicyclo[3.1.1]hept-2-yl]acetamide Example 4A 3-amino-2-cyclopropyl-7-(trifluoromethyl)quinazolin-4(3H)-one 2-Amino-4-(trifluoromethyl)benzoic acid (Matrix) was processed using method analogous to that described in Example 3A to afford the title compound.

Example 4B

N-[2-cyclopropyl-4-oxo-7-(trifluoromethyl)quinazolin-3(4H)-yl]-2-[(1S,2S,5S)-6,6-dimethylbicyclo[3.1.1]hept-2-yl]acetamide The product from Example 1C and Example 4A were processed using method analogous to that described in Example 1D to afford the title compound. $^1$HNMR (300 MHz, DMSO-d$_6$) δ ppm 0.83-1.00 (m, 1H) 1.00-1.13 (m, 8H) 1.19 (d, 3H) 1.36-1.67 (m, 1H) 1.74-2.07 (m, 6H) 2.16-2.39 (m, 2H) 2.52-2.64 (m, 1H) 7.77 (d, J=8.3 Hz, 1H) 8.28 (d, J=8.3 Hz, 1H) 11.17 (s, 1H); MS (ESI$^+$) m/z 434 (M+H)$^+$.

Example 5

N-(2-cyclopropyl-4-oxoquinazolin-3(4H)-yl)-2-[(1S,2S,5S)-6,6-dimethylbicyclo[3.1.1]hept-2-yl]acetamide Example 5A 3-amino-2-cyclopropyl-quinazolin-4(3H)-one 2-Amino-benzoic acid (Aldrich) was processed using method analogous to that described in Example 3A to afford the title compound.

Example 5B

N-(2-cyclopropyl-4-oxoquinazolin-3(4H)-yl)-2-[(1S,2S,5S)-6,6-dimethylbicyclo[3.1.1]hept-2-yl]acetamide The products from Example 1C and Example 5A were processed using method analogous to that described in Example 1D to afford the title compound. $^1$H NMR (300 MHz, DMSO-d$_6$) δ ppm 0.88-1.07 (m, 6H) 1.08 (s, 3H) 1.19 (d, 3H) 1.45-1.67 (m, 1H) 1.81-2.04 (m, 6H) 2.11-2.26 (m, 1H) 2.26-2.41 (m, 1H) 2.52-2.61 (m, 1H) 7.47 (t, J=8.1 Hz, 1H) 7.54 (d, J=7.80 Hz, 1H) 7.80 (t, J=7.1 Hz, 1H) 8.07 (d, J=8.1 Hz, 1H) 11.03 (s, 1H); MS (ESI$^+$) m/z 366 (M+H)$^+$.

Example 6

2-[(1S,2S,5S)-6,6-dimethylbicyclo[3.1.1]hept-2-yl]-N-(2-ethyl-4-oxothieno[2,3-d]pyrimidin-3(4H)-yl)acetamide The product from Example 1C and 3-amino-2-ethylthieno[2,3-d]pyrimidin-4(3H)-one (Enamine) were processed using method analogous to that described in Example 1D to afford the title compound. $^1$H NMR (300 MHz, DMSO-d$_6$) δ ppm 0.88-0.96 (m, 1H) 1.07 (s, 3H) 1.16-1.23 (m, 6H) 1.45-1.64 (m, 1H) 1.79-2.06 (m, 6H) 2.27-2.46 (m, 2H) 2.53-2.67 (m, 1H) 2.66-2.82 (m, 1H) 7.38 (d, J=7.1 Hz, 1H) 7.59 (d, J=5.6 Hz, 1H); MS (ESI$^+$) m/z 360 (M+H)$^+$.

Example 7

2-[(1S,2S,5S)-6,6-dimethylbicyclo[3.1.1]hept-2-yl]-N-[4-oxo-2-(trifluoromethyl)quinazolin-3(4H)-yl]acetamide The product from Example 1C and 3-amino-2-(trifluoromethyl)quinazolin-4(3H)-one (Bionet) were processed using method analogous to that described in Example 1D to afford the title compound. $^1$H NMR (300 MHz, CDCl$_3$) δ ppm 1.00 (d, J=9.8 Hz, 1H) 1.08 (s, 3H) 1.23 (d, J=5.1 Hz, 3H) 1.85-2.05 (m, 5H) 2.06-2.24 (m, 1H) 2.31-2.45 (m, 2H) 2.53-2.61

(m, 2H) 2.62-2.76 (m, 1H) 7.58 (s, 1H) 7.60-7.68 (m, 1H) 7.88 (d, J=3.7 Hz, 1H) 8.31 (d, J=7.8 Hz, 1H); MS (ESI$^+$) m/z 394 (M+H)$^+$.

Example 8

2-[(1S,2R,5S)-(6,6-dimethylbicyclo[3.1.1]hept-2-yl)methoxy]-N-[4-oxo-2-(propan-2-yl)quinazolin-3(4H)-yl]acetamide

Example 8A 2-4(1S,2R,5S)-6,6-dimethylbicyclo[3.1.1]heptan-2-yl)methoxy)acetic acid To a solution of (−)-cis-myrtanol (Aldrich) (89.0 g 0.58 mmol) in dimethoxy ethane (340 mL) was added sodium hydride (60% oil dispersion, 31.0 g, 0.81 mmol). The reaction mixture was refluxed for 2.5 hours. The mixture was cooled to about 50° C. and a solution of 2-chloroacetic acid (25.0 g 0.27 mmol) in dimethoxy ethane (180 mL) was added drop wise over a period of 30 minutes. After refluxing for 1 hour, the reaction mixture was cooled to about room temperature and quenched with water (75.0 mL). The mixture was concentrated, and then the residue was extracted 3 times with in ether. The ethereal solution was washed with 1 M sodium hydroxide, dried over sodium sulfate, filtered, and concentrated. The residue was crystallized from petroleum ether to get the title compound. Melting point 62-64° C.

Example 8B 2-(((1S,2R,5S)-6,6-dimethylbicyclo[3.1.1]heptan-2-yl)methoxy)acetyl chloride Example 8A was processed using the method analogous to that described in Example 1C to afford the title compound.

Example 8C

2-[(1S,2R,5S)-(6,6-dimethylbicyclo[3.1.1]hept-2-yl)methoxy]-N-[4-oxo-2-(propan-2-yl)quinazolin-3(4H)-yl]acetamide Example 8B and 3-amino-2-isopropylquinazolin-4(3H)-one were processed using method analogous to that described in Example 1D to afford the title compound. $^1$H NMR (300 MHz, DMSO-d$_6$) δ ppm 0.93 (d, J=9.5 Hz, 1H) 0.99 (s, 3H) 1.21 (s, 3H) 1.18-1.22 (m, 3H) 1.25 (d, J=6.7 Hz, 3H) 1.43-1.60 (m, 1H) 1.80-1.97 (m, 4H) 1.97-2.09 (m, 1H) 2.22-2.48 (m, 3H) 3.05-3.20 (m, 1H) 3.44-3.65 (m, 2H) 4.19 (s, 2H) 7.54 (t, J=7.5 Hz, 1H) 7.68 (d, J=7.5 Hz, 1H) 7.86 (t, J=6.9 Hz, 1H) 8.11 (d, J=7.9 Hz, 1H) 10.83 (s, 1H); MS (ESI$^+$) m/z 398 (M+H)$^+$.

Example 9

2-({[(1S,2R,5S)-6,6-dimethylbicyclo[3.1.1]hept-2-yl]methyl}sulfanyl)-N-[4-oxo-2-(propan-2-yl)quinazolin-3(4H)-yl]propanamide

Example 9A 2-(((1S,2R,5S)-6,6-dimethylbicyclo[3.1.1]heptan-2-yl)methylthio)propanoic acid To a solution of ((1S,2R,5S)-6,6-dimethylbicyclo[3.1.1]heptan-2-yl)methanethiol (Eisen, Moris; et al. *Inorg. Chim. Acta* 1991, 188, 167-176) (52.0 g, 0.30 mmol) and potassium hydroxide (41.2 g, 0.62 mmol) in water (200 mL) was added α-chloro-propionic acid (33.2 g, 0.306 mmol) drop wise. The mixture was heated at 100° C. for 1 hour. The mixture was cooled and acidified to pH=1 with 6N HCl (100 mL). The product was extracted with ether, dried with magnesium sulfate and concentrated. The residue was distilled at reduced pressure (143-147° C., 0.5 mm of Hg) to obtain the title compound.

Example 9B 2-(((1S,2R,5S)-6,6-dimethylbicyclo[3.1.1]heptan-2-yl)methylthio)propionyl chloride Example 9A was processed using method analogous to that described in Example 1C to afford the title compound.

Example 9C 2-({[(1S,2R,5S)-6,6-dimethylbicyclo[3.1.1]hept-2-yl]methyl}sulfanyl)-N-[4-oxo-2-(propan-2-yl)quinazolin-3(4H)-yl]propanamide Example 9B and 3-amino-2-isopropylquinazolin-4(3H)-one were processed using method analogous to that described in Example 1D to afford the title compound. $^1$H NMR (300 MHz, DMSO-d$_6$) δ ppm 0.81-0.82 (m, 1H) 0.86-1.03 (m, 3H) 1.35-1.56 (m, 12H) 1.35-1.58 (m, 3H) 1.70-2.07 (m, 4H) 2.17-2.40 (m, 2H) 2.67-2.84 (m, 2H) 3.02-3.20 (m, 1H) 3.59-3.72 (m, 1H) 7.54 (t, J=7.9 Hz, 1H) 7.63-7.72 (m, 1H) 7.81-7.90 (m, 1H) 8.11 (d, J=7.9 Hz, 1H) 11.12 (s, 1H); MS (ESI$^+$) m/z 428 (M+H)$^+$.

Example 10

2-{2-[(1S,2S,5S)-6,6-dimethylbicyclo[3.1.1]hept-2-yl]ethoxy}-N-[4-oxo-2-(propan-2-yl)quinazolin-3(4H)-yl]acetamide

Example 10A 2-(2-((1R,5S)-6,6-dimethylbicyclo[3.1.1]hept-2-en-2-yl)ethoxy)acetic acid To a solution of (−)-nopol (Aldrich) (100 g, 0.60 mmol) in dimethoxy ethane (350 mL) was added NaH (60% oil dispersion, 31.1 g, 0.81 mmol). The mixture was refluxed for 2.5 hours, cooled to 45° C., and 2-chloroacetic acid (23.5 g 0.25 mmol) in dimethoxy ethane (180 mL) was added drop wise over a period of 1.5 hours. The reaction mixture was refluxed for 1 hour. After cooling at room temperature, water (75 mL) was added slowly, followed by 10% aqueous NaOH. The mixture was extracted with ether (1 L) (discarded), the aqueous phase was acidified and extracted with ether. The organic layer was dried over magnesium sulfate, filtered, and concentrated. The residue was distilled under reduced pressure to yield the title compound (29.5 g, 135-137° C. at 1.0 mm of Hg). n$^{25}$$_D$ 1.4914, mp 78-80° C.

Example 10B 2-(2-((1S,2S,5S)-6,6-dimethylbicyclo[3.1.1]heptan-2-yl)ethoxy)acetic acid Example 10A (15.9 g 0.07 mmol) was dissolved in ethyl acetate (100 mL). PtO$_2$ (0.45 g) was added under N$_2$ atmosphere. The mixture was hydrogenated at 45 psi. Uptake was completed within 1 h. The mixture was filtered, washed with ethyl acetate and concentrated to afford 15.5 g of the title compound. $n^{25}{}_D$ 1.4821.

Example 10C 2-(2-((1S,2S,5S)-6,6-dimethylbicyclo[3.1.1]heptan-2-yl)ethoxy)acetyl chloride Example 10B was processed using method analogous to that described in Example 1C to afford the title compound.

Example 10D

2-{2-[(1S,2S,5S)-6,6-dimethylbicyclo[3.1.1]hept-2-yl]ethoxy}-N-[4-oxo-2-(propan-2-yl)quinazolin-3(4H)-yl]acetamide Example 10C and 3-amino-2-isopropylquinazolin-4(3H)-one were processed using method analogous to that described in Example 1D to afford the title compound. $^1$H NMR (300 MHz, DMSO-$d_6$) δ ppm 0.89 (d, J=9.5 Hz, 1H) 1.02 (s, 3H) 1.18 (s, 3H) 1.20 (d, J=6.7 Hz, 3H) 1.26 (d, J=6.7 Hz, 3H) 1.39-1.59 (m, 2H) 1.64-1.79 (m, 2H) 1.80-2.01 (m, 4H) 2.06-2.18 (m, 1H) 2.25-2.39 (m, 1H) 3.03-3.20 (m, 1H) 3.49-3.68 (m, 2H) 4.19 (s, 2H) 7.54 (t, J=8.1 Hz, 1H) 7.68 (d, J=8.3 Hz, 1H) 7.81-7.90 (m, 1H) 8.11 (dd, J=7.9, 1.2 Hz, 1H) 10.86 (s, 1H); MS (ESI$^+$) m/z 412 (M+H)$^+$.

Example 11

3-({[(1S,2R,5S)-6,6-dimethylbicyclo[3.1.1]hept-2-yl]methyl}sulfanyl)-N-[4-oxo-2-(propan-2-yl)quinazolin-3(4H)-yl]propanamide Example 11A 3-4(1S,2R,5S)-6,6-dimethylbicyclo[3.1.1]heptan-2-yl)methylthio)propanoic acid To a solution of ((1S,2R,5S)-6,6-dimethylbicyclo[3.1.1]heptan-2-yl)methanethiol (26.0 g, 0.15 mmol) and potassium hydroxide (30.6 g, 0.153 mmol) in water (100 mL) was added β-bromopropionic acid (16.6 g, 0.153 mmol) drop wise. The reaction was heated at 100° C. for 1 hour. The mixture was cooled and extracted with ether. The aqueous phase was acidified to pH=1 with 3N HCl (100 mL) and extracted with ether (3×100 mL). The organic solution was dried over magnesium sulfate, filtered, and concentrated. The residue was distilled under reduced pressure to obtain the title compound (160-163° C., 10.2 mm of Hg).

Example 11B 3-(((1S,2R,5S)-6,6-dimethylbicyclo[3.1.1]heptan-2-yl)methylthio)propionyl chloride Example 11A was processed using method analogous to that described in Example 1C to afford the title compound.

Example 11C 3-({[(1S,2R,5S)-6,6-dimethylbicyclo[3.1.1]hept-2-yl]methyl}sulfanyl)-N-[4-oxo-2-(propan-2-yl)quinazolin-3(4H)-yl]propanamide Example 11B and 3-amino-2-isopropylquinazolin-4(3H)-one were processed using method analogous to that described in Example 1D to afford the title compound. $^1$H NMR (300 MHz, DMSO-$d_6$) δ ppm 0.90 (d, J=8.5 Hz, 1H) 1.00 (s, 3H) 1.12-1.28 (m, 9H) 1.40-1.62 (m, 1H) 1.67-2.09 (m, 6H) 2.08-2.40 (m, 2H) 2.55-2.73 (m, 2H) 2.73-2.85 (m, 1H) 3.16-3.26 (m, 1H) 7.53 (t, J=7.5 Hz, 1H) 7.63-7.73 (m, 1H) 7.78-7.91 (m, 1H) 8.10 (d, J=9.2 Hz, 1H) 11.06 (s, 1H); MS (ESI$^+$) m/z 428 (M+H)$^+$.

Example 12

2-({[(1S,2R,5S)-6,6-dimethylbicyclo[3.1.1]hept-2-yl]methyl}sulfanyl)-N-[4-oxo-2-(propan-2-yl)quinazolin-3(4H)-yl]acetamide Example 12A 2-(((1S,2R,5S)-6,6-dimethylbicyclo[3.1.1]heptan-2-yl)methylthio)acetyl chloride 2-(((1S,2R,5S)-6,6-dimethylbicyclo[3.1.1]heptan-2-yl)methylthio)acetic acid (Nikitina, L. E.; et al. Chemistry of Natural Compounds 2006, 42, 178) was processed using method analogous to that described in Example 1C to afford the title compound.

Example 12B 2-({[(1S,2R,5S)-6,6-dimethylbicyclo[3.1.1]hept-2-yl]methyl}sulfanyl)-N-[4-oxo-2-(propan-2-yl)quinazolin-3(4H)-yl]acetamide Example 12A and 3-amino-2-isopropylquinazolin-4(3H)-one were processed using method analogous to that described in Example 1D to afford the title compound. $^1$H NMR (300 MHz, DMSO-$d_6$) δ ppm 0.90 (d, J=8.5 Hz, 1H) 0.99 (s, 3H) 1.18 (s, 3H) 1.21 (d, J=6.8 Hz, 3H) 1.25 (d, J=6.8 Hz, 3H) 1.41-1.58 (m, 1H) 1.68-2.07 (m, 6H) 2.13-2.38 (m, 3H) 2.67-2.82 (m, 2H) 3.08-3.21 (m, 1H) 3.34-3.48 (m, 2H) 7.53 (t, J=8.1 Hz, 1H) 7.68 (d, J=8.1 Hz, 1H) 7.79-7.90 (m, 1H) 8.11 (dd, J=7.8, 1.3 Hz, 1H) 11.12 (s, 1H); MS (ESI$^+$) m/z 414 (M+H)$^+$.

Example 13

2-[(1S,2S,5S)-6,6-dimethylbicyclo[3.1.1]hept-2-yl]-N-[6-fluoro-4-oxo-2-(propan-2-yl)quinazolin-3(4H)-yl]acetamide Example 13A Methyl 5-fluoro-2-isobutyramidobenzoate To a mixture of methyl 2-amino-5-fluorobenzoate (alfa) (16.9 g, 100 mmol) and isobutyryl chloride (21.2 g, 200 mmol) in dry tetrahydrofuran was added triethylamine (40.4 g, 400 mmol) at 0° C., then the mixture was stirred at room temperature overnight. After removal of the solvent under reduced pressure, the mixture was suspended in water and extracted with ethyl acetate. The organic layer was washed with brine, dried over MgSO$_4$, filtered, and concentrated. The crude product was recrystallized from ethyl acetate/petroleum ether (5:1, 150 mL) to give the title compound as white solid (12.3 g, 51.5%).

Example 13B 3-amino-6-fluoro-2-isopropylquinazolin-4(3H)-one

Example 13A (12.3 g, 51.4 mmol) and hydrazine hydrate (12.9 g, 257 mmol) in n-butanol (200 mL) was stirred overnight at 90° C. After removal of the solvent under reduced pressure, the crude mixture was purified by silica gel column chromatography (petroleum ether: ethyl acetate, 4:1) to give the title compound as white solid (6.8 g, yield 59.9%). $^1$H NMR (400 MHz, DMSO-d6) δ 7.79-7.64 (m, 3H), 5.71 (s, 1H), 3.77-3.70 (m, 1H,), 1.27 (d, 6H, 6.8 Hz); LCMS m/z 222.1 (M+H)$^+$, RT 1.75 min.

Example 13C

2-[(1S,2S,5S)-6,6-dimethylbicyclo[3.1.1]hept-2-yl]-N-(6-fluoro-2-isopropyl-4-oxoquinazolin-3(4H)-yl)acetamide The product from Example 1C and Example 13B were processed using method analogous to that described in Example 1D to afford the title compound. $^1$HNMR (400 MHz, CDCl$_3$) δ ppm 1.02-1.08 (m, 1H) 1.09 (s, 3H) 1.24 (s, 3H) 1.30 (d, J=5.4 Hz, 3H) 1.35 (d, J=6.8 Hz, 3H) 1.61-1.54 (m, 1H) 1.89-2.00 (m, 4H) 2.10-2.16 (m, 1H) 2.32-2.44 (m, 1H) 2.53-2.63 (m, 2H) 2.64-2.79 (m, 1H) 3.10-3.20 (m, 1H) 7.28-7.50 (m, Hz, 1H) 7.71 (dd, J=5.0, 9.2 Hz, 1H) 7.22 (s, dd, J=2.6, 8.2 Hz, 1H), 10.87 (s, 1H); MS (ESI$^+$) m/z 386 (M+H)$^+$.

Example 14

2-[(1S,2S,5S)-6,6-dimethylbicyclo[3.1.1]hept-2-yl]-N-[4-oxo-2-(2,2,2-trifluoroethyl)quinazolin-3(4H)-yl]acetamide

Example 14A

Methyl 5-fluoro-2-(3,3,3-trifluoropropanamido)benzoate

To a solution of methyl 2-aminobenzoate (47.0 g, 312.5 mmol), and 3,3,3-trifluoropropanoic acid (40.0 g, 312.5 mmol) in pyridine (20 mL) was added phosphoryl chloride (95.0 g, 625 mmol) at 0° C., and stirred at 0° C. for 20 minutes. After evaporation of the phosphoryl chloride, water was added into the mixture, followed by extraction with diethyl ether (2×500 mL), dried over MgSO$_4$, filtered, and concentration. The residue was recrystallized from ethyl acetate:petroleum ether (5:1, 75 mL) to obtain the title compound as light yellow solid (48.2 g, 40.2%).

Example 14B 3-amino-2-(2,2,2-trifluoroethyl)quinazolin-4(3H)-one

Example 14A was processed using method analogous to that described in Example 13B to afford the title compound.

Example 14C

2-[(1S,2S,5S)-6,6-dimethylbicyclo[3.1.1]hept-2-yl]-N-[4-oxo-2-(2,2,2-trifluoroethyl)quinazolin-3(4H)-yl]acetamide The product from Example 14B and Example 1C were processed using the method described in Example 1D to afford the title compound. $^1$H NMR (400 MHz, CDCl$_3$) δ ppm 0.96-1.06 (m, 1H) 1.22 (s, 3H) 1.26 (s, 3H) 1.61-1.54 (m, 1H) 1.89-2.00 (m, 4H) 2.12-2.17 (m, 1H) 2.35-2.40 (m, 1H) 2.52-2.60 (m, 2H) 2.65-2.71 (m, 1H) 3.62-3.77 (m, 1H), 3.54-3.60 (m, 1H) 7.51 (t, J=8.2 Hz, 1H), 7.71 (d, J=7.6 Hz, 1H) 7.81 (t, J=8.2 Hz, 1H), 8.20-8.24 (m, 2H); MS (ESI$^+$) m/z 408 (M+H)$^+$.

Example 15

N-(2-cyclopropyl-4-oxothieno[2,3-d]pyrimidin-3(4H)-yl)-2-[(1S,2S,5S)-6,6-dimethylbicyclo[3.1.1]hept-2-yl]acetamide

Example 15A

Methyl 2-(cyclopropanecarboxamido)thiophene-3-carboxylate

Cyclopropanecarbonyl chloride and methyl 2-aminothiophene-3-carboxylate (Aldrich) were processed using method analogous to that described in Example 13A to afford the title compound.

Example 15B

3-Amino-2-cyclopropylthieno[2,3-d]pyrimidin-4(3H)-one

Example 15A was processed using method analogous to that described in Example 13B to afford the title compound.

Example 15C

N-(2-cyclopropyl-4-oxothieno[2,3-d]pyrimidin-3(4H)-yl)-2-[(1S,2S,5S)-6,6-dimethylbicyclo[3.1.1]hept-2-yl]acetamide Example 1C and Example 15B were processed using method analogous to that described in Example 1D to afford the title compound. $^1$H NMR (300 MHz, DMSO-d$_6$) δ ppm 0.88-0.96 (m, 1H) 1.00-1.07 (m, 4H) 1.08 (s, 3H) 1.16 (d, 3H) 1.45-1.64 (m, 1H) 1.79-2.06 (m, 5H) 2.27-2.46 (m, 2H) 2.23-2.27 (m, 3H) 7.35 (d, J=6.0 Hz, 1H) 7.52 (d, J=6.2. Hz, 1H) 11.09 (d, 1H); MS (ESI$^+$) m/z 372 (M+H)$^+$.

Example 16

2-[(1S,2S,5S)-6,6-dimethylbicyclo[3.1.1]hept-2-yl]-N-(4-oxoquinazolin-3(4H)-yl)acetamide Example 1C and 3-aminoquinazolin-4(3H)-one (Aldrich) were processed using method analogous to that described in Example 1D to afford the title compound. $^1$H NMR (300 MHz, DMSO-d$_6$) δ ppm 0.92 (d, J=9.5 Hz, 1H) 1.08 (s, 3H) 1.21 (s, 3H) 1.46-1.65 (m, 1H) 1.79-2.07 (m, 5H) 2.28-2.46 (m, 3H) 2.55-2.50 (m, 1H) 7.60 (t, J=7.1 Hz, 1H) 7.74 (d, J=7.4 Hz, 1H) 7.89 (t, J=8.1 Hz, 1H) 8.18 (d, J=6.8 Hz, 1H) 8.22 (s, 1H) 11.20 (s, 1H); MS (ESI$^+$) m/z 325 (M+H)$^+$.

Example 17

2-[(1S,2S,5S)-6,6-dimethylbicyclo[3.1.1]hept-2-yl]-N-(2-methyl-4-oxoquinazolin-3(4H)-yl)acetamide Example 1C and 3-amino-2-methylquinazolin-4(3H)-one (Aldrich) were processed using method analogous to that described in Example 1D to afford the title compound. $^1$H NMR (300 MHz, DMSO-d$_6$) δ ppm 0.92 (d, J=9.5 Hz, 1H) 1.08 (s, 3H) 1.21 (s, 3H) 1.46-1.65 (m, 1H) 1.79-2.07 (m, 5H) 2.28-2.46 (m, 3H) 2.55-2.50 (m, 1H) 7.60 (t, J=7.1 Hz, 1H)

7.74 (d, J=7.4 Hz, 1H) 7.89 (t, J=8.1 Hz, 1H) 8.18 (d, J=6.8 Hz, 1H) 8.22 (s, 1H) 11.20 (s, 1H); MS (ESI⁺) m/z 325 (M+H)⁺.

Example 18

N-[6-chloro-4-oxo-2-(propan-2-yl)quinazolin-3(4H)-yl]-2-[(1S,2S,5S)-6,6-dimethylbicyclo[3.1.1]hept-2-yl]acetamide Example 18A Methyl 5-chloro-2-isobutyramidobenzoate Isobutyryl chloride (Aldrich) and 2-amino-5-chlorobenzoic acid (Aldrich) were processed using method analogous to that described in Example 13A to afford the title compound.

Example 18B 3-amino-6-chloro-2-isopropylquinazolin-4(3H)-one

Example 18A was processed using method analogous to that described in Example 13B to afford the title compound.

Example 18C

N-(6-chloro-2-isopropyl-4-oxoquinazolin-3(4H)-yl)-2-[(1S,2S,5S)-6,6-dimethylbicyclo[3.1.1]hept-2-yl]acetamide Example 1C and 18B were processed using method analogous to that described in Example 1D to afford the title compound. ¹H NMR (400 MHz, CD3OD) δ ppm 1.05 (d, J=9.5 Hz, 1H) 1.27 (s, 3H) 1.24-1.35 (m, 9H) 1.62-1.74 (m, 1H) 1.89-2.00 (m, 4H) 2.44-2.47 (m, 1H) 2.55-2.70 (m, 2H) 3.19-3.24 (m, 1H) 7.75 (d, J=8.2 Hz, 1H) 7.81 (d, J=8.2 Hz, 1H) 8.14 (s, 1H); MS (ESI⁺) m/z 402 (M+H)⁺.

Example 19

N-[2-(diethylamino)-4-oxoquinazolin-3(4H)-yl]-2-[(1S,2S,5S)-6,6-dimethylbicyclo[3.1.1]hept-2-yl]acetamide Example 19A Methyl 2-(3,3-diethyl-thioureido)benzoate Methyl 2-isothiocyanatobenzoate (Acros) (20.0 g, 104 mmol) was dissolved in tetrahydrofuran (300 mL), followed by addition of diethylamine (35.9 mL, 349 mmol). The reaction mixture was stirred at room temperature. After 1 hour, the mixture was poured into water (800 mL). The precipitate was collected by filtration, washed with water and dried under vacuum to give the title compound (26.2 g, yield 94.2%).

Example 19B 3-amino-2-(diethylamino)quinazolin-4(3H)-one

Example 19A (18.0 g, 67.6 mmol) was dissolved in methanol (90 mL), followed by addition of iodomethane (6.75 mL, 135.2 mmol). The reaction mixture was heated at 80° C. for 10 minutes under microwave irradiation (making sure the temperature was not higher than 80° C.). The reaction mixture was evaporated to dryness and then re-dissolved in methanol (200 mL). Hydrazine monohydrate (8.2 mL, 169 mmol) was added followed by stirring at room temperature overnight. The reaction mixture was poured into water (500 mL), followed by extraction with diethyl ether (2×200 mL). The organic phase was dried over MgSO₄, filtered, and concentrated. The crude product was subjected to column chromatography (ethyl acetate/petroleum ether, 1/4) on silica gel to give the title compound (8.2 g, yield 52.3%). ¹H NMR (400 MHz, DMSO-d6): δ 7.96 (d, 1H, 6.4 Hz), 7.64-7.61 (m, 1H), 7.36 (m 1H), 7.23-7.20 (m, 1H), 5.59 (d, 2H, 2 Hz), 3.49-3.45 (m, 4H), 1.20-1.17 (m, 6H); LC-MS m/z 397 (M+H)⁺, RT 1.38 min.

Example 19C

N-[2-(diethylamino)-4-oxoquinazolin-3(4H)-yl]-2-[(1S,2S,5S)-6,6-dimethylbicyclo[3.1.1]hept-2-yl]acetamide Example 1C and Example 19B were processed using method analogous to that described in Example 1D to afford the title compound. ¹H NMR (400 MHz, DMSO-d₆-CD₃OD) δ ppm 0.98 (d, J=9.6 Hz 1H) 1.08 (s, 3H) 1.18 (t, J=7.2 Hz, 6H) 1.16 (d, 3H) 1.46-1.64 (m, 1H) 1.79-2.27 (m, 5H) 2.43-2.68 (m, 4H) 3.45-3.54 (m, 2H) 3.22-3.29 (m, 2H) 7.29 (t, J=8.2 Hz, 1H), 7.46 (d, J=7.6 Hz, 1H) 7.70 (t, J=7.6 Hz, 1H), 8.05 (d, J=8.4 Hz, 1H); MS (ESI⁺) m/z 397 (M+H)⁺.

Example 20

2-[(1S,2S,5S)-6,6-dimethylbicyclo[3.1.1]hept-2-yl]-N-[4-oxo-2-(propan-2-yl)thieno[2,3-d]pyrimidin-3(4H)-yl]acetamide Example 20A Methyl 2-isobutyramidothiophene-3-carboxylate Isobutyl chloride and methyl 2-aminothiophene-3-carboxylate were processed using method analogous to that described in Example 13A to afford the title compound.

Example 20B

3-Amino-2-isopropylthieno[2,3-d]pyrimidin-4(3H)-one

Example 20A was processed using method analogous to that described in Example 13B to afford the title compound.

Example 20C

2-[(1S,2S,5S)-6,6-dimethylbicyclo[3.1.1]hept-2-yl]-N-(2-isopropyl-4-oxothieno[2,3-c]pyrimidin-3(4H)-yl)acetamide Example 1C and Example 20B were processed using method analogous to that described in Example 1D to afford the title compound. ¹H NMR (400 MHz, DMSO-d₆) δ ppm 0.94 (d, J=9.5 Hz, 1H) 1.08 (s, 3H) 1.17-1.25 (m, 9H) 1.52-1.59 (m, 1H) 1.84-1.96 (m, 5H) 2.25-2.35 (m, 2H) 2.44-2.57

(m, 2H) 3.09-3.13 (m, 1H) 7.38 (d, J=6.0 Hz, 1H) 7.58 (d, J=5.6 Hz, 1H) 10.94 (s, 1H); MS (ESI$^+$) m/z 374 (M+H)$^+$.

Example 21

2-[(1S,2R,5S)-6,6-dimethylbicyclo[3.1.1]hept-2-yl]-N-[4-oxo-2-(propan-2-yl)quinazolin-3(4H)-yl]acetamide

Example 21A ((1S,2S,5S)-6,6-dimethylbicyclo[3.1.1]heptan-2-yl)methyl 4-methylbenzenesulfonate A solution of ((1S,2S,5S)-6,6-dimethylbicyclo[3.1.1]heptan-2-yl)methanol (7.0 mL, 44.2 mmol) and triethylamine (13.5 mL, 97.0 mmol) in dichloromethane (60 mL) was cooled to 0° C. A solution of 4-methylbenzene-1-sulfonyl chloride (10.9 g, 57.4 mmol) in dichloromethane (20 mL) was added drop wise at 0° C. The reaction was stirred at room temperature for 16 hours. The mixture was washed with saturated aqueous NaHCO$_3$ and the aqueous layer was extracted twice with dichloromethane. The organic extracts were dried over sodium sulfate, filtered, and concentrated to give the title compound.

Example 21B 2-((1S,2R,5S)-6,6-dimethylbicyclo[3.1.1]heptan-2-yl)acetonitrile To a solution of Example 21A (13.6 g, 44.2 mmol) in DMSO (100 mL) was added potassium cyanide (11.5 g, 177 mmol). The reaction was heated at 70° C. for 48 h. The mixture was diluted with brine and extracted with ether (3×75 mL). The organic extracts were dried over magnesium sulfate and concentrated. The residue was purified by flash chromatography on SiO$_2$ (Hexanes/ethyl acetate, gradient 0 to 50%) to give the title compound.

Example 21C 2-((1S,2R,5S)-6,6-dimethylbicyclo[3.1.1]heptan-2-yl)acetic acid

Concentrated sulfuric acid (33 mL) was added drop wise to ethanol (120 mL) at 0° C. A solution of Example 21B (7.20 g, 44.1 mmol) in ethanol (20 mL) was added to the ethanol-H$_2$SO$_4$ mixture. The mixture was heated at reflux for 24 hours. TLC showed a 1/1 mixture of ethyl ester and acid. The mixture was diluted with water. Ethanol was evaporated under reduced pressure and the mixture was extracted with ether. The organic extracts were dried with magnesium sulfate, filtered, and concentrated. The residue was dissolved in tetrahydrofuran (50 mL). To the mixture was added a solution of 25% NaOH (10 mL). The reaction was heated at 40° C. for 12 hours. The mixture was cooled at room temperature, tetrahydrofuran was evaporated, the mixture was diluted with brine and washed with ether (2×25 mL). The aqueous phase was acidified to pH 2 with 5 N HCl and extracted with ether (3×75 mL). The organic extracts were dried over magnesium sulfate, filtered, and concentrated to give the title compound.

Example 21D 2-((1S,2R,5S)-6,6-dimethylbicyclo[3.1.1]heptan-2-yl)acetyl chloride Example 21C was processed using method analogous to that described in Example 1C to afford the title compound.

Example 21E

2-[(1S,2R,5S)-6,6-dimethylbicyclo[3.1.1]hept-2-yl]-N-(2-isopropyl-4-oxoquinazolin-3(4H)-yl)acetamide Example 21D and 3-amino-2-isopropylquinazolin-4(3H)-one (Aldrich) were processed using method analogous to that described in Example 1D to afford the title compound. $^1$H NMR (300 MHz, DMSO-d$_6$) δ ppm 0.84 (s, 1H) 1.15-1.27 (m, 9H) 1.30-1.46 (m, 2H) 1.68-1.93 (m, 5H) 2.03-2.13 (m, 1H) 2.19-2.38 (m, 2H) 2.39-2.45 (m, 1H) 2.99-3.16 (m, 1H) 7.53 (t, J=7.6 Hz, 1H) 7.67 (d, J=8.5 Hz, 1H) 7.85 (t, J=8.5 Hz, 1H) 8.11 (d, J=8.1 Hz, 1H) 10.91 (d, 1H); MS (ESI$^+$) m/z 368 (M+H)$^+$.

Example 22

(±)-2-(bicyclo[2.1.1]hex-2-yl)-N-[4-oxo-2-(propan-2-yl)quinazolin-3(4H)-yl]acetamide

Example 22A

Ethyl 2-(bicyclo[2.1.1]hexan-2-ylidene)acetate

To a suspension of NaH (150 mg, 3.8 mmol, 60% dispersion in oil) in 1,2-dimethoxy ethane (20 mL) at 0° C. was added triethyl phosphono acetate (0.8 mL, 4.1 mmol). The resulting mixture was stirred 15 minutes at 0° C., 15 minutes at room temperature, and cooled to 0° C. Then, a solution of Bicyclo[2.1.1]hexan-2-one (obtained using the procedure described in J. Org. Chem. 1990, 55(2), 695-711) (300 mg, 3.1 mmol) in 1,2-dimethoxy ethane (4 mL) was added and the resulting solution was stirred for 5 minutes at 0° C. and then stirred at room temperature overnight. Water was added and the aqueous layer was extracted with ethyl acetate (3×20 mL). The combined organic layers were washed with water (20 mL), brine (20 mL), dried over MgSO$_4$, filtered and concentrated under reduced pressure. The residue was purified by flash chromatography (hexanes-ethyl acetate, 0 to 20%) to give the title compound. MS (DCI/NH$_3$) m/z 184 (M+NH$_4$)$^+$.

Example 22B

Ethyl 2-(bicyclo[2.1.1]hexan-2-yl)acetate

A mixture of Example 22A (200 mg, 1.2 mmol) Pd/C (25 mg, 0.02 mmol) in ethanol (25 mL) was stirred under H$_2$ atmosphere using a balloon until the starting material is completely consumed. The mixture was filtered and concentrated under reduced pressure to obtain 150 mg of the title compound. MS (DCI/NH$_3$) m/z 186 (M+NH$_4$)$^+$

Example 22C 2-(bicyclo[2.1.1]hexan-2-yl)acetic acid

To a solution of Example 22B (150 mg, 0.9 mmol) in tetrahydrofuran/methanol/water (2:2:1, 5 mL) was added 5 N aqueous NaOH solution (0.9 mL, 4.5 mmol). The mixture was stirred at room temperature for 4 hours and then extracted with methylene chloride to remove unreacted starting material. The aqueous layer was acidified (pH~2) with 6 N aqueous HCl solution and then extracted with methylene chloride. The combined acidic extracts were dried ($Na_2SO_4$), filtered and concentrated under reduced pressure to afford the title compound. MS ($DCI/NH_3$) m/z 158 $(M+NH_4)^+$.

Example 22D (±)-2-(bicyclo[2.1.1]hex-2-yl)-N-[4-oxo-2-(propan-2-yl)quinazolin-3(4H)-yl]acetamide To a mixture of 3-amino-2-isopropylquinazolin-4(3H)-one (Aldrich, 80 mg, 0.4 mmol) and Example 22C (55 mg, 0.4 mmol) in tetrahydrofuran (5 mL) was added a solution of 1-propanephosphonic acid cyclic anhydride (Aldrich, 50% w/w in ethyl acetate (0.7 mL, 1.2 mmol) followed by triethylamine (0.16 mL, 1.2 mmol). The reaction was stirred at 80° C. overnight. The reaction was quenched with 1M $NaHCO_3$ (10 mL). The aqueous layer was extracted with ethyl acetate (2×20 mL). The combined organic layers were dried over $Na_2SO_4$, filtered and concentrated under reduced pressure. The residue was purified by column chromatography ($SiO_2$, 0-50% of ethyl acetate in hexanes) to obtain 65 mg of the title compound. $^1$H NMR (400 MHz, $CDCl_3$) δ ppm 1.10 (m, 2H), 1.21-1.29 (m, 1H), 1.31 (d, J=6.7 Hz, 3H), 1.36 (d, J=6.7 Hz, 3H), 1.57-1.78 (m, 2H), 1.94-2.07 (m, 1H), 2.42-2.68 (m, 5H), 3.12-3.27 (m, 1H), 7.38-7.50 (m, 1H), 7.65-7.81 (m, 3H), 8.21 (dd, J=8.1, 1.0 Hz, 1H); MS ($ESI^+$) m/z 326 $(M+H)^+$. Elemental Analysis: Calculated for $C_{19}H_{23}N_3O_2$: C: C, 70.13; H, 7.12; N, 12.91. Found: C, 70.32; H, 7.10; N, 12.85.

Example 23

2-[(1R,3R,5S)-2-fluoro-6,6-dimethylbicyclo[3.1.1]hept-3-yl]-N-[4-oxo-2-(propan-2-yl)quinazolin-3(4H)-yl]acetamide Example 23A Ethyl 2-((1R,3R,5S)-6,6-dimethyl-2-oxobicyclo[3.1.1]heptan-3-yl)acetate The title compound was prepared according to the procedure as described in Campos, Kevin, et al, Tetrahedron letters 2002, (43), 6957-6959. MS ($DCI/NH_3$) m/z 242 $(M+NH_4)^+$.

Example 23B

Ethyl 2-((1R,3R,5S)-2-hydroxy-6,6-dimethylbicyclo[3.1.1]heptan-3-yl)acetate

To a cooled solution of Example 23A (0.62 g, 2.8 mmol) in EtOH (20 mL) was added sodium borohydride (0.13 g, 3.3 mmol) in portions at 0° C. The mixture was stirred at 0° C. for 4 hours and at room temperature overnight. The reaction mixture was then cooled, quenched with 1M $NaHCO_3$, extracted with dichloromethane (3×15 mL). The combined organic layers were dried over $Na_2SO_4$, filtered, and concentrated under reduced pressure. The residue was purified by column chromatography ($SiO_2$, 0-30% of ethyl acetate in hexanes) to obtain 0.35 g of the title compound. MS ($DCI/NH_3$) m/z 244 $(M+NH_4)^+$ Example 23C Ethyl 2-((1R,3R,5S)-2-fluoro-6,6-dimethylbicyclo[3.1.1]heptan-3-yl)acetate To a cooled solution of Example 23B (0.2 g, 0.9 mmol) in methylene chloride (5 mL), was added bis(2-methoxyethyl)aminosulfur trifluoride (0.25 g, 1.1 mmol) at 0° C. After stirring for 3 hours at 0° C., the reaction mixture was quenched with 1M $NaHCO_3$ (5 mL), extracted with methylene chloride (2×10 mL). The combined organic layers were dried over $Na_2SO_4$, filtered, and concentrated under reduced pressure. The residue was purified by column chromatography ($SiO_2$, 0-30% of ethyl acetate in hexanes) to obtain 0.15 g of the title compound. MS ($DCI/NH_3$) m/z 246 $(M+NH_4)^+$.

Example 23D 2-((1R,3R,5S)-2-fluoro-6,6-dimethylbicyclo[3.1.1]heptan-3-yl)acetic acid Example 23C and NaOH were reacted using method analogous to that described in Example 22C to provide the title compound. MS ($DCI/NH_3$) m/z 218 $(M+NH_4)^+$ Example 23E 2-[(1R,3R,5S)-2-fluoro-6,6-dimethylbicyclo[3.1.1]hept-3-yl]-N-[4-oxo-2-(propan-2-yl)quinazolin-3(4H)-yl]acetamide 3-Amino-2-isopropyl-4(3H)-quinazolinone, Example 23D, and 1-propanephosphonic acid were reacted using method analogous to that described in Example 22D to provide the title compound. $^1$H NMR (300 MHz, $CDCl_3$) δ ppm 0.83-0.92 (m, 1H), 0.95 (s, 3H), 0.96 (s, 3H), 1.20 (d, J=7.8 Hz, 3H), 1.20-1.30 (m, 1H), 1.24 (d, J=6.8 Hz, 3H), 1.31-1.42 (m, 1H), 1.72-1.88 (m, 3H), 2.24-2.46 (m, 3H), 3.02-3.17 (m, 1H), 3.97-4.23 (m, 1H), 7.48-7.57 (m, J=15.1, 1.2 Hz, 1H), 7.67 (d, J=8.1 Hz, 1H), 7.81-7.89 (m, 1H), 8.08-8.14 (m, 1H), 10.94 (s, 1H); MS (ESI+) m/z 386 (M+H)+.

Example 24

2-[(1S,2S,3R,5R)-3-fluoro-6,6-dimethylbicyclo[3.1.1]hept-2-yl]-N-[4-oxo-2-(propan-2-yl)quinazolin-3(4H)-yl]acetamide Example 24A (1R,3R,5R)-3-fluoro-6,6-dimethylbicyclo[3.1.1]heptan-2-one To a solution of (+)-nopinone (Aldrich, 1.0 g, 7.2 mmol) in water (35 mL), was added sodium dodecyl sulfate (Aldrich, 2.1 g, 7.2 mmol). The mixture was heated to 80° C. and then 1-(chloromethyl)-4-fluoro-1,4-diazoniabicyclo[2.2.2]octane tetrafluoroborate (Alfa-aesar, 2.8 g, 8.0 mmol) was added in two portions with one hour interval and stirred at 80° C. overnight. The reaction mixture was cooled and extracted with diethyl ether (3×30 mL). The combined organic layers were dried over $MgSO_4$, filtered and concentrated under reduced pressure. The residue was purified by column chromatography ($SiO_2$, 0-20% of ethyl acetate in hexanes) to obtain 0.4 g of the title compound. MS ($DCI/NH_3$) m/z 174 $(M+NH_4)^+$.

Example 24B

Ethyl 2-((1R,3R,5R)-3-fluoro-6,6-dimethylbicyclo[3.1.1]heptan-2-ylidene)acetate

Example 24A, NaH and triethyl phosphonoacetate were reacted using method analogous to that described in Example 22A to provide the title compound. MS (DCI/NH$_3$) m/z 244 (M+NH$_4$)$^+$

Example 24C

Ethyl 2-((1S,2S,3R,5R)-3-fluoro-6,6-dimethylbicyclo[3.1.1]heptan-2-yl)acetate

Example 24B, pd/C and H$_2$ gas were reacted as described in Example 22B to provide the title compound. MS (DCI/NH$_3$) m/z 246 (M+NH$_4$)$^+$.

2-((1S,2S,3R,5R)-3-fluoro-6,6-dimethylbicyclo[3.1.1]heptan-2-yl)acetic acid

Example 24C and NaOH were reacted as described in Example 22C to provide the title compound. MS (DCI/NH$_3$) m/z 218 (M+NH$_4$)$^+$.

Example 24E

2-[(1S,2S,3R,5R)-3-fluoro-6,6-dimethylbicyclo[3.1.1]hept-2-yl]-N-(2-isopropyl-4-oxoquinazolin-3(4H)-yl)acetamide 3-Amino-2-isopropyl-4(3H)-quinazolinone, Example 24D, and 1-propanephosphonic acid were reacted using method analogous to that described in Example 22D to provide the title compound. $^1$H NMR (300 MHz, CDCl$_3$) δ ppm 0.89-0.97 (m, 1H), 1.09 (d, 3H), 1.20 (m, 3H), 1.21 (d, J=6.4 Hz, 3H), 1.25 (d, J=6.8 Hz, 3H), 1.45-1.65 (m, 1H), 1.77-2.07 (m, 4H), 2.25-2.59 (m, 4H), 2.25-2.46 (m, 1H), 3.03-3.16 (m, 1H), 7.49-7.58 (m, 1H), 7.67 (d, J=7.8 Hz, 1H), 7.81-7.91 (m, 1H), 8.11 (dd, J=8.1, 1.4 Hz, 1H), 10.94 (d, 1H); MS (ESI+) m/z 386 (M+H)+.

Example 25

2-[(1R,3s,5S)-6,6-dimethylbicyclo[3.1.1]hept-3-yl]-N-[4-oxo-2-(propan-2-yl)quinazolin-3(4H)-yl]acetamide

Example 25A

Ethyl 2-((1R,3s,5S)-6,6-dimethylbicyclo[3.1.1]heptan-3-yl)acetate

To a suspension of sodium hydride (53 mg, 1.4 mmol, 60% in mineral oil) in tetrahydrofuran (8 mL) was added a solution of Example 23B (150 mg, 0.7) in tetrahydrofuran (2 mL). After the mixture was stirred at room temperature for 30 min, carbon disulfide (Aldrich, 120 μL, 2.0 mmol) was added and stirred for 1 hour at room temperature, then iodomethane (103 mg, 0.8 mmol) was added. After stirring for another 30 minutes, the reaction was quenched with saturated aqueous NaHCO$_3$ solution (5 mL) and extracted with ethyl acetate (2×10 mL). The combined organic layers were dried over Na$_2$SO$_4$, filtered and concentrated under reduced pressure. The residue was purified by column chromatography (SiO$_2$, 0-30% of ethyl acetate in hexanes) to obtain the xanthate intermediate. To a solution of the above xanthate intermediate (25 mg, 0.08 mmol) in toluene (5 mL) were added tributylstannane (27 mL, 0.095 mmol) and 2,2'-azabis(2-methylpropionitrile) (2.6 mg, 0.016 mmol). After refluxing overnight, the reaction mixture was cooled to room temperature, diluted with saturated aqueous NaHCO$_3$ solution (5 mL) and extracted with ethyl acetate (3×10 mL). The combined organic extracts were dried (Na$_2$SO$_4$), filtered, and concentrated under reduced pressure. The residue was purified by column chromatography using an Analogix® Intelliflash280™ (SiO$_2$, 0-50% of ethyl acetate in hexanes) to provide the 25 mg of the title compound. MS (DCI/NH$_3$) m/z 228 (M+NH$_4$)$^+$.

Example 25B 2-((1R,3s,5S)-6,6-dimethylbicyclo[3.1.1]heptan-3-yl)acetic acid

Example 25A and NaOH were reacted using method analogous to that described in Example 22C to provide the title compound. MS (DCI/NH$_3$) m/z 200 (M+NH$_4$)$^+$.

Example 25C 2-((1R,3s,5S)-6,6-dimethylbicyclo[3.1.1]heptan-3-yl)-N-(2-isopropyl-4-oxoquinazolin-3(4H)-yl)acetamide 3-Amino-2-isopropyl-4(3H)-quinazolinone, Example 25B, and 1-propanephosphonic acid were reacted using method analogous to that described in Example 22D to provide the title compound. $^1$H NMR (400 MHz, DMSO-d$_6$) δ ppm 0.90 (d, 3H), 0.91 (d, 3H), 1.21 (dd, 3H), 1.24 (dd, 3H), 1.33-1.54 (m, 3H), 1.54-1.81 (m, 2H), 1.95-2.10 (m, 1H), 2.30-2.49 (m, 2H), 2.61-2.76 (m, 1H), 3.06-3.18 (m, 1H), 5.60-5.80 (m, 2H), 7.50-7.58 (m, 1H), 7.68 (d, J=8.5 Hz, 1H), 7.81-7.89 (m, 1H), 8.12 (d, J=7.0 Hz, 1H), 10.97 (d, 1H)); MS (ESI+) m/z 368 (M+H)$^+$.

It is understood that the foregoing detailed description and accompanying examples are merely illustrative and are not to be taken as limitations upon the scope of the invention, which is defined solely by the appended claims and their equivalents. Various changes and modifications to the disclosed embodiments will be apparent to those skilled in the art. Such changes and modifications, including without limitation those relating to the chemical structures, substituents, derivatives, intermediates, syntheses, formulations and/or methods of use of the invention, may be made without departing from the spirit and scope thereof.

The invention claimed is:
1. A compound of formula (1)

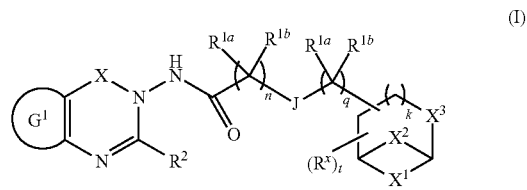

or a pharmaceutically acceptable salt thereof, wherein
J is absent, O, N(H), N(alkyl), S, S(O), or S(O)$_2$;
n is 1 or 2;
q is 0, 1, or 2;

ring $G^1$ is benzo which is unsubstituted or substituted with 1, 2, 3, or 4 substituents as represented by T, wherein each T is independently alkyl, alkenyl, alkynyl, halogen, haloalkyl, oxo, —CN, —NO$_2$, —OR$^a$, —NR$^a$R$^b$, —SR$^a$, —S(O)R$^a$, —S(O)$_2$R$^a$, —OC(O)R$^a$, —OC(O)NR$^a$R$^b$, —C(O)R$^a$, —C(O)OR$^a$, —C(O)NR$^a$R$^b$, —S(O)$_2$NR$^a$R$^b$, —N(R$^a$)C(O)NR$^a$R$^b$, —N(R$^a$)S(O)$_2$NR$^a$R$^b$, —(CR$^{za}$R$^{zb}$)$_m$—CN, —(CR$^{za}$R$^{zb}$)$_m$—NO$_2$, —(CR$^{za}$R$^{zb}$)$_m$—OR$^a$, —(CR$^{za}$R$^{zb}$)$_m$—NR$^a$R$^b$, —(CR$^{za}$R$^{zb}$)$_m$—S(O)R$^a$, —(CR$^{za}$R$^{zb}$)$_m$—S(O)$_2$R$^a$, —(CR$^{za}$R$^{zb}$)$_m$—OC(O)R$^a$, —(CR$^{za}$R$^{zb}$)$_m$—OC(O)NR$^a$R$^b$, —(CR$^{za}$R$^{zb}$)$_m$—C(O)R$^a$, —(CR$^{za}$R$^{zb}$)$_m$—C(O)OR$^a$, —(CR$^{za}$R$^{zb}$)$_m$—C(O)NR$^a$R$^b$, —(CR$^{za}$R$^{zb}$)$_m$—S(O)$_2$NR$^a$R$^b$, —(CR$^{za}$R$^{zb}$)$_m$—N(R$^a$)C(O)NR$^a$R$^b$, or —(CR$^{za}$R$^{zb}$)$_m$—N(R$^a$)S(O)$_2$NR$^a$R$^b$;

X is C(O);

$R^{1a}$ and $R^{1b}$, at each occurrence, are each independently hydrogen, alkyl, halogen, or haloalkyl; $R^{1a}$ and $R^{1b}$, together with the carbon atom to which they are attached, optionally form a 3-, 4-, 5-, or 6-membered monocyclic cycloalkyl when $R^{1a}$ and $R^{1b}$ are alkyl or haloalkyl;

k is 0 or 1;

$X^1$, $X^2$, and $X^3$ are each independently CH$_2$, O, S, S(O), or S(O)$_2$; with the proviso that at least two of $X^1$, $X^2$, and $X^3$ are CH$_2$;

t is 0, 1, 2, 3, or 4;

$R^x$ is an optional substituent on any substitutable atom of the ring containing $X^1$, $X^2$, and $X^3$, and each $R^x$ is independently alkyl, halogen, haloalkyl, OR$^a$, SR$^a$, or CN;

$R^2$ is hydrogen, alkyl, haloalkyl, —OR$^{2c}$, —OC(O)N(R$^{2c}$)(R$^{2f}$), —S(O)R$^{2c}$, —S(O)$_2$R$^{2c}$, —S(O)$_2$N(R$^{2c}$)(R$^{2f}$), —C(O)R$^{2c}$, —C(O)OR$^{2c}$, —C(O)N(R$^{2c}$)(R$^{2f}$), —N(R$^{2d}$)(R$^{2e}$), G$^{2a}$, —(CR$^{2a}$R$^{2b}$)$_p$-G$^{2a}$, —(CR$^{2a}$R$^{2b}$)$_p$—OR$^{2c}$, —(CR$^{2a}$R$^{2b}$)$_p$—OC(O)N(R$^{2c}$)(R$^{2f}$), —(CR$^{2a}$R$^{2b}$)$_p$—SR$^{2c}$, —(CR$^{2a}$R$^{2b}$)$_p$—S(O)R$^{2c}$, —(CR$^{2a}$R$^{2b}$)$_p$—S(O)$_2$R$^{2c}$, —(CR$^{2a}$R$^{2b}$)$_p$—S(O)$_2$N(R$^{2c}$)(R$^{2f}$), —(CR$^{2a}$R$^{2b}$)$_p$—C(O)R$^{2c}$, —(CR$^{2a}$R$^{2b}$)$_p$—C(O)OR$^{2c}$, —(CR$^{2a}$R$^{2b}$)$_p$—C(O)N(R$^{2c}$)(R$^{2f}$), or —(CR$^{2a}$R$^{2b}$)$_p$—N(R$^{2d}$)(R$^{2e}$);

$R^{2c}$, at each occurrence, is independently hydrogen, alkyl, haloalkyl, -alkylenyl-OR$^a$, -alkylenyl-N(R$^2$)(R$^{2g}$), -alkylenyl-CN, G$^{2a}$, or —(CR$^{2a}$R$^{2b}$)$_p$-G$^{2a}$;

$R^{2d}$ and $R^{2e}$, at each occurrence, are each independently hydrogen, alkyl, haloalkyl, G$^{2a}$-(CR$^{2a}$R$^{2b}$)$_p$-G$^{2a}$, C(O)R$^{2c}$, C(O)OR$^{2c}$, S(O)$_2$R$^{2c}$, -alkylenyl-OR$^a$, -alkylenyl-N(R$^2$)(R$^{2g}$), or -alkylenyl-CN;

$R^{2f}$, at each occurrence, is independently hydrogen, alkyl, or haloalkyl;

$R^{2g}$, at each occurrence, is independently hydrogen, alkyl, haloalkyl, C(O)R$^c$, C(O)OR$^c$, or S(O)$_2$R$^c$;

$G^{2a}$, at each occurrence, is independently aryl, heteroaryl, heterocycle, cycloalkyl, or cycloalkenyl; each of which is independently unsubstituted or substituted with 1, 2, 3, or 4 substituents independently selected from the group consisting of G$^a$, alkyl, alkenyl, alkynyl, halogen, haloalkyl, oxo, —CN, —NO$_2$, —OR$^a$, —OC(O)R$^a$, —OC(O)NR$^a$R$^b$, —NR$^a$R$^b$, —SR$^a$, —S(O)R$^a$, —S(O)$_2$R$^a$, —OC(O)R$^a$, —C(O)R$^a$, —C(O)OR$^a$, —C(O)NR$^a$R$^b$, —S(O)$_2$NR$^a$R$^b$, —N(R$^a$)C(O)NR$^a$R$^b$, —N(R$^a$)S(O)$_2$NR$^a$R$^b$, —(CR$^{za}$R$^{zb}$)$_m$-G$^a$, —(CR$^{za}$R$^{zb}$)$_m$—CN, —(CR$^{za}$R$^{zb}$)$_m$—NO$_2$, —(CR$^{za}$R$^{zb}$)$_m$—OR$^a$, —(CR$^{za}$R$^{zb}$)$_m$—OC(O)R$^a$, —(CR$^{za}$R$^{zb}$)$_m$—OC(O)NR$^a$R$^b$, —(CR$^{za}$R$^{zb}$)$_m$—NR$^a$R$^b$, —(CR$^{za}$R$^{zb}$)$_m$—SR$^a$—(CR$^{za}$R$^{zb}$)$_m$—S(O)$_2$R$^a$, —(CR$^{za}$R$^{zb}$)$_m$—OC(O)R$^a$, —(CR$^{za}$R$^{zb}$)$_m$—C(O)R$^a$, —(CR$^{za}$R$^{zb}$)$_m$—C(O)OR$^a$, —(CR$^{za}$R$^{zb}$)$_m$—C(O)NR$^a$R$^b$, —(CR$^{za}$R$^{zb}$)$_m$—S(O)$_2$NR$^a$R$^b$, —(CR$^{za}$R$^{zb}$)$_m$—N(R$^a$)C(O)NR$^a$R$^b$, and —(CR$^{za}$R$^{zb}$)$_m$—N(R$^a$)S(O)$_2$NR$^a$R$^b$, $G^a$, at each occurrence, is independently aryl, heteroaryl, heterocycle, cycloalkyl, or cycloalkenyl; each of which is independently unsubstituted or substituted with 1, 2, or 3 substituents selected from the group consisting of alkyl, alkenyl, alkynyl, halogen, haloalkyl, oxo, —CN, —NO$_2$, —OR$^a$, —NR$^a$R$^b$, —SR$^a$, —S(O)R$^a$, —S(O)$_2$R$^a$, —OC(O)R$^a$, —C(O)R$^a$, —C(O)OR$^a$, —C(O)NR$^a$R$^b$, —S(O)$_2$NR$^a$R$^b$, —N(R$^a$)C(O)NR$^a$R$^b$, —N(R$^a$)S(O)$_2$NR$^a$R$^b$, —(CR$^{za}$R$^{zb}$)$_m$—CN, —(CR$^{za}$R$^{zb}$)$_m$—NO$_2$, —(CR$^{za}$R$^{zb}$)$_m$—OR$^a$, —(CR$^{za}$R$^{zb}$)$_m$—NR$^a$R$^b$, —(CR$^{za}$R$^{zb}$)$_m$—SR$^a$, —(CR$^{za}$R$^{zb}$)$_m$—S(O)R$^a$, —(CR$^{za}$R$^{zb}$)$_m$—S(O)$_2$R$^a$, —(CR$^{za}$R$^{zb}$)$_m$—OC(O)R$^a$, —(CR$^{za}$R$^{zb}$)$_m$—C(O)R$^a$, —(CR$^{za}$R$^{zb}$)$_m$—C(O)OR$^a$, —(CR$^{za}$R$^{zb}$)$_m$—C(O)NR$^a$R$^b$, —(CR$^{za}$R$^{zb}$)$_m$—S(O)$_2$NR$^a$R$^b$, —(CR$^{za}$R$^{zb}$)$_m$—N(R$^a$)C(O)NR$^a$R$^b$, and —(CR$^{za}$R$^{zb}$)$_m$—N(R$^a$)S(O)$_2$NR$^a$R$^b$, $R^a$ and $R^b$, at each occurrence, are each independently hydrogen, alkyl, or haloalkyl;

$R^c$, at each occurrence, is independently alkyl or haloalkyl;

$R^{za}$, $R^{zb}$, $R^{2a}$, and $R^{2b}$, at each occurrence, are each independently hydrogen, alkyl, halogen, or haloalkyl; and m and p, at each occurrence, are each independently 1, 2, 3, or 4;

wherein heteroaryl, at each occurrence, is independently optionally substituted monocyclic or bicyclic heteroaryl; and wherein heterocycle, at each occurrence, is independently optionally substituted monocyclic, bicyclic, or tricyclic heterocycle.

2. The compound of claim 1 or a pharmaceutically acceptable salt thereof, wherein $X^1$, $X^2$, and $X^3$ are CH$_2$.

3. The compound of claim 2 or a pharmaceutically acceptable salt thereof, wherein J is absent, O, or S.

4. The compound of claim 3 or a pharmaceutically acceptable salt thereof, wherein $R^2$ is hydrogen, alkyl, haloalkyl, $G^{2a}$, or NR$^{2d}$R$^{2e}$.

5. The compound of claim 3 or a pharmaceutically acceptable salt thereof, wherein $R^2$ is $G^{2a}$.

6. The compound of claim 3 or a pharmaceutically acceptable salt thereof, wherein $R^2$ is hydrogen, alkyl, or haloalkyl.

7. The compound of claim 3 or a pharmaceutically acceptable salt thereof, wherein $R^2$ is NR$^{2d}$R$^{2e}$.

8. The compound of claim 1 of formula (I-d)

(I-d)

or a pharmaceutically acceptable salt thereof.

9. The compound of claim 8 or a pharmaceutically acceptable salt thereof, wherein $X^1$, $X^2$, and $X^3$ are CH$_2$.

10. The compound of claim 9 or a pharmaceutically acceptable salt thereof, wherein
R² is hydrogen alkyl, haloalkyl, $G^{2a}$, or $NR^{2d}R^{2e}$.

11. The compound of claim 10 or a pharmaceutically acceptable salt thereof, wherein
$R^{1a}$ and $R^{1b}$ are hydrogen or alkyl;
n is 1, and
q is 0 or 1.

12. The compound of formula (1) or a pharmaceutically acceptable salt thereof, wherein the compound is selected from the group consisting of
2-[(1S,2S,5S)-6,6-dimethylbicyclo[3.1.1]hept-2-yl]-N-[4-oxo-2-(propan-2-yl)quinazolin-3(4H)-yl]acetamide;
2-[(1S,2S,5S)-6,6-dimethylbicyclo[3.1.1]hept-2-yl]-N-(2-ethyl-4-oxoquinazolin-3(4H)-yl)acetamide;
N-(2-cyclopropyl-7-fluoro-4-oxoquinazolin-3(4H)-yl)-2-[(1S,2S,5S)-6,6-dimethylbicyclo[3.1.1]hept-2-yl]acetamide;
N-[2-cyclopropyl-4-oxo-7-(trifluoromethyl)quinazolin-3(4H)-yl]-2-[(1S,2S,5S)-6,6-dimethylbicyclo[3.1.1]hept-2-yl]acetamide;
N-(2-cyclopropyl-4-oxoquinazolin-3(4H)-yl)-2-[(1S,2S,5S)-6,6-dimethylbicyclo[3.1.1]hept-2-yl]acetamide;
2-[(1S,2S,5S)-6,6-dimethylbicyclo[3.1.1]hept-2-yl]-N-[4-oxo-2-(trifluoromethyl)quinazolin-3(4H)-yl]acetamide;
2-[(1S,2R,5S)-(6,6-dimethylbicyclo[3.1.1]hept-2-yl)methoxy]-N-[4-oxo-2-(propan-2-yl)quinazolin-3(4H)-yl]acetamide;
2-({[(1S,2R,5S)-6,6-dimethylbicyclo[3.1.1]hept-2-yl]methyl}sulfanyl)-N-[4-oxo-2-(propan-2-yl)quinazolin-3(4H)-yl]propanamide;
2-{2-[(1S,2S,5S)-6,6-dimethylbicyclo[3.1.1]hept-2-yl]ethoxy}-N-[4-oxo-2-(propan-2-yl)quinazolin-3(4H)-yl]acetamide;
3-({[(1S,2R,5S)-6,6-dimethylbicyclo[3.1.1]hept-2-yl]methyl}sulfanyl)-N-[4-oxo-2-(propan-2-yl)quinazolin-3(4H)-yl]propanamide;
2-({[(1S,2R,5S)-6,6-dimethylbicyclo[3.1.1]hept-2-yl]methyl}sulfanyl)-N-[4-oxo-2-(propan-2-yl)quinazolin-3(4H)-yl]acetamide;
2-[(1S,2S,5S)-6,6-dimethylbicyclo[3.1.1]hept-2-yl]-N-[6-fluoro-4-oxo-2-(propan-2-yl)quinazolin-3(4H)-yl]acetamide;
2-[(1S,2S,5S)-6,6-dimethylbicyclo[3.1.1]hept-2-yl]-N-[4-oxo-2-(2,2,2-trifluoroethyl)quinazolin-3(4H)-yl]acetamide;
2-[(1S,2S,5S)-6,6-dimethylbicyclo[3.1.1]hept-2-yl]-N-(4-oxoquinazolin-3(4H)-yl)acetamide;
2-[(1S,2S,5S)-6,6-dimethylbicyclo[3.1.1]hept-2-yl]-N-(2-methyl-4-oxoquinazolin-3(4H)-yl)acetamide;
N-[6-chloro-4-oxo-2-(propan-2-yl)quinazolin-3(4H)-yl]-2-[(1S,2S,5S)-6,6-dimethylbicyclo[3.1.1]hept-2-yl]acetamide;
N-[2-(diethylamino)-4-oxoquinazolin-3(4H)-yl]-2-[(1S,2S,5S)-6,6-dimethylbicyclo[3.1.1]hept-2-yl]acetamide;
2-[(1S,2R,5S)-6,6-dimethylbicyclo[3.1.1]hept-2-yl]-N-[4-oxo-2-(propan-2-yl)quinazolin-3(4H)-yl]acetamide;
(±)-2-(bicyclo[2.1.1]hex-2-yl)-N-[4-oxo-2-(propan-2-yl)quinazolin-3(4H)-yl]acetamide;
2-[(1R,3R,5S)-2-fluoro-6,6-dimethylbicyclo[3.1.1]hept-3-yl]-N-[4-oxo-2-(propan-2-yl)quinazolin-3(4H)-yl]acetamide;
2-[(1S,2S,3R,5R)-3-fluoro-6,6-dimethylbicyclo[3.1.1]hept-2-yl]-N-[4-oxo-2-(propan-2-yl)quinazolin-3(4H)-yl]acetamide; and
2-[(1R,3s,5S)-6,6-dimethylbicyclo[3.1.1]hept-3-yl]-N-[4-oxo-2-(propan-2-yl)quinazolin-3(4H)-yl]acetamide.

13. A pharmaceutical composition comprising a therapeutically effective amount of a compound of formula (1) according to claim 1 or a pharmaceutically acceptable salt thereof, with one or more pharmaceutically acceptable carriers.

14. A method for treating pain in a subject in need of such treatment comprising administering to the subject a therapeutically effective amount of a compound of formula (1) according to claim 1, or a pharmaceutically acceptable salt thereof, alone or in combination with one or more pharmaceutically acceptable carrier.

* * * * *